US008296076B2

(12) United States Patent
Fan et al.

(10) Patent No.: US 8,296,076 B2
(45) Date of Patent: Oct. 23, 2012

(54) NONINVASIVE DIAGNOSIS OF FETAL ANEUOPLOIDY BY SEQUENCING

(75) Inventors: Hei-Mun Christina Fan, Fremont, CA (US); Stephen R. Quake, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 13/452,083

(22) Filed: Apr. 20, 2012

(65) Prior Publication Data
US 2012/0208710 A1    Aug. 16, 2012

Related U.S. Application Data

(60) Continuation of application No. 12/696,509, filed on Jan. 29, 2010, now Pat. No. 8,195,415, which is a division of application No. 12/560,708, filed on Sep. 16, 2009.

(60) Provisional application No. 61/098,758, filed on Sep. 20, 2008.

(51) Int. Cl.
*G01N 33/48*    (2006.01)
(52) U.S. Cl. .......................................................... 702/20
(58) Field of Classification Search .................... 702/20, 702/182–185
See application file for complete search history.

(56) References Cited

U.S. PATENT DOCUMENTS

| | | |
|---|---|---|
| 4,508,625 A | 4/1985 | Graham |
| 4,675,286 A | 6/1987 | Calenoff |
| 4,789,628 A | 12/1988 | Nayak |
| 4,800,159 A | 1/1989 | Mullis et al. |
| 4,971,904 A | 11/1990 | Luddy |
| 4,977,078 A | 12/1990 | Niimura et al. |
| 5,153,117 A | 10/1992 | Simons |
| 5,215,926 A | 6/1993 | Etchells, III et al. |
| 5,296,375 A | 3/1994 | Kricka et al. |
| 5,300,779 A | 4/1994 | Hillman et al. |
| 5,304,487 A | 4/1994 | Wilding et al. |

(Continued)

FOREIGN PATENT DOCUMENTS
EP        0637996 B1      7/1997
(Continued)

OTHER PUBLICATIONS

U.S. Appl. No. 11/825,298, filed Jul. 5, 2007, Lopez et al.
(Continued)

*Primary Examiner* — Edward Raymond
(74) *Attorney, Agent, or Firm* — David J. Aston; Peters Verny, LLP

(57) ABSTRACT

Disclosed is a method to achieve digital quantification of DNA (i.e., counting differences between identical sequences) using direct shotgun sequencing followed by mapping to the chromosome of origin and enumeration of fragments per chromosome. The preferred method uses massively parallel sequencing, which can produce tens of millions of short sequence tags in a single run and enabling a sampling that can be statistically evaluated. By counting the number of sequence tags mapped to a predefined window in each chromosome, the over- or under-representation of any chromosome in maternal plasma DNA contributed by an aneuploid fetus can be detected. This method does not require the differentiation of fetal versus maternal DNA. The median count of autosomal values is used as a normalization constant to account for differences in total number of sequence tags is used for comparison between samples and between chromosomes.

15 Claims, 17 Drawing Sheets

U.S. PATENT DOCUMENTS

| | | |
|---|---|---|
| 5,427,663 A | 6/1995 | Austin et al. |
| 5,427,946 A | 6/1995 | Kricka et al. |
| 5,432,054 A | 7/1995 | Saunders et al. |
| 5,447,842 A | 9/1995 | Simons |
| 5,486,335 A | 1/1996 | Wilding et al. |
| 5,498,392 A | 3/1996 | Wilding et al. |
| 5,529,903 A | 6/1996 | Kübler et al. |
| 5,556,773 A | 9/1996 | Youmo |
| 5,629,147 A | 5/1997 | Asgari et al. |
| 5,639,669 A | 6/1997 | Ledley |
| 5,641,628 A | 6/1997 | Bianchi |
| 5,646,001 A | 7/1997 | Terstappen et al. |
| 5,676,849 A | 10/1997 | Sammons et al. |
| 5,707,799 A | 1/1998 | Hansmann et al. |
| 5,709,943 A | 1/1998 | Coleman et al. |
| 5,715,946 A | 2/1998 | Reichenbach |
| 5,726,026 A | 3/1998 | Wilding et al. |
| 5,750,339 A | 5/1998 | Smith |
| 5,766,843 A | 6/1998 | Asgari et al. |
| 5,770,029 A | 6/1998 | Nelson et al. |
| 5,798,042 A | 8/1998 | Chu et al. |
| 5,837,115 A | 11/1998 | Austin et al. |
| 5,840,502 A | 11/1998 | Van Vlasselaer |
| 5,842,787 A | 12/1998 | Koph-Sill et al. |
| 5,858,649 A | 1/1999 | Asgari et al. |
| 5,866,345 A | 2/1999 | Wilding et al. |
| 5,879,883 A | 3/1999 | Benson et al. |
| 5,891,651 A | 4/1999 | Roche et al. |
| 5,928,880 A | 7/1999 | Wilding et al. |
| 5,952,173 A | 9/1999 | Hansmann et al. |
| 5,962,234 A | 10/1999 | Golbus |
| 5,962,237 A | 10/1999 | Ts'o et al. |
| 5,962,332 A | 10/1999 | Singer et al. |
| 5,972,721 A | 10/1999 | Bruno et al. |
| 5,993,665 A | 11/1999 | Terstappen et al. |
| 5,994,057 A | 11/1999 | Mansfield |
| 5,994,517 A | 11/1999 | Ts'o et al. |
| 6,007,690 A | 12/1999 | Nelson et al. |
| 6,008,007 A | 12/1999 | Fruehauf et al. |
| 6,013,188 A | 1/2000 | Terstappen et al. |
| 6,066,449 A | 5/2000 | Ditkoff et al. |
| 6,074,827 A | 6/2000 | Nelson et al. |
| 6,100,029 A | 8/2000 | Lapidus et al. |
| 6,143,496 A | 11/2000 | Brown et al. |
| 6,143,576 A | 11/2000 | Buechler |
| 6,154,707 A | 11/2000 | Livak et al. |
| 6,156,270 A | 12/2000 | Buechler |
| 6,159,685 A | 12/2000 | Pinkel et al. |
| 6,176,962 B1 | 1/2001 | Soane et al. |
| 6,184,043 B1 | 2/2001 | Fodstad et al. |
| 6,186,660 B1 | 2/2001 | Koph-Sill et al. |
| 6,197,523 B1 | 3/2001 | Rimm et al. |
| 6,200,765 B1 | 3/2001 | Murphy et al. |
| 6,210,891 B1 | 4/2001 | Nyren et al. |
| 6,214,558 B1 | 4/2001 | Shuber et al. |
| 6,235,474 B1 | 5/2001 | Feinberg |
| 6,258,540 B1 | 7/2001 | Lo et al. |
| 6,265,229 B1 | 7/2001 | Fodstad et al. |
| 6,300,077 B1 | 10/2001 | Shuber et al. |
| 6,344,326 B1 | 2/2002 | Nelson et al. |
| 6,361,958 B1 | 3/2002 | Shieh et al. |
| 6,365,362 B1 | 4/2002 | Terstappen et al. |
| 6,368,871 B1 | 4/2002 | Christel et al. |
| 6,376,181 B2 | 4/2002 | Ramsey et al. |
| 6,383,759 B1 | 5/2002 | Murphy et al. |
| 6,387,707 B1 | 5/2002 | Seul et al. |
| 6,391,559 B1 | 5/2002 | Brown et al. |
| 6,394,942 B2 | 5/2002 | Moon et al. |
| 6,399,364 B1 | 6/2002 | Reeve et al. |
| 6,432,630 B1 | 8/2002 | Blankenstein |
| 6,440,706 B1 | 8/2002 | Vogelstein et al. |
| 6,444,461 B1 | 9/2002 | Knapp et al. |
| 6,454,938 B2 | 9/2002 | Moon et al. |
| 6,479,299 B1 | 11/2002 | Parce et al. |
| 6,511,967 B1 | 1/2003 | Weissleder et al. |
| 6,517,234 B1 | 2/2003 | Koph-Sill et al. |
| 6,540,895 B1 | 4/2003 | Spence et al. |
| 6,576,478 B1 | 6/2003 | Wagner et al. |
| 6,582,904 B2 | 6/2003 | Dahm |
| 6,582,969 B1 | 6/2003 | Wagner et al. |
| 6,596,144 B1 | 7/2003 | Regnier et al. |
| 6,596,545 B1 | 7/2003 | Wagner et al. |
| 6,613,525 B2 | 9/2003 | Nelson et al. |
| 6,618,679 B2 | 9/2003 | Loehriein et al. |
| 6,632,619 B1 | 10/2003 | Harrison et al. |
| 6,632,652 B1 | 10/2003 | Austin et al. |
| 6,637,463 B1 | 10/2003 | Lei et al. |
| 6,645,731 B2 | 11/2003 | Terstappen et al. |
| 6,664,056 B2 | 12/2003 | Lo et al. |
| 6,664,104 B2 | 12/2003 | Pourahmadi et al. |
| 6,673,541 B1 | 1/2004 | Klein et al. |
| 6,674,525 B2 | 1/2004 | Bardell et al. |
| 6,685,841 B2 | 2/2004 | Lopez et al. |
| 6,689,615 B1 | 2/2004 | Murto et al. |
| 6,746,503 B1 | 6/2004 | Benett et al. |
| 6,753,147 B2 | 6/2004 | Vogelstein et al. |
| 6,783,928 B2 | 8/2004 | Hvichia et al. |
| 6,818,184 B2 | 11/2004 | Fulwyler et al. |
| 6,830,936 B2 | 12/2004 | Anderson et al. |
| 6,858,439 B1 | 2/2005 | Xu et al. |
| 6,875,619 B2 | 4/2005 | Blackburn |
| 6,893,881 B1 | 5/2005 | Fodstad et al. |
| 6,906,182 B2 | 6/2005 | Ts'o et al. |
| 6,911,345 B2 | 6/2005 | Quake et al. |
| 6,913,697 B2 | 7/2005 | Lopez et al. |
| 6,927,028 B2 | 8/2005 | Dennis et al. |
| 6,953,668 B1 | 10/2005 | Israeli et al. |
| 6,960,449 B2 | 11/2005 | Wang et al. |
| 7,115,709 B1 | 10/2006 | Gray et al. |
| 7,150,812 B2 | 12/2006 | Huang et al. |
| 7,171,975 B2 | 2/2007 | Moon et al. |
| 7,190,818 B2 | 3/2007 | Ellis et al. |
| 7,192,698 B1 | 3/2007 | Kinch et al. |
| 7,198,787 B2 | 4/2007 | Fodstad et al. |
| 7,208,275 B2 | 4/2007 | Gocke et al. |
| 7,212,660 B2 | 5/2007 | Wetzel et al. |
| 7,220,594 B2 | 5/2007 | Foster et al. |
| 7,227,002 B1 | 6/2007 | Kufer et al. |
| 7,229,838 B2 | 6/2007 | Foster et al. |
| 7,250,256 B2 | 7/2007 | Reinhard et al. |
| 7,252,976 B2 | 8/2007 | Lin et al. |
| 7,258,987 B2 | 8/2007 | Lamorte et al. |
| 7,262,177 B2 | 8/2007 | Ts'o et al. |
| 7,262,269 B2 | 8/2007 | Lam et al. |
| 7,264,972 B2 | 9/2007 | Foster |
| 7,272,252 B2 | 9/2007 | De La Torre-Bueno et al. |
| 7,276,170 B2 | 10/2007 | Oakey et al. |
| 7,332,277 B2 | 2/2008 | Dhallan |
| 7,442,506 B2 | 10/2008 | Dhallan |
| 7,476,363 B2 | 1/2009 | Unger et al. |
| 7,645,576 B2 | 1/2010 | Lo et al. |
| 7,655,399 B2 | 2/2010 | Cantor et al. |
| 2001/0007749 A1 | 7/2001 | Feinberg |
| 2001/0051341 A1 | 12/2001 | Lo et al. |
| 2001/0053958 A1 | 12/2001 | Ried et al. |
| 2002/0006621 A1 | 1/2002 | Bianchi |
| 2002/0009738 A1 | 1/2002 | Houghton et al. |
| 2002/0012930 A1 | 1/2002 | Rothberg et al. |
| 2002/0012931 A1 | 1/2002 | Waldman et al. |
| 2002/0016450 A1 | 2/2002 | Laugharn et al. |
| 2002/0019001 A1 | 2/2002 | Light |
| 2002/0028431 A1 | 3/2002 | Julien |
| 2002/0058332 A1 | 5/2002 | Quake et al. |
| 2002/0076825 A1 | 6/2002 | Cheng et al. |
| 2002/0086329 A1 | 7/2002 | Shvets et al. |
| 2002/0110835 A1 | 8/2002 | Kumar |
| 2002/0123078 A1 | 9/2002 | Seul et al. |
| 2002/0137088 A1 | 9/2002 | Bianchi |
| 2002/0164816 A1 | 11/2002 | Quake |
| 2002/0166760 A1 | 11/2002 | Prentiss et al. |
| 2002/0172987 A1 | 11/2002 | Terstappen et al. |
| 2003/0004402 A1 | 1/2003 | Hitt et al. |
| 2003/0017514 A1 | 1/2003 | Pachmann et al. |
| 2003/0022207 A1 | 1/2003 | Balasubramanian |
| 2003/0033091 A1 | 2/2003 | Opalsky et al. |
| 2003/0044388 A1 | 3/2003 | Dennis et al. |
| 2003/0072682 A1 | 4/2003 | Kikinis |

| | | | | | |
|---|---|---|---|---|---|
| 2003/0077292 A1 | 4/2003 | Hanash et al. | 2006/0051265 A1 | 3/2006 | Mohamed et al. |
| 2003/0119077 A1 | 6/2003 | Ts'o et al. | 2006/0051775 A1 | 3/2006 | Bianchi et al. |
| 2003/0119724 A1 | 6/2003 | Ts'o et al. | 2006/0060767 A1 | 3/2006 | Wang et al. |
| 2003/0129676 A1 | 7/2003 | Terstappen et al. | 2006/0072805 A1 | 4/2006 | Tsipouras et al. |
| 2003/0153085 A1 | 8/2003 | Leary et al. | 2006/0073125 A1 | 4/2006 | Clarke et al. |
| 2003/0159999 A1 | 8/2003 | Oakey et al. | 2006/0094109 A1 | 5/2006 | Trainer |
| 2003/0165852 A1 | 9/2003 | Schueler et al. | 2006/0121452 A1 | 6/2006 | Dhallan |
| 2003/0170631 A1 | 9/2003 | Houghton et al. | 2006/0121624 A1 | 6/2006 | Huang et al. |
| 2003/0170703 A1 | 9/2003 | Piper et al. | 2006/0128006 A1 | 6/2006 | Gerhardt et al. |
| 2003/0175990 A1 | 9/2003 | Heyenga | 2006/0134599 A1 | 6/2006 | Toner et al. |
| 2003/0186255 A1 | 10/2003 | Williams et al. | 2006/0160105 A1 | 7/2006 | Dhallan |
| 2003/0190602 A1 | 10/2003 | Pressman et al. | 2006/0160150 A1 | 7/2006 | Seilhamer et al. |
| 2003/0199685 A1 | 10/2003 | Pressman et al. | 2006/0160243 A1 | 7/2006 | Tang et al. |
| 2003/0204331 A1 | 10/2003 | Whitney et al. | 2006/0183886 A1 | 8/2006 | Ts'o et al. |
| 2003/0206901 A1 | 11/2003 | Chen | 2006/0205057 A1 | 9/2006 | Wayner et al. |
| 2003/0232350 A1 | 12/2003 | Afar et al. | 2006/0223178 A1 | 10/2006 | Barber et al. |
| 2004/0005582 A1 | 1/2004 | Shipwash | 2006/0252054 A1 | 11/2006 | Lin et al. |
| 2004/0009471 A1 | 1/2004 | Cao | 2006/0252061 A1 | 11/2006 | Zabeau et al. |
| 2004/0018116 A1 | 1/2004 | Desmond et al. | 2006/0252068 A1 | 11/2006 | Lo et al. |
| 2004/0018509 A1 | 1/2004 | Bianchi | 2006/0252071 A1 | 11/2006 | Lo et al. |
| 2004/0043506 A1 | 3/2004 | Haussecker et al. | 2006/0252087 A1 | 11/2006 | Tang et al. |
| 2004/0048360 A1 | 3/2004 | Wada et al. | 2007/0015171 A1 | 1/2007 | Bianchi et al. |
| 2004/0053352 A1 | 3/2004 | Ouyang et al. | 2007/0017633 A1 | 1/2007 | Tonkovich et al. |
| 2004/0072278 A1 | 4/2004 | Chou et al. | 2007/0026381 A1 | 2/2007 | Huang et al. |
| 2004/0096892 A1 | 5/2004 | Wang et al. | 2007/0026413 A1 | 2/2007 | Toner et al. |
| 2004/0137452 A1 | 7/2004 | Levett et al. | 2007/0026414 A1 | 2/2007 | Fuchs et al. |
| 2004/0137470 A1 | 7/2004 | Dhallan | 2007/0026415 A1 | 2/2007 | Fuchs et al. |
| 2004/0142463 A1 | 7/2004 | Walker et al. | 2007/0026416 A1 | 2/2007 | Fuchs |
| 2004/0144651 A1 | 7/2004 | Huang et al. | 2007/0026417 A1 | 2/2007 | Fuchs et al. |
| 2004/0166555 A1 | 8/2004 | Braff et al. | 2007/0026418 A1 | 2/2007 | Fuchs et al. |
| 2004/0171091 A1 | 9/2004 | Lesko et al. | 2007/0026419 A1 | 2/2007 | Fuchs et al. |
| 2004/0185495 A1 | 9/2004 | Schueler et al. | 2007/0026469 A1 | 2/2007 | Fuchs et al. |
| 2004/0203037 A1 | 10/2004 | Lo et al. | 2007/0037172 A1 | 2/2007 | Chiu et al. |
| 2004/0209299 A1 | 10/2004 | Pinter et al. | 2007/0037173 A1 | 2/2007 | Allard et al. |
| 2004/0214240 A1 | 10/2004 | Cao | 2007/0037273 A1 | 2/2007 | Shuler et al. |
| 2004/0232074 A1 | 11/2004 | Peters et al. | 2007/0037275 A1 | 2/2007 | Shuler et al. |
| 2004/0241707 A1 | 12/2004 | Gao et al. | 2007/0042238 A1 | 2/2007 | Kim et al. |
| 2005/0014208 A1 | 1/2005 | Krehan et al. | 2007/0042339 A1 | 2/2007 | Toner et al. |
| 2005/0019792 A1 | 1/2005 | McBride et al. | 2007/0042360 A1 | 2/2007 | Afar et al. |
| 2005/0037388 A1 | 2/2005 | Antonarakis et al. | 2007/0042368 A1 | 2/2007 | Zehentner-Wilkinson et al. |
| 2005/0042623 A1 | 2/2005 | Ault-Riche et al. | 2007/0048750 A1 | 3/2007 | Peck et al. |
| 2005/0042685 A1 | 2/2005 | Albert et al. | 2007/0054268 A1 | 3/2007 | Sutherland et al. |
| 2005/0049793 A1 | 3/2005 | Paterlini-Brechot | 2007/0054287 A1 | 3/2007 | Bloch |
| 2005/0061962 A1 | 3/2005 | Mueth et al. | 2007/0059680 A1 | 3/2007 | Kapur et al. |
| 2005/0118591 A1 | 6/2005 | Tamak et al. | 2007/0059683 A1 | 3/2007 | Barber et al. |
| 2005/0129581 A1 | 6/2005 | McBride et al. | 2007/0059716 A1 | 3/2007 | Balis et al. |
| 2005/0145496 A1 | 7/2005 | Goodsaid et al. | 2007/0059718 A1 | 3/2007 | Toner et al. |
| 2005/0147977 A1 | 7/2005 | Koo et al. | 2007/0059719 A1 | 3/2007 | Grisham et al. |
| 2005/0153342 A1 | 7/2005 | Chen | 2007/0059737 A1 | 3/2007 | Baker et al. |
| 2005/0158754 A1 | 7/2005 | Puffenberger et al. | 2007/0059774 A1 | 3/2007 | Grisham et al. |
| 2005/0164241 A1 | 7/2005 | Hahn et al. | 2007/0059781 A1 | 3/2007 | Kapur et al. |
| 2005/0175996 A1 | 8/2005 | Chen | 2007/0059785 A1 | 3/2007 | Bacus et al. |
| 2005/0181353 A1 | 8/2005 | Rao et al. | 2007/0065845 A1 | 3/2007 | Baker et al. |
| 2005/0181410 A1 | 8/2005 | Shaffer et al. | 2007/0065858 A1 | 3/2007 | Haley |
| 2005/0181463 A1 | 8/2005 | Rao et al. | 2007/0071762 A1 | 3/2007 | Ts'o et al. |
| 2005/0196785 A1 | 9/2005 | Quake et al. | 2007/0072228 A1 | 3/2007 | Brauch |
| 2005/0207940 A1 | 9/2005 | Butler et al. | 2007/0072290 A1 | 3/2007 | Hvichia |
| 2005/0211556 A1 | 9/2005 | Childers et al. | 2007/0077578 A1 | 4/2007 | Penning et al. |
| 2005/0214855 A1 | 9/2005 | Wagner et al. | 2007/0092444 A1 | 4/2007 | Benos et al. |
| 2005/0221341 A1 | 10/2005 | Shimkets et al. | 2007/0092881 A1 | 4/2007 | Ohnishi et al. |
| 2005/0221373 A1 | 10/2005 | Enzelberger et al. | 2007/0092917 A1 | 4/2007 | Guyon |
| 2005/0239101 A1 | 10/2005 | Sukumar et al. | 2007/0099207 A1 | 5/2007 | Fuchs et al. |
| 2005/0244843 A1 | 11/2005 | Chen et al. | 2007/0099219 A1 | 5/2007 | Teverovskiy et al. |
| 2005/0250111 A1 | 11/2005 | Xie et al. | 2007/0099289 A1 | 5/2007 | Irimia et al. |
| 2005/0250155 A1 | 11/2005 | Lesko et al. | 2007/0105105 A1 | 5/2007 | Clelland et al. |
| 2005/0250199 A1 | 11/2005 | Anderson et al. | 2007/0105133 A1 | 5/2007 | Clark et al. |
| 2005/0252773 A1 | 11/2005 | McBride et al. | 2007/0110773 A1 | 5/2007 | Asina et al. |
| 2005/0255001 A1 | 11/2005 | Padmanabhan et al. | 2007/0117158 A1 | 5/2007 | Coumans et al. |
| 2005/0262577 A1 | 11/2005 | Guelly et al. | 2007/0122856 A1 | 5/2007 | Georges et al. |
| 2005/0266433 A1 | 12/2005 | Kapur et al. | 2007/0122896 A1 | 5/2007 | Shuler et al. |
| 2005/0272103 A1 | 12/2005 | Chen | 2007/0128655 A1 | 6/2007 | Obata |
| 2005/0282196 A1 | 12/2005 | Costa | 2007/0131622 A1 | 6/2007 | Oakey et al. |
| 2005/0282293 A1 | 12/2005 | Cosmen et al. | 2007/0134658 A1 | 6/2007 | Bohmer et al. |
| 2005/0287611 A1 | 12/2005 | Nugent et al. | 2007/0134713 A1 | 6/2007 | Cao |
| 2006/0000772 A1 | 1/2006 | Sano et al. | 2007/0135621 A1 | 6/2007 | Bourel et al. |
| 2006/0008807 A1 | 1/2006 | O'Hara et al. | 2007/0141587 A1 | 6/2007 | Baker et al. |
| 2006/0008824 A1 | 1/2006 | Ronaghi et al. | 2007/0141588 A1 | 6/2007 | Baker et al. |
| 2006/0024756 A1 | 2/2006 | Tibbe et al. | 2007/0141717 A1 | 6/2007 | Carpenter et al. |
| 2006/0046258 A1 | 3/2006 | Lapidus et al. | 2007/0154928 A1 | 7/2007 | Mack et al. |

| | | | | | | |
|---|---|---|---|---|---|---|
| 2007/0154960 | A1 | 7/2007 | Connelly et al. | EP | 1313882 B1 | 5/2007 |
| 2007/0160503 | A1 | 7/2007 | Sethu et al. | EP | 1803822 A1 | 7/2007 |
| 2007/0160974 | A1 | 7/2007 | Sidhu et al. | EP | 951645 B1 | 8/2007 |
| 2007/0160984 | A1 | 7/2007 | Huang et al. | EP | 1813681 A2 | 8/2007 |
| 2007/0161064 | A1 | 7/2007 | Kinch et al. | EP | 1832661 A1 | 9/2007 |
| 2007/0166770 | A1 | 7/2007 | Hsieh et al. | EP | 1757694 A3 | 2/2008 |
| 2007/0170811 | A1 | 7/2007 | Rubel | EP | 2161347 A3 | 6/2010 |
| 2007/0172903 | A1 | 7/2007 | Toner et al. | WO | WO 90/06509 A1 | 6/1990 |
| 2007/0178067 | A1 | 8/2007 | Maier et al. | WO | WO 91/07660 A1 | 5/1991 |
| 2007/0178458 | A1 | 8/2007 | O'Brien et al. | WO | WO 91/16452 A1 | 10/1991 |
| 2007/0187250 | A1 | 8/2007 | Huang et al. | WO | WO 93/22053 A1 | 11/1993 |
| 2007/0196663 | A1 | 8/2007 | Schwartz et al. | WO | WO 94/29707 A1 | 12/1994 |
| 2007/0196820 | A1 | 8/2007 | Kapur et al. | WO | WO 95/09245 A1 | 4/1995 |
| 2007/0196840 | A1 | 8/2007 | Roca et al. | WO | WO 97/46882 A1 | 12/1997 |
| 2007/0196869 | A1 | 8/2007 | Perez et al. | WO | WO 98/02528 A1 | 1/1998 |
| 2007/0202106 | A1 | 8/2007 | Palucka et al. | WO | WO 98/10267 A1 | 3/1998 |
| 2007/0202109 | A1 | 8/2007 | Nakamura et al. | WO | WO 99/22868 A1 | 5/1999 |
| 2007/0202525 | A1 | 8/2007 | Quake et al. | WO | WO 99/44064 A1 | 9/1999 |
| 2007/0202536 | A1 | 8/2007 | Yamanishi et al. | WO | WO 99/61888 A2 | 12/1999 |
| 2007/0207351 | A1 | 9/2007 | Christensen et al. | WO | WO 00/40750 A1 | 7/2000 |
| 2007/0207466 | A1 | 9/2007 | Cantor et al. | WO | WO 00/62931 A1 | 10/2000 |
| 2007/0212689 | A1 | 9/2007 | Bianchi et al. | WO | WO 01/35071 A2 | 5/2001 |
| 2007/0212698 | A1 | 9/2007 | Bendele et al. | WO | WO 01/51668 A1 | 7/2001 |
| 2007/0212737 | A1 | 9/2007 | Clarke et al. | WO | WO 99/61888 A3 | 12/2001 |
| 2007/0212738 | A1 | 9/2007 | Haley et al. | WO | WO 01/35071 A3 | 2/2002 |
| 2007/0231851 | A1 | 10/2007 | Toner et al. | WO | WO 02/12896 A1 | 2/2002 |
| 2007/0238105 | A1 | 10/2007 | Barrett et al. | WO | WO 02/28523 A2 | 4/2002 |
| 2007/0259424 | A1 | 11/2007 | Toner et al. | WO | WO 02/30562 A1 | 4/2002 |
| 2007/0264675 | A1 | 11/2007 | Toner et al. | WO | WO 02/31506 A1 | 4/2002 |
| 2007/0275402 | A1 | 11/2007 | Lo et al. | WO | WO 02/44318 A1 | 6/2002 |
| 2008/0020390 | A1 | 1/2008 | Mitchell et al. | WO | WO 02/073204 A2 | 9/2002 |
| 2008/0023399 | A1 | 1/2008 | Inglis et al. | WO | WO 03/018757 A2 | 3/2003 |
| 2008/0026390 | A1 | 1/2008 | Stoughton et al. | WO | WO 03/019141 A2 | 3/2003 |
| 2008/0038733 | A1 | 2/2008 | Bischoff et al. | WO | WO 03/020974 A2 | 3/2003 |
| 2008/0050739 | A1 | 2/2008 | Stoughton et al. | WO | WO 03/020986 A1 | 3/2003 |
| 2008/0070792 | A1 | 3/2008 | Stoughton et al. | WO | WO 03/023057 A2 | 3/2003 |
| 2008/0071076 | A1 | 3/2008 | Hahn et al. | WO | WO 03/031938 A2 | 4/2003 |
| 2008/0090239 | A1 | 4/2008 | Shoemaker et al. | WO | WO 03/035894 A2 | 5/2003 |
| 2008/0096216 | A1 | 4/2008 | Quake | WO | WO 03/035895 A2 | 5/2003 |
| 2008/0096766 | A1 | 4/2008 | Lee | WO | WO 03/044217 A2 | 5/2003 |
| 2008/0124721 | A1 | 5/2008 | Fuchs | WO | WO 03/044224 A1 | 5/2003 |
| 2008/0138809 | A1 | 6/2008 | Kapur et al. | WO | 03048295 A1 | 6/2003 |
| 2008/0153090 | A1 | 6/2008 | Lo et al. | WO | WO 03/069421 A2 | 8/2003 |
| 2008/0182261 | A1 | 7/2008 | Bianchi | WO | WO 03/018757 A3 | 9/2003 |
| 2008/0193927 | A1 | 8/2008 | Mann et al. | WO | WO 02/073204 A3 | 10/2003 |
| 2008/0213775 | A1 | 9/2008 | Brody et al. | WO | WO 03/044217 A3 | 10/2003 |
| 2008/0220422 | A1 | 9/2008 | Shoemaker et al. | WO | WO 03/031938 A3 | 11/2003 |
| 2008/0299562 | A1 | 12/2008 | Oeth et al. | WO | WO 03/093795 A2 | 11/2003 |
| 2009/0029377 | A1 | 1/2009 | Lo et al. | WO | WO 03/023057 A3 | 12/2003 |
| 2009/0087847 | A1 | 4/2009 | Lo et al. | WO | WO 03/069421 A3 | 12/2003 |
| 2009/0170113 | A1 | 7/2009 | Quake et al. | WO | WO 03/035895 A3 | 1/2004 |
| 2009/0170114 | A1 | 7/2009 | Quake et al. | WO | WO 03/035894 A3 | 3/2004 |
| 2009/0215042 | A1* | 8/2009 | Sella-Tavor et al. ............... 435/6 | WO | WO 2004/025251 A2 | 3/2004 |
| 2009/0280492 | A1 | 11/2009 | Stoughton et al. | WO | WO 03/019141 A3 | 4/2004 |
| 2009/0291443 | A1 | 11/2009 | Stoughton et al. | WO | WO 2004/029221 A2 | 4/2004 |
| 2009/0307181 | A1* | 12/2009 | Colby et al. .................... 706/54 | WO | WO 2004/029221 A3 | 5/2004 |
| 2010/0093835 | A1* | 4/2010 | McSwiggen et al. ....... 514/44 A | WO | WO 2004/037374 A2 | 5/2004 |
| | | | | WO | WO 2004/044236 A1 | 5/2004 |
| FOREIGN PATENT DOCUMENTS | | | | WO | WO 2004/056978 A1 | 7/2004 |
| EP | 0405972 B1 | | 5/1999 | WO | 2004065629 A1 | 8/2004 |
| EP | 1262776 A2 | | 12/2002 | WO | WO 2004/076643 A2 | 9/2004 |
| EP | 0994963 B1 | | 5/2003 | WO | WO 03/093795 A3 | 10/2004 |
| EP | 0970365 B1 | | 10/2003 | WO | WO 2004/037374 A3 | 10/2004 |
| EP | 783694 B1 | | 11/2003 | WO | WO 2004/088310 A1 | 10/2004 |
| EP | 1262776 A3 | | 1/2004 | WO | WO 2004/025251 A3 | 11/2004 |
| EP | 1388013 B1 | | 2/2004 | WO | WO 2004/101762 A2 | 11/2004 |
| EP | 0920627 B1 | | 5/2004 | WO | WO 2004/113877 A1 | 12/2004 |
| EP | 1418003 A1 | | 5/2004 | WO | WO 2004/101762 A3 | 2/2005 |
| EP | 0739240 B1 | | 6/2004 | WO | WO 2005/028663 A2 | 3/2005 |
| EP | 1462800 A1 | | 9/2004 | WO | WO 2005/042713 A2 | 5/2005 |
| EP | 0919812 B1 | | 10/2004 | WO | WO 2005/043121 A2 | 5/2005 |
| EP | 1561507 A1 | | 8/2005 | WO | WO 2005/047529 A1 | 5/2005 |
| EP | 1409727 B1 | | 11/2005 | WO | WO 2005/047532 A1 | 5/2005 |
| EP | 1272668 B1 | | 2/2007 | WO | WO 2005/023091 A3 | 6/2005 |
| EP | 1754788 A2 | | 2/2007 | WO | WO 2005/049168 A2 | 6/2005 |
| EP | 1757694 A2 | | 2/2007 | WO | WO 2005/058937 A2 | 6/2005 |
| EP | 1409745 B1 | | 4/2007 | WO | WO 2005/061075 A1 | 7/2005 |
| EP | 1754788 A3 | | 4/2007 | WO | WO 2005/049168 A3 | 9/2005 |
| EP | 1770171 A1 | | 4/2007 | WO | WO 2005/084374 A2 | 9/2005 |

| | | |
|---|---|---|
| WO | WO 2005/084380 A2 | 9/2005 |
| WO | WO 2005/085476 A1 | 9/2005 |
| WO | WO 2005/085861 A2 | 9/2005 |
| WO | WO 2005/098046 A2 | 10/2005 |
| WO | WO 2005/108621 A1 | 11/2005 |
| WO | WO 2005/109238 A2 | 11/2005 |
| WO | WO 2005/028663 A3 | 12/2005 |
| WO | WO 2005/098046 A3 | 12/2005 |
| WO | WO 2005/116264 A2 | 12/2005 |
| WO | WO 2005/118852 A2 | 12/2005 |
| WO | WO 2005/121362 A2 | 12/2005 |
| WO | WO 2005/085861 A3 | 2/2006 |
| WO | WO 2006/010610 A2 | 2/2006 |
| WO | WO 2006/023563 A2 | 3/2006 |
| WO | WO 2005/121362 A3 | 4/2006 |
| WO | WO 2006/041453 A1 | 4/2006 |
| WO | WO 2006/043181 A2 | 4/2006 |
| WO | WO 2005/109238 A3 | 6/2006 |
| WO | WO 2006/010610 A3 | 6/2006 |
| WO | WO 2006/043181 A3 | 6/2006 |
| WO | WO 2006/076567 A2 | 7/2006 |
| WO | WO 2006/078470 A2 | 7/2006 |
| WO | WO 2005/043121 A3 | 8/2006 |
| WO | 2006097049 A1 | 9/2006 |
| WO | WO 2006/076567 A3 | 9/2006 |
| WO | WO 2006/078470 A3 | 9/2006 |
| WO | WO 2006/100366 A2 | 9/2006 |
| WO | WO 2005/042713 A3 | 11/2006 |
| WO | WO 2006/023563 A3 | 11/2006 |
| WO | WO 2006/120434 A1 | 11/2006 |
| WO | WO 2005/084380 A3 | 12/2006 |
| WO | WO 2005/116264 A3 | 2/2007 |
| WO | WO 2007/020081 A1 | 2/2007 |
| WO | WO 2004/076643 A3 | 3/2007 |
| WO | WO 2007/024264 A2 | 3/2007 |
| WO | WO 2007/028146 A2 | 3/2007 |
| WO | WO 2007/030949 A2 | 3/2007 |
| WO | WO 2007/033167 A2 | 3/2007 |
| WO | WO 2007/034221 A2 | 3/2007 |
| WO | WO 2007/035414 A2 | 3/2007 |
| WO | WO 2007/024264 A3 | 4/2007 |
| WO | WO 2007/036025 A1 | 4/2007 |
| WO | WO 2007/038264 A2 | 4/2007 |
| WO | WO 2007/041610 A2 | 4/2007 |
| WO | WO 2007/044690 A2 | 4/2007 |
| WO | WO 2007/048076 A2 | 4/2007 |
| WO | WO 2007/030949 A3 | 5/2007 |
| WO | WO 2007/034221 A3 | 5/2007 |
| WO | WO 2007/050495 A2 | 5/2007 |
| WO | WO 2007/053142 A1 | 5/2007 |
| WO | WO 2007/053648 A2 | 5/2007 |
| WO | WO 2007/053785 A2 | 5/2007 |
| WO | WO 2007/059430 A2 | 5/2007 |
| WO | WO 2007/062222 A2 | 5/2007 |
| WO | WO 2005/058937 A3 | 6/2007 |
| WO | WO 2007/067734 A2 | 6/2007 |
| WO | WO 2007/048076 A3 | 7/2007 |
| WO | WO 2007/053648 A3 | 7/2007 |
| WO | WO 2007/075879 A2 | 7/2007 |
| WO | WO 2007/076989 A1 | 7/2007 |
| WO | WO 2007/079229 A2 | 7/2007 |
| WO | WO 2007/079250 A2 | 7/2007 |
| WO | WO 2007/080583 A2 | 7/2007 |
| WO | WO 2007/082144 A2 | 7/2007 |
| WO | WO 2007/082154 A2 | 7/2007 |
| WO | WO 2007/082379 A2 | 7/2007 |
| WO | WO 2007/050495 A3 | 8/2007 |
| WO | WO 2007/075879 A3 | 8/2007 |
| WO | WO 2007/087612 A2 | 8/2007 |
| WO | WO 2007/089880 A2 | 8/2007 |
| WO | WO 2007/089911 A2 | 8/2007 |
| WO | WO 2007/090670 A1 | 8/2007 |
| WO | WO 2007/092713 A2 | 8/2007 |
| WO | WO 2007/098484 A2 | 8/2007 |
| WO | WO 2006/100366 A3 | 9/2007 |
| WO | WO 2007/100684 A2 | 9/2007 |
| WO | WO 2007/101609 A1 | 9/2007 |
| WO | WO 2007/033167 A3 | 10/2007 |
| WO | WO 2007/038264 A3 | 10/2007 |
| WO | WO 2007/044690 A3 | 10/2007 |
| WO | WO 2007/053785 A3 | 10/2007 |
| WO | WO 2007/059430 A3 | 10/2007 |
| WO | WO 2005/084374 A3 | 11/2007 |
| WO | WO 2007/035414 A3 | 11/2007 |
| WO | WO 2007/044091 A3 | 11/2007 |
| WO | WO 2007/089880 A3 | 11/2007 |
| WO | WO 2007/126938 A2 | 11/2007 |
| WO | WO 2007/132166 A2 | 11/2007 |
| WO | WO 2007/132167 A2 | 11/2007 |
| WO | WO 2007/082379 A3 | 12/2007 |
| WO | WO 2007/098484 A3 | 12/2007 |
| WO | WO 2007/062222 A3 | 1/2008 |
| WO | WO 2007/100684 A3 | 1/2008 |
| WO | WO 2007/075836 A3 | 2/2008 |
| WO | WO 2008/017871 A1 | 2/2008 |
| WO | WO 2007/089911 A3 | 5/2008 |
| WO | WO 2007/028146 A3 | 6/2008 |
| WO | WO 2007/067734 A3 | 8/2008 |
| WO | WO 2007/126938 A3 | 10/2008 |
| WO | WO 2007/082154 A3 | 11/2008 |
| WO | WO 2007/087612 A3 | 11/2008 |
| WO | WO 2007/082144 A3 | 12/2008 |
| WO | WO 2007/092713 A3 | 12/2008 |
| WO | 2009013492 A1 | 1/2009 |
| WO | 2009013496 A1 | 1/2009 |
| WO | WO 2007/079229 A3 | 1/2009 |
| WO | WO 2007/080583 A3 | 2/2009 |
| WO | WO 2007/079250 A3 | 3/2009 |
| WO | WO 2007/041610 A3 | 4/2009 |
| WO | WO 2009/019455 A3 | 4/2009 |

OTHER PUBLICATIONS

U.S. Appl. No. 11/825,677, filed Jul. 5, 2007, Lopez et al.
U.S. Appl. No. 11/909,959, filed Sep. 27, 2007, Duff.
U.S. Appl. No. 60/764,420, filed Feb. 2, 2005, Quake.
U.S. Appl. No. 60/949,227, filed Jul. 11, 2007, Kapur.
Adinolfi, et al. Gene Amplification to Detect Fetal Nucleated Cells in Pregnant Women. The Lancet. Aug. 5, 1989:328-329.
Adinolfi, et al. Rapid detection of aneuploidies by microsatellite and the quantitative fluorescent polymerase chain reaction. Prenat. Diagn. 1997; 17(13):1299-311.
Adinolfi, M. On a Non-Invasive Approach to Prenatel Diagnosis based on the detection of Fetal Nucleated Cells in Maternal Blood Samples. Prenatal Diagnosis. 1991;11:799-804.
Ahn, et al. A fully integrated micromachined magnetic particle separator. Journal of Microelectromechanical Systems. 1996; 5(3):151-158.
Andrews, et al. Enrichment of fetal nucleated cells from maternal blood: model test system using cord blood. Prenatal Diagnosis. 1995; 15:913-919.
Applicant's Amendment and Response dated Jun. 17, 2009 to Non-Final Office Action of Jan. 28, 2009 re U.S. Appl. No. 11/701,686.
Ariga, et al. Kinetics of fetal cellular and cell-free DNA in the maternal circulation during and after pregnancy: implications for noninvasive prenatal diagnosis. Transfusion. 2001; 41:1524-1530.
Arnould, et al. Agreement between chromogenic in situ hybridisation (CISH) and FISH in the determination of HER2 status in breast cancer. Br J Cancer. 2003; 88(10):1587-91. (Abstract only).
Babochkina, et al. Direct detection of fetal cells in maternal blood: a reappraisal using a combination of two different Y chromosome-specific FISH probes and a single X chromosome-specific probe. Arch Gynecol Obstet. Dec. 2005;273(3):166-9. (Abstract only).
Babochkina, T. I. Ph. D. Dissertation—Fetal cells in maternal circulation: Fetal cell separation and FISH analysis. University of Basel, Switzerland. Dec. 8, 2005. (123 pages).
Balko, et al. Gene expression patterns that predict sensitivity to epidermal growth factor receptor tyrosine kinase inhibitors in lung cancer cell lines and human lung tumors. BMC Genomics. Nov. 10, 2006;7:289 (14 pages).
Barrett, et al. Comparative genomic hybridization using oligonucleotide microarrays and total genomic DNA. Proc Natl Acad Sci U S A. 2004; 101(51):17765-70.
Basch, et al. Cell separation using positive immunoselective techniques. Journal of Immunological Methods. 1983;56:269-280.

Bauer, J. Advances in cell separation: recent developments in counterflow centrifugal elutriation and continuous flow cell separation. Journal of Chromatography. 1999;722:55-69.

Becker, et al. Fabrication of Microstructures With High Aspect Ratios and Great Structural Heights by Synchrotron Radiation Lithography, Galvanoforming, and Plastic Moulding (LIGA Process). Microelectronic Engineering. 1986;4:35-56.

Becker, et al. Planar quartz chips with submicron channels for two-dimensional capillary electrophoresis applications. J. Micromech Microeng.1998;9:24-28.

Beebe et al. Functional Hydrogel Structures for Autonomous Flow Control Inside Microfluidic Channels. Nature. 2000; 404:588-590.

Bennett, et al. Toward the 1,000 dollars human genome. Pharmacogenomics. 2005; 6(4):373-82.

Berenson, et al. Cellular Immunoabsorption Using Monoclonal Antibodies. Transplantation.1984;38:136-143.

Berenson, et al. Positive selection of viable cell populations using avidin-biotin immunoadsorption. Journal of Immunological Methods. 1986;91:11-19.

Berg, H. C. Random Walks in Biology, Ch. 4. Princeton University Press. Princeton, NJ. 1993. pp. 48-64.

Berger, et al. Design of a microfabricated magnetic cell separator. Electrophoresis. Oct. 2001;22(18):3883-92.

Bianchi, et al. Isolation of fetal DNA from nucleated erythrocytes in maternal blood. Medical Sciences. 1990;87:3279-3283.

Bianchi, et al. Demonstration of fetal gene sequences in nucleated erythrocytes isolated from maternal blood. American Journal of Human Genetics. 1989;45:A252.

Bianchi, et al. Fetal gender and aneuploidy detection using fetal cells in maternal blood: analysis of NIFTY I data Prenatal Diagnosis. 2002; 22:609-615.

Bianchi, et al. Fetal nucleated erythrocytes (FNRBC) in maternal blood: erythroid-specific antibodies improve detection. The American Journal of Human Genetics. Oct. 1992. Supplemental to vol. 51, No. 4: 996.

Bianchi, et al. Isolation of Male Fetal DNA from Nucleated Erythrocytes (NRBC) in Maternal Blood. The American Pediatric Society and Society for Pediatric Research, Mar. 1989; 818:139A.

Bianchi, et al. Possible Effects of Gestational Age on the Detection of Fetal Nucleated Erythrocytes in Maternal Blood. Prenatal Diagnosis. 1991;11:523-528.

Bignell, et al. High-resolution analysis of DNA copy number using oligonucleotide microarrays. Genome Research. 2004; 14(2):287-295.

Blake, et al. Assessment of multiplex fluorescent PCR for screening single cells for trisomy 21 and single gene defects. Mol. Hum. Reprod. 1999; 5(12):1166-75.

Bode, et al. Mutations in the tyrosine kinase domain of the EGFR gene are rare in synovial sarcoma. Mod Pathol. Apr. 2006;19(4):541-7.

Boehm, et al. Analysis of Defective *Dystrophin* Genes with cDNA Probes: Rearrangement Polymorphism, Detection of Deletions in Carrier Females, and Lower Than Expected Frequency of Carrier Mothers in Isolated Cases of Delections. Pediatric Research. Apr. 1989: 139A-820.

Bohmer, et al. Differential Development of Fetal and Adult Haemoglobin Profiles in Colony Culture: Isolation of Fetal Nucleated Red Cells by Two-Colour Fluorescence Labelling. Br. J. Haematol. 1998; 103:351-60.

Brison, et al. General Method for Cloning Amplified DNA by Differential Screening with Genomic Probes. Molecular and Cellular Biology. 1982;2:578-587.

Brody, et al. Deformation and Flow of Red Blood Cells in a Synthetic Lattice: Evidence for an Active Cytoskeleton. Biophys. J. 68:2224-2232 (1995).

Caggana, M. Microfabricated devices for sparse cell isolation. CNF Project #905-00. Cornell NanoScale Facility. 2003; pp. 38-39.

Caggana, M. Microfabricated devices for sparse cell isolation. CNF Project #905-00. Cornell NanoScale Facility. 2004-2005; pp. 32-33.

Calin, et al. A microRNA signature Associated with prognosis and progression in chronic lymphocytic leukemia. New England Journal of Medicine. 2005; 353:1793-1801.

Cha, The utility of an erythroblast scoring system and gender-independent short tandem repeat (STR) analysis for the detection of aneuploid fetal cells in maternal blood. Prenat. Diagn. 2005; 25(7):586-91.

Chamberlain, et al. Deletion screening of the Duchenne muscular dystrophy locus via multiplex DNA amplification. Nucleic Acids Research. 1988;16:11141-11156.

Chan, et al. Size distributions of maternal and fetal DNA in maternal plasma. Clin Chem. Jan. 2004;50(1):88-92.

Chang, et al. Biomimetic technique for adhesion-based collection and separation of cells in a microfluidic channel. Lab Chip. 2005; 5:64-73.

Cheung, et al. Development and validation of a CGH microarray for clinical cytogenetic diagnosis. Genet Med. 2005; 7(6):422-32.

Chiu, et al. Patterned Deposition of Cells and Proteins Onto Surfaces by Using Three-Dimensional Microfluidic Systems. Proceedings of the National Academy of Sciences of the United States of America. 2000; pp. 2408-2413.

Choesmel, et al. Enrichment methods to detect bone marrow micrometastases in breast carcinoma patients: clinical relevance. Breast Cancer Res. 2004;6(5):R556-569.

Choolani, et al. Characterization of First Trimester Fetal Erythroblasts for Non-Invasive Prenatal Diagnosis. Mol. Hum. Reprod. 2003; 9:227-35.

Chou, et al. A Microfabricated Device for Sizing and Sorting DNA Molecules. Proceedings of the National Academy of Sciences of the United States of America. 1999; pp. 11-13.

Chou, et al. Sorting by diffusion: An asymmetric obstacle course for continuous molecular separation. PNAS. 1999; 96(24):13762-13765.

Christel, et al. High aspect ratio silicon microstructures for nucleic acid extraction. Solid-state sensor and actuator workshop. Hilton Head, SC. Jun. 8-11, 1998; 363-366.

Christensen, et al. Fetal Cells in Maternal Blood: A Comparison of Methods for Cell Isolation and Identification. Fetal Diagn. Ther. 2005; 20:106-12.

Chueh, et al. Prenatal Diagnosis Using Fetal Cells from the Maternal Circulation. West J. Med. 159:308-311 (1993).

Chueh, et al. Prenatal Diagnosis Using Fetal Cells in the Maternal Circulation. Seminars in Perinatology. 1990;14:471-482.

Chueh, et al. The search for fetal cells in the maternal circulation. J Perinat Med. 1991;19:411-420.

Cirigliano, et al. "Clinical application of multiplex quantitative fluorescent polymerase chain reaction (QF-PCR) for the rapid prenatal detection of common chromosome aneuploidies," Molecular Human Reproduction, 2001, vol. 7, No. 10, 1001-1006.

Clayton, et al. Fetal Erythrocytes in the Maternal Circulation of Pregnant Women. Obstetrics and Gynecology. 1964;23:915-919.

Collarini, et al. Comparison of methods for erythroblast selection: application to selecting fetal erythroblasts from maternal blood. Cytometry. 2001; 45:267-276.

Cremer, et al. Detection of chromosome aberrations in human interphase nucleus by visualization of specific target DNAs with radioactive and non-radioactive in situ hybridization techniques: diagnosis of trisomy 18 with probe L1.84. Human Genetics. 1986;74:346-352.

Cremer, et al. Detection of chromosome aberaations in metaphase and interphase tumor cells by in situ hybridization using chromosome-specific library probes. Human Genetics.1988;80:235-246.

Das, et al. Dielectrophoretic segregation of different human cell types on microscope slides. Anal. Chem. 2005; 77:2708-2719.

De Alba, et al. Prenatal diagnosis on fetal cells obtained from maternal peripheral blood: report of 66 cases. Prenat Diagn. Oct. 1999;19(10):934-40.

De Kretser, et al. The Separation of Cell Populations using Monoclonal Antibodies attached to Sepharose. Tissue Antigens. 1980;16:317-325.

Delamarche, et al. Microfluidic Networks for Chemical Patterning of Substrates: Design and Application to Bioassays. Journal of the American Chemical Society. 1998; 120:500-508.

Delamarche, et al. Patterned Delivery of Immunoglobulins to Surfaces Using Microfluidic Networks. Science. 1997; 276:779-781.

Deng, et al. Enumeration and microfluidic chip separation of circulating fetal cells early in pregnancy from maternal blood. American Journal of Obstetrics & Gynecology. Dec. 2008 (vol. 199, Issue 6, p. S134).

Deshmukh, et al. Continuous Micromixer With Pulsatile Micropumps. Solid-State Sensor and Actuator Workshop. Hilton Head Island, South Carolina; Jun. 4-8, 2000:73-76.

Di Naro, et al. Prenatal diagnosis of beta-thalassaemia using fetal erythroblasts enriched from maternal blood by a novel gradient. Mol Hum Reprod. 2000; 6(6):571-4.

Dilella, et al. Screening for Phenylketonuria Mutations by DNA Amplification with the Polymerase Chain Reaction. The Lancet. Mar. 5, 1988:497-499.

Doyle, et al. Self-Assembled Magnetic Matrices for DNA Separation Chips. Science 295:2237 (2002).

Eigen, et al. Sorting Single Molecules: Application to Diagnostics and Evolutionary Biotechnology. Proceedings of the National Academy of Sciences of the United States of America. 1994; 91:5740-5747.

Emanuel, et al. Amplification of Specific Gene Products from Human Serum. GATA, 1993, vol. 10, No. 6, 144-146.

European search report dated Nov. 9, 2009 for Application No. 7784442.1.

European search report dated Dec. 21, 2009 for Application No. 07798579.4.

European search report dated Dec. 22, 2009 for Appllication No. 07798580.2.

European search report dated Dec. 22, 2009 for Application No. 0778444.7.

European Search Report dated Jul. 31, 2009 for EP07763674.4.

Final Office Action dated Sep. 11, 2009 issued in U.S. Appl. No. 11/701,686.

Non-Final Office Action dated Jan. 28, 2009 issued in U.S. Appl. No. 11/701,686.

Falcidia, et al. Fetal Cells in maternal blood: a six-fold increase in women who have undergone mniocentesis and carry a fetus with Down syndrome: a multicenter study. Neuropediatrics. 2004; 35(6):321-324. (Abstract only).

Fan, et al. Highly parallel SNP genotyping. Cold Spring Harb. Symp. Quant. Biol. 2003; 68:69-78.

Fan, et al. Single cell degenerate oligonucleotide primer-PCR and comparative genomic hybridization with modified control reference. Journal of Ahejian University—Science A. 2001; 2(3):318-321.

Farber, et al. Demonstration of spontaneous XX/XY chimerism by DNA fingerprinting. Human Genetics. 1989;82:197-198.

Farooqui, et al. Microfabrication of Submicron Nozzles in Silicon Nitride. Journal of Microelectromechanical Systems. 1992; 1(2):86-88.

Fiedler, et al. Dielectrophoretic Sorting of Particles and Cells in a Microsystem. Analytical Chemistry. 1998; pp. 1909-1915.

Findlay, et al. Using MF-PCR to diagnose multiple defects from single cells: implications for PGD. Mol Cell Endocrinol. 2001; 183 Suppl 1:S5-12.

Freemantle, M. Downsizing Chemistry. Chemical analysis and synthesis on microchips promise a variety of potential benefits. Chemical & Engineering News. 1999; pp. 27-36.

Fu, et al. An integrated miscrofabricated cell sorter. Anal Chem. 2002;74:2451-2457.

Fu, et al. A Microfabricated Fluorescence-Activated Cell Sorter. Nature Biotechnology.1999; 17:1109-1111.

Fuhr, et al. Biological Application of Microstructures. Topics in Current Chemistry. 1997; 194:83-116.

Furdui, et al. Immunomagnetic T cell capture from blood for PCR analysis using microfluidic systems. Lab Chip. Dec. 2004;4(6):614-8.

Ganshirt-Ahlert, et al. Magnetic cell sorting and the transferrin receptor as potential means of prenatal diagnosis from maternal blood. Am J Obstet Gynecol. 1992;166:1350-1355.

Ganshirt-Ahlert, et al. Noninvasive prenatal diagnosis: Triple density gradient, magnetic activated cell sorting and FISH prove to be an efficient and reproducible method for detection of fetal aneuploidies from maternal blood. The American Journal of Human Genetics. Oct. 1992. Supplemental to vol. 51, No. 4: 182.

GenomeWeb. Immunicon inks biomarker assay, lab services deal with merck serona. Available at C:\Documents and Settings\fc3\Local Settings\Temporary InternetFiles\OLK35E\141896-1.htm. Accessed on Sep. 11, 2007.

Ghia, et al. Ordering of human bone marrow B lymphocyte precursors by single-cell polymerase chain reaction analyses of the rearrangement status of the immunoglobulin H and L chain gene loci. J Exp Med. Dec. 1, 1996;184(6):2217-29.

Giddings, J. C. Chemistry 'Eddy' Diffusion in Chromatography. Nature. 1959;184:357-358.

Giddings, J. C. Field-Flow Fractionation: Analysis of Macromolecular, Colloidal, and Particulate Materials. Science. 1993;260:1456-1465.

Gonzalez, et al. Multiple displacement amplification as a pre-polymerase chain reaction (pre-PCR) to process difficult to amplify samples and low copy number sequences from natural environments. Environ Microbiol. 2005; 7(7):1024-8.

Graham. Efficiency comparison of two preparative mechanisms for magnetic separation of erthrocytes from whole blood. J. Appl. Phys. 1981; 52:2578-2580.

Greaves, et al. Expression of the OKT Monoclonal Antibody Defined Antigenic Determinants in Malignancy. Int. J. Immunopharmac. 1981;3:283-299.

Guetta, et al. Analysis of fetal blood cells in the maternal circulation: challenges, ongoing efforts, and potential solutions. Stem Cells Dev. 2004;13(1):93-9.

Gunderson, et al. A genome-wide scalable SNP genotyping assay using microarray technology. Nat Genet. 2005; 37(5):549-54.

Hahn, et al. Current applications of single-cell PCR. Cell. Mol. Life Sci. 2000; 57(1):96-105. Review.

Hamabe, et al. Molecular study of the Prader-Willi syndrome: deletion, RFLP, and phenotype analyses of 50 patients. Am J Med Genet. Oct. 1, 1991;41(1):54-63.

Han, et al. Separation of Long DNA Molecules in a Microfabricated Entropic Trap Array. Science. 2000;288:1026-1029.

Hardenbol, et al. Highly multiplexed molecular inversion probe genotyping: over 10,000 targeted SNPs genotyped in a single tube assay. Genome Res. 2005;15(2):269-75.

Hardenbol, et al. Multiplexed genotyping with sequence-tagged molecular inversion probes. Nat. Biotechnol. 2003; 21(6):673-8.

Hartmann, et al. Gene expression profiling of single cells on large-scale oligonucleotide arrays. Nucleic Acids Research. 2006; 34(21): e143. (11 pages).

Herzenberg, et al. Fetal cells in the blood of pregnant women: Detection and enrichment by flourescence-activated cell sorting. Proc. Natl. Acad. Sci. 1979;76:1453-1455.

Holzgreve, et al. Fetal Cells in the Maternal Circulation. Journal of Reproductive Medicine. 1992;37:410-418.

Hong, et al. A nanoliter-scale nucleic acid processor with parallel architecture. Nat. Biotechnol. 2004; 22(4):435-9.

Hosono, et al. Unbiased whole-genome amplification directly from clinical samples. Genome Res. May 2003;13(5):954-64.

Hromadnikova, et al. "Quantitative analysis of DNA levels in maternal plasma in normal and Down syndrome pregnancies." Bio Med Central, May 2002, 1-5.

Huang, et al. A DNA prism for high-speed continuous fractionation of large DNA molecules. Nature Biotechnology. 2002;20:1048-1051.

Huang, et al. Continuous Particle Separation Through Deterministic Lateral Displacement. Science 304:987-90 (2004).

Huang, et al. Electric Manipulation of Bioparticles and Macromoledules on Microfabricated Electrodes. Analytical Chemistry. 2001; pp. 1549-1559.

Huang, et al. Role of Molecular Size in Ratchet Fractionation. 2002; 89(17):178301-1-178301-4.

Huh, et al. Gravity-driven microhydrodynamics-based cell sorter (microHYCS) for rapid, inexpensive, and efficient cell separation and size-profiling. 2nd Annual International IEEE-EMBS Special Topic Conference on Microtechnology in Medicine and Biology. Madison, Wisconsin USA; May 2-4, 2002:466-469.

Hviid T. In-Cell PCT method for specific genotyping of genomic DNA from one individual in a micture of cells from two individuals:

a model study with specific relevance to prenatal diagnosis based on fetal cells in maternal blood. Molecular Diagnostics and Genetics. 2002; 48:2115-2123.

Hviid, T. In-cell polymerase chain reaction: strategy and diagnostic applications. Methods Mol Biol. 2006;336:45-58.

International search report and written opinion dated Mar. 16, 2010 for PCT Application No. U52009/57136.

International Search Report and Written Opinion dated Sep. 18, 2008 for PCT/US2007/003209.

International search report dated Jan. 16, 2008 for PCT Application No. US2007/71247.

International search report dated Jan. 25, 2008 for PCT Application No. US2007/71250.

International search report dated Nov. 15, 2007 for PCT Application No. US2007/71149.

International search report dated Nov. 26, 2007 for PCT Application No. US2007/71256.

International search report dated Feb. 25, 2008 for PCT Application No. US07/71148.

International search report dated Feb. 25, 2008 for PCT Application No. US2007/71248.

Iverson, et al. Detection and Isolation of Fetal Cells From Maternal Blood Using the Flourescence-Activated Cell Sorter (FACS). Prenatal Diagnosis 1981;1:61-73.

Jan, et al. Fetal Erythrocytes Detected and Separated from Maternal Blood by Electronic Fluorescent Cell Sorter. Texas Rep Biol Med. 1973;31:575.

Jeon, et al. Generation of Solution and surface Gradients Using Microfluidic Systems. Langmuir. 2000, pp. 8311-8316.

Jiang, et al. Genome amplification of single sperm using multiple displacement amplification. Nucleic Acids Res. 2005; 33(10):e91. (9 pages).

Kamholz, et al. Quantitative Analysis of Molecular Interaction in a Microfluidic Channel: the T-Sensor. Analytical Chemistry. 1999; pp. 5340-5347.

Kan, et al. Concentration of Fetal Red Blood Cells From a Mixture of Maternal and Fetal Blood by Anti-i Serum—An Aid to Prenatal Diagnosis of Hemoglobinopathies. Blood. 1974; 43:411-415.

Kasakov, et al. Extracellular DNA in the blood of pregnant women. Tsitologiia. 1995;37(3):232-6. (English translation only).

Kenis, et al. Microfabrication Inside Capillaries Using Multiphase Laminar Flow Patterning. Science. 1999; 285:83-85.

Kim, et al. Polymer microstructures formed by moulding in capillaries. Nature. 1995;376:581-584.

Kimura, et al. The DYRK1A gene, encoded in chromosome 21 Down syndrome critical region, bridges between (β-amyloid production and tau phosphorylation in Alzheimer disease. Human Molecular Genetics, Nov. 29, 2008, vol. 16, No. 1, 15-23.

Klein, C. A. Single cell amplification methods for the study of cancer and cellular ageing. Mech. Ageing Dev. 2005; 126(1):147-51.

Klein, et al. Comparative genomic hybridization, loss of heterozygosity, and DNA sequence analysis of single cells. Proc Natl Acad Sci U S A. 1999; 96(8):4494-9.

Kogan, et al. An Improved Method for Prenatal Diagnosis of Genetic Diseases by Analysis of Amplified DNA Sequences, Application to Hemophilia A. The New England Journal of Medicine. 1987;317:985-990.

Korenberg, et al. Down syndrome phenotypes: the consequences of chromosomal imbalance. PNAS 1994; 91:4997-5001.

Krabchi, et al. Quantification of all fetal nucleated cells in maternal blood between the 18th and 22nd weeks of pregnancy using molecular cytogenic techniques. Clin. Genet. 2001; 60:145-150.

Krivacic, et al. A rare-cell detector for cancer. PNAS. 2004;101:10501-10504.

Kulozik, et al. Fetal Cell in the Maternal Circulation: Detection by Direct AFP-Immunoflourescence. Human Genetics. 1982;62:221-224.

Leutwyler, K. Mapping Chromosome 21. Available at http://www.scientificamerican.com/article.cfm?id=mapping-chromosome-21. Accessed Feb. 3, 2010.

Levett, et al. A large-scale evaluation of amnio-PCR for the rapid prenatal diagnosis of fetal trisomy. Ultrasound Obstet Gynecol. 2001; 17(2):115-8.

Li, et al. Transport, Manipulation, and Reaction of Biological Cells On-Chip Using Electrokinetic Effects. Analytical Chemistry., 1997; pp. 1564-1568.

Li, et al. Amplification and analysis of DNA sequences in single human sperm and diploid cells. Nature. 1988;335:414-417.

Lichter, et al. Delineation of individual human chromosomes in metaphase and interphase cells by in situ suppression hyridization using recombinant DNA libraries. Hum Genet. 1988;80:224-234.

Liu, et al. Development and validation of a T7 based linear amplification for genomic DNA. BMC Genomics. 2003; 4(1):19. (11 pages).

Loken, et al. Flow Cytometric Analysis of Human Bone Marrow: I. Normal Erythroid Development. Blood. 1987;69:255-263.

Mahr, et al. Fluorescence in situ hybridization of fetal nucleated red blood cells. The American Journal of Human Genetics. Oct. 1992. Supplemental to vol. 51, No. 4: 1621.

Maloney et al. "Microchimerism of maternal origin persists into adult life," J. Clin. Invest. 104:41-47 (1999).

Margulies, et al. Genome sequencing in microfabricated high-density picolitre reactors. Nature. 2005; 437:376-80.

Martin, et al. "A method for using serum or plasma as a source of NDA for HLA typing," Human Immunology. 1992; 33:108-113.

Mavrou, et al. Identification of nucleated red blood cells in maternal circulation: A second step in screening for fetal aneuploidies and pregnancy complications. Prenat Diagn. 2007; 247:150-153.

McCabe, et al. DNA microextraction from dried blood spots on filter paper blotters: potential applications to newborn screening. Hum Genet.1987;75:213-216.

McCarley, et al. Patterning of surface-capture architectures in polymer-based microanalytical devices. In Kuther, et al. Eds. Royal Society of Chemistry Special Publication. 2005;130-132. (Abstract only).

Mehrishi, et al. Electrophoresis of cells and the biological relevance of surface charge. Electrophoresis.2002;23:1984-1994.

Melville, et al. Direct magnetic separation of red cells from whole blood. Nature. 1975; 255:706.

Mohamed, et al. A Micromachined Sparse Cell Isolation Device: Application in Prenatal Diagnostics. Nanotech 2006 vol. 2; 641-644. (Abstract only).

Mohamed, et al. Biochip for separating fetal cells from maternal circulation. J Chromatogr A. Aug. 31, 2007;1162(2):187-92.

Mohamed, et al. Development of a rare cell fractionation device: application for cancer detection. IEEE Trans Nanobioscience. 2004; 3(4): 251-6.

Moore, et al. Lymphocyte fractionation using immunomagnetic colloid and a dipole magnet flow cell sorter. J Biochem Biophys Methods. 1998;37:11-33.

Moorhead, et al. Optimal genotype determination in highly multiplexed SNP data Eur. J. Hum. Genet. 2006;14(2):207-15. (published online Nov. 23, 2005).

Mueller, et al. Isolation of fetal trophoblast cells from peripheral blood of pregnant women. The Lancet. 1990;336:197-200.

Muller, et al. Moderately repeated DNA sequences specific for the short arm of the human Y chromosome are present in XX makes and reduced in copy number in an XY female. 1986;14:1325-1340.

Mullis, et al. Specific Enzymatic Amplification of DNA In Vitro: The Polymerase Chain Reaction. Cold Spring Harbor Symposia on Quantitative Biolgy 1986;51:263-273.

Murakami, et al. A novel single cell PCR assay: detection of human T lymphotropic virus type I DNA in lymphocytes of patients with adult T cell leukemia. Leukemia. Oct. 1998;12(10):1645-50.

Murthy, et al. Assessment of multiple displacement amplification for polymorphism discovery and haplotype determination at a highly polymorphic locus, MC1R. Hum. Mutat. 2005; 26(2):145-52.

Nagrath, et al. Isolation of rare circulating tumour cells in cancer patients by microchip technology. Nature. 2007; 450: 1235-1241 (with Supplemental pp. 1-10).

Nelson, et al. Genotyping Fetal DNA by Non-Invasive Means: Extraction From Maternal Plasma. Vox Sang. 2001;80:112-116.

Newcombe, R. G. Two-sided confidence intervals for the single proportion: comparison of seven methods. Statistics in Medicine. 1998; 17:857-872.

Oakey et al. Laminar Flow-Based Separations at the Microscale. Biotechnology Progress. 2002; pp. 1439-1442.

Office action dated Nov. 3, 2009 for U.S. Appl. No. 11/763,133.

Office action dated Dec. 1, 2009 for U.S. Appl. No. 11/763,426.
Office action dated Mar. 11, 2010 for U.S. Appl. No. 11/763,245.
Office action dated Mar. 4, 2009 for U.S. Appl. No. 11/228,454.
Office action dated May 4, 2009 for U.S. Appl. No. 11/763,431.
Olson, et al. An In Situ Flow Cytometer for the Optical Analysis of Individual Particles in Seawater. Available at http://www.whoi.edu/science/B/Olsonlab/insitu2001.htm. Accessed Apr. 24, 2006.
Oosterwijk, et al. Prenatal diagnosis of trisomy 13 on fetal cells obtained from maternal blood after minor enrichment. Prenat Diagn. 1998;18(10):1082-5.
Owen, et al. High gradient magnetic separation of erythrocytes. Biophys. J. 1978; 22:171-178.
Pallavicini, et al. Analysis of fetal cells sorted from maternal blood using fluorescence in situ hybridization. The American Journal of Human Genetics. Oct. 1992. Supplemental to vol. 51, No. 4: 1031.
Parano, et al. Fetal Nucleated red blood cell counts in peripheral blood of mothers bearing Down Syndrome fetus. Neuropediatrics. 2001; 32(3):147-149. (Abstract only).
Parano, et al. Noninvasive Prenatal Diagnosis of Chromosomal Aneuploidies by Isolation and Analysis of Fetal Cells from Maternal Blood. Am. J. Med. Genet. 101:262-7 (2001).
Paterlini-Brechot, et al. Circulating tumor cells (CTC) detection: Clinical impact and future directions. Cancer Letter. 2007. (In press, 25 pages.) Available at www.sciencedirect.com.
Paul, et al. Single-molecule dilution and multiple displacement amplification for molecular haplotyping. Biotechniques. 2005; 38(4):553-4, 556, 558-9.
Pawlik, et al. Prodrug Bioactivation and Oncolysis of Diffuse Liver Metastases by a Herpes Simplex Virus 1 Mutant that Expresses the CYP2B1 Transgene. Cancer. 2002;95:1171-81.
Peixoto, et al. Quantification of multiple gene expression in individual cells. Genome Res. Oct. 2004;14(10A):1938-47.
Peng, et al. Real-time detection of gene expression in cancer cells using molecular beacon imaging: new strategies for cancer research. Cancer Res. 2005; 65(5):1909-17.
Petersen, et al. The Promise of Miniaturized Clinical Diagnostic Systems. IVD Technol. 4:43-49 (1998).
Pfaffl, et al. Relative expression software tool (REST) for group-wise comparison and statistical analysis of relative expression results in real-time PCR. Nucleic Acids Res. May 1, 2002;30(9):e36.
Pinkel, et al. Cytogenetic Analysis Using Quantitative, High-sensitivity, Fluorescence Hybridization. Genetics. 1986;83:2934-2938.
Pinkel, et al. Fluorescence in situ Hybridization with Human Chromosome-specific Libraries: Detection of Trisomy 21 and Translocations of Chromosome 4. Genetics.1988;85:9138-9142.
Pinkel, et al. Detection of structural chromosome abberations in metaphase in metaphase spreads and interphase nuclei by in situ hybridization high complexity probes which stain entire human chromosomes. The American Journal of Human Genetics. Sep. 1988. Supplemental to vol. 43, No. 3: 0471.
Pinzani, et al. Isolation by size of epithelial tumor cells in peripheral blood of patients with breast cancer: correlation with real-time reverse transcriptase-polymerase chain reaction results and feasibility of molecular analysis by laser microdissection. Hum Pathol. 2006; 37(6):711-8.
Pohl et al. Principle and applications of digital PCR. Expert Rev Mol Diagn. Jan. 2004;4(1):41-7.
Potti, et al. Genomic signatures to guide the use of chemotherapeutics. Nat Med. 2006; 12(11):1294-1300.
Price, et al. Prenatal Diagnosis with Fetal Cells Isolated from Maternal Blood by Multiparameter Flow Cytometry. Am. J. Obstet. Gynecol. 1991; 165:1731-7.
Prieto, et al. Isolation of fetal nucleated red blood cells from maternal blood in normal and aneuploid pregnancies. Clin Chem Lab Med. Jul. 2002;40(7):667-72.
Product literature for GEM, a system for blood testing: GEM Premier 3000. Avaiable at http://www.ilus.com/premier_gem3000_iqm. asp. Accessed Apr. 24, 2006.
Purwosunu, et al. Clinical potential for noninvasive prenatal diagnosis through detection of fetal cells in maternal blood. Taiwan J Obstet Gynecol. Mar. 2006;45(1):10-20.
Raeburn, P. Fetal Cells Isolated in Women's Blood. Associated Press (Jul. 28, 1989) [electronic version].
Rahil, et al. Rapid detection of common autosomal aneuploidies by quantitative fluorescent PCR on uncultured amniocytes, European Journal of Human Genetics, 2002, vol. 10, 462-466.
Rickman, et al. Prenatal diagnosis by array-CGH. European Journal of Medical Genetics. 2005; 48:232-240.
Rolle, et al. Increase in number of circulating disseminated epithelia cells after surgery for non-small cell lung cancer monitored by MAINTRAC is a predictor for relapse: a preliminary report. World Journal of Surgical Oncology. 2005; 9 pages.
Ruan, et al. Identification of clinically significant tumor antigens by selecting phage antibody library on tumor cells in situ using laser capture microdissection. Molecular & Cellular Proteomics. 2006; 5(12): 2364-73.
Sakhnini, et al. Magnetic behavior of human erythrocytes at different hemoglobin states. Eur Biophys J. Oct. 2001;30(6):467-70.
Samura, et al. Diagnosis of trisomy 21 in fetal nucleated erythrocytes from maternal blood by use of short tandem repeat sequences. Clin. Chem. 2001; 47(9):1622-6.
Samura, et al. Female fetal cells in maternal blood: use of DNA polymorphisms to prove origin. Hum. Genet. 2000;107(1):28-32.
Sato, et al. Individual and Mass Operation of Biological Cells Using Micromechanical Silicon Devices. Sensors and Actuators. 1990;A21-A23:948-953.
Schaefer, et al. The Clinical Relevance of Nucleated Red Blood Cells counts. Sysmex Journal International. 2000; 10(2):59-63.
Schröder, et al. Fetal Lymphocytes in the Maternal Blood. The Journal of Hematolog:Blood. 1972;39:153-162.
Sethu, et al. Continuous Flow Microfluidic Device for Rapid Erythrocyte Lysis. Anal. Chem. 76:6247-6253 (2004).
Shen, et al. High-throughput SNP genotyping on universal bead arrays. Mutat. Res. 2005; 573:70-82.
Shendure, et al. Accurate multiplex polony sequencing of an evolved bacterial genome. Science. 2005; 309:1728-32.
Sherlock, et al. Assessment of diagnostic quantitative fluorescent multiplex polymerase chain reaction assays performed on single cells. Ann. Hum. Genet. 1998; 62:9-23.
Sitar, et al. The Use of Non-Physiological Conditions to Isolate Fetal Cells from Maternal Blood. Exp. Cell. Res. 2005; 302:153-61.
Sohda, et al. The Proportion of Fetal Nucleated Red Blood Cells in Maternal Blood: Estimation by FACS Analysis. Prenat. Diagn. 1997; 17:743-52.
Stipp, D. IG Labs Licenses New Technology for Fetal Testing. The Wall Street Journal. Aug. 10, 1990:B5.
Stoecklein, et al. SCOMP is superior to degenerated oligonucleotide primed-polymerase chain reaction for global amplification of minute amounts of DNA from microdissected archival tissue samples. Am J Pathol. 2002; 161(1):43-51.
Stoughton, et al. Data-adaptive algorithms for calling alleles in repeat polymorphisms. Electrophoresis. 1997;18(1):1-5.
Sun, et al. Whole-genome amplification: relative efficiencies of the current methods. Leg Med. 2005; 7(5):279-86.
Sykes, et al. Quantitation of targets for PCR by use of limiting dilution. Biotechniques. Sep. 1992;13(3):444-9.
Tettelin, et al. The nucleotide sequence of *Saccharomyces cerevisiae* chromosome VII. Nature. May 29, 1997;387(6632 Suppl):81-4.
Thomas, et al. Specific Binding and Release of Cells from Beads Using Cleavable Tettrametric Antibody Complexes. Journal of Immunological Methods 1989;120:221-231.
Tibbe, et al. Statistical considerations for enumeration of circulating tumor cells. Cytometry A. Mar. 2007;71(3):154-62.
Toner, et al. Blood-on-a-Chip. Annu. Rev. Biomed. Eng. 7:77-103, C1-C3 (2005).
Trask, et al. Detection of DNA Sequences and Nuclei in Suspension by In Situ Hybridization and Dual Beam Flow Cytometry. Science. 1985;230:1401-1403.
Troeger, et al. Approximately half of the erythroblasts in maternal blood are of fetal origin. Mol Hum Reprod. 1999; 5(12):1162-5.
Van Raamsdonk, et al. Optimizing the detection of nascent transcripts by RNA fluorescence in situ hybridization. Nucl. Acids. Res. 2001; 29(8):e42.
Vogelstein, et al. "Digital PCR." Proc Natl. Acad Sci. USA, Aug. 1999, vol. 96., 9236-9241.

Volkmuth, et al. DNA electrophoresis in microlithographic arrays. Nature. 1992; 358:600-602.

Volkmuth, et al. Observation of Electrophoresis of Single DNA Molecules in Nanofabricated Arrays. Presentation at joint annual meeting of Biophysical Society and the American Society for Biochemistry and Molecular Biology. Feb. 9-13, 1992.

Von Eggeling, et al. Determination of the origin of single nucleated cells in maternal circulation by means of random PCR and a set of length polymorphisms. Hum Genet. Feb. 1997;99(2):266-70.

Vona, et al. Enrichment, immunomorphological, and genetic characterization of fetal cells circulating in maternal blood. Am J Pathol. Jan. 2002;160(1):51-8.

Voullaire, et al. Detection of aneuploidy in single cells using comparative genomic hybridization. Prenat Diagn. 1999; 19(9):846-51.

Vrettou, et al. Real-time PCR for single-cell genotyping in sickle cell and thalassemia syndromes as a rapid, accurate, reliable, and widely applicable protocol for preimplantation genetic diagnosis. Human Mutation. 2004; 23(5):513-21.

Wachtel, et al. Fetal Cells in the Maternal Circulation: Isolation by Multiparameter Flow Cytometry and Confirmation by Polymerase Chain Reaction. Human Reproduction. 1991;6:1466-1469.

Wang, et al. Allele quantification using molecular inversion probes (MIP). Nucleic Acids Research. 2005; 33(21); e183 (14 pages).

Wapner, et al. First-trimester screening for trisomies 21 and 18. N. Engl. J. Med. 2003; 349:1405-1413.

Warren, et al. Transcription factor profiling in individual hematopoietic progenitors by digital RT-PCR. PNAS. Nov. 21, 2006; 103(47):17807-17812.

Washizu, et al. Handling Biological Cells Utilizing a Fluid Integrated Circuit. IEEE Industry Applications Society Annual Meeting Presentations, Oct. 2-7, 1988;: 1735-40.

Washizu, et al. Handling Biological Cells Utilizing a Fluid Integrated Circuit. IEEE Transactions of Industry Applications. 1990; 26: 352-8.

Weigl, et al. Microfluidic Diffusion-Based Separation and Detection. Science. 1999; pp. 346-347.

Williams, et al. Comparison of cell separation methods to entrich the proportion of fetal cells in material blood samples. The American Journal of Human Genetics. Oct. 1992. Supplemental to vol. 51, No. 4: 1049.

Xiong, et al. "A simple, rapid, high-fidelity and cost-effective PCR-based two-step DNA synthesis method for long gene sequences," Nucleic Acids Research, Apr. 19, 2004, vol. 32, No. 12, e98.

Yang, et al. Prenatal diagnosis of trisomy 21 with fetal cells i maternal blood using comparative genomic hybridization. Fetal Diagn Ther. 2006; 21:125-133.

Yang, et al. Rapid Prenatal Diagnosis of Trisomy 21 by Real-time Quantitative Polymerase Chain Reaction with Amplification of Small Tandem Repeats and S100B in Chromosome 21. Yonsei Medical Journal, 2005, vol. 46, No. 2, 193-197.

Yu, et al. Objective Aneuploidy Detection for Fetal and Neonatal Screening Using Comparative Genomic Hybridization (CGH). Cytometry. 1997; 28(3): 191-197. (Absbract).

Zavala, et al. Genomic GC content prediction in prokaryotes from a sample of genes. Gene. Sep. 12, 2005;357(2):137-43.

Zhen, et al. Poly-FISH: a technique of repeated hybridizations that improves cytogenetic analysis of fetal cells in maternal blood. Prenat Diagn. 1998; 18(11):1181-5.

Zheng, et al. Fetal cell identifiers: results of microscope slide-based immunocytochemical studies as a function of gestational age and abnormality. Am J Obstet Gynecol. May 1999;180(5):1234-9.

Zimmerman, et al. Novel real-time quantitative PCR test for trisomy 21. Jan. 1, 2002. Clinical Chemistry, American Association for Clinical Chemistry. 48:(2) 362-363.

Zuska, P. Microtechnology Opens Doors to the Universe of Small Space, MD&DI Jan. 1997, p. 131.

Rebecca Sparkes, et al., "New Molecular Techniques for the Prenatal Detection of Chromosomal Aneuploidy," JOGC, Jul. 2008, No. 210, 617-621.

Bernhard Zimmermann, "Molecular Diagnosis in Prenatal Medicine," Ph.D. Thesis, 2004.

Jay Shendure, et al., "Next-generation DNA sequencing", Nature, 2008, 26:1135-1145.

Juliane C. Dohm, et al., "Substantial biases in ultra-short read data sets from high-throughput DNA sequencing", Nucleic Acids Research, 2008, 36: e105 doi: 10.1093\nar\gkn425.

Heng Li, et al., "Mapping short DNA sequencing reads and calling variants using mapping quality scores", Genome Research, 2008, doi: 10.1101/gr.078212.108.

Rossa W. K. Chiu, et al., "Non-invasive prenatal diagnosis of fetal chromosomal aneuploidy by massively parallel genomic sequencing of DNA in maternal plasma", PNAS, 2008, 105: 20458-20463.

Melissa J. Fullwood, et al., "Next-generation DNA sequencing of paired-end tags (PET) for transcriptome and genome analyses", Genome Research, 2009, 19: 521-532.

Y.M. Dennis Lo, et al., "Digital PCR for the molecular detection of fetal chromosomal aneuploidy," PNAS, Aug. 7, 2007, vol. 104, No. 32, 13116-13121.

Yuk-Ming Dennis Lo, "Noninvasive prenatal detection of fetal chromosomal aneuploidies by maternal plasma nucleic acid analysis: a review of the current state of the art," BJOG, 2009, vol. 116, 152-157.

H. Christina Fan, et al., "Noninvasive diagnosis of fetal aneuploidy by shotgun sequencing DNA from maternal blood," PNAS, Oct. 21, 2008, vol. 105, 16266-16271.

Fiona M. F. Lun, et al., "Microfluidics Digital PCR Reveals a Higher than Expected Fraction of Fetal DNA in Maternal Plasma," Clinical Chemistry, 2008, vol. 54, No. 10, 1664-1672.

Richard A. White III, et al., "Digital PCR provides sensitive and absolute calibration for high throughput sequencing," BMC GENOMICS, Mar. 19, 2009, 10:116.

Frank Diehl, et al., "Digital quantification of mutant DNA in cancer patients," Curr Opin Oncol, 2007, 19:36-42.

Y.-M. D. Lo, et al., "Prenatal Sex Determination by DNA Amplification from Maternal Peripheral Blood," The Lancet, Dec. 9, 1989, 1363-1365.

Y.-M. D. Lo, et al., "Detection of fetal RhD sequence from peripheral blood of sensitized RhD-negative pregnant women," British Journal of Haematology, 1994, vol. 87, 658-660.

Y. M. Dennis Lo, et al., "Presence of fetal DNA in maternal plasma and serum," The Lancet, Aug. 16, 1997, vol. 350, 485-487.

Jouni Uitto, et al., "Probing the fetal genome: progress in non-invasive prenatal diagnosis," Trends in Molecular Medicine, Aug. 2003, vol. 9, No. 8, 339-343.

Sinuhe Hahn, et al., "Prenatal Diagnosis Using Fetal Cells and Cell-Free Fetal DNA in Maternal Blood: What is Currently Feasible?" Clinical Obstetrics and Gynecology, Sep. 2002, vol. 45, No. 3, 649-656.

Barbara Pertl, et al., "Fetal DNA in Maternal Plasma: Emerging Clinical Applications," Obstetrics and Gynecology, Sep. 2001, vol. 98, No. 3, 483-490.

Leo L.M. Poon, et al., "Circulating fetal DNA in maternal plasma," Clinical Chimica Acta, 2001, vol. 313, 151-155.

Y.-M. D. Lo, et al., "Fetal DNA in Maternal Plasma," Ann. N.Y. Acad. Sci, Apr. 2000, vol. 906, 141-147.

Y.-M. D. Lo, et al., "Detection of single-copy fetal DNA sequence from maternal blood," The Lancet, Jun. 16, 1990, vol. 335, 1463-1464.

Y.M. Dennis Lo, et al., "Quantitative Analysis of Fetal NA in Maternal Plasma and Serum: Implications for Noninvasive Prenatal Diagnosis," Am J. Hum. Genet., 1998, vol. 62, 768-775.

Rossa W.K. Chiu, et al., "Effects of Blood-Processing Protocols on Fetal and Total DNA Quantification in Maternal Plasma," Clinical Chemistry, 2001, vol. 47, No. 9, 1607-1613.

Enders K.O. Ng, et al., "The Concentration of Circulating Corticotropin-releasing Hormone mRNA in Maternal Plasma Is Increased in Preeclampsia," Clinical Chemistry, 2003, vol. 49, No. 5, 727-731.

Ido Braslavsky, et al., "Sequence information can be obtained from single DNA molecules," PNAS, Apr. 2003, vol. 100, No. 7, 3960-3964.

Jun Zhu, et al., "Single Molecule Profiling of Alternative Pre-mRNA Splicing," Science, Aug. 2003, vol. 301, 836-838.

Devin Dressman, et al., "Transforming single DNA molecules into fluorescent magnetic particles for detection and enumeration of genetic variations," PNAS, Jul. 2003, vol. 100, No. 15, 8817-8822.

Eugene Y. Chan, et al., "DNA Mapping Using Microfluidic Stretching and Single-Molecule Detection of Fluorescent Site-Specific Tags," Genome Research, 2004, vol. 14, 1137-1146.

Jong Wook Hong, et al., "Molecular biology on a microfluidic chip," Journal of Physics: Condensed Matter, 2006, vol. 18, S691-S701.

Elizabeth A. Ottesen, et al., "Microfluidic Digital PCR Enables Multigene Analysis of Individual Environmental Bacteria," Science, Dec. 2006, vol. 314, 1464-1467.

Joshua S. Marcus, et al., "Parallel Picoliter RT-PCR Assays Using Microfluidics," Analytical Chemistry, Feb. 1, 2006, vol. 78, No. 3, 956-958.

Y. M. Dennis Lo, et al., "Plasma placental RNA allelic ratio permits noninvasive prenatal chromosomal aneuploidy detection," Nature Medicine, Jan. 2007, 1-6.

Joshua S. Marcus, et al., "Microfluidic Single-Cell mRNA Isolation and Analysis," American Chemical Society, Mar. 2006, p. A-F.

Y. M. Dennis Lo, et al., "Prenatal diagnosis: progress through plasma nucleic acids," Nature, Jan. 2007, vol. 8, 71-76.

Tetsuya S. Tanaka, et al., "Genome-wide expression profiling of mid-gestation placenta and embryo using a 15,000 mouse developmental cDNA microarray," PNAS, Aug. 2000, vol. 97, No. 16, 9127-9132.

"Separation of RNA & DNA by Gel Filtration Chromatography," Edvotek, 1987, 1-9.

Ying Li, et al., "Size Separation of Circulatory DNA in Maternal Plasma Permits Ready Detection of Fetal DNA Polymorphisms," 2004, Clinical Chemistry, vol. 50, No. 6, 1002-1001.

H. Christina Fan, et al., "Detection of Aneuploidy with Digital Polymerase Chain Reaction," Analytical Chemistry, Oct. 1, 2007, vol. 79, No. 19, 7576-7579.

H. Christina Fan, et al., "Microfluidic digital PCR enables rapid prenatal diagnosis of fetal aneuploidy," American Journal of Obstetrics & Gynecology, May 2009, 543e1-543-e7.

* cited by examiner

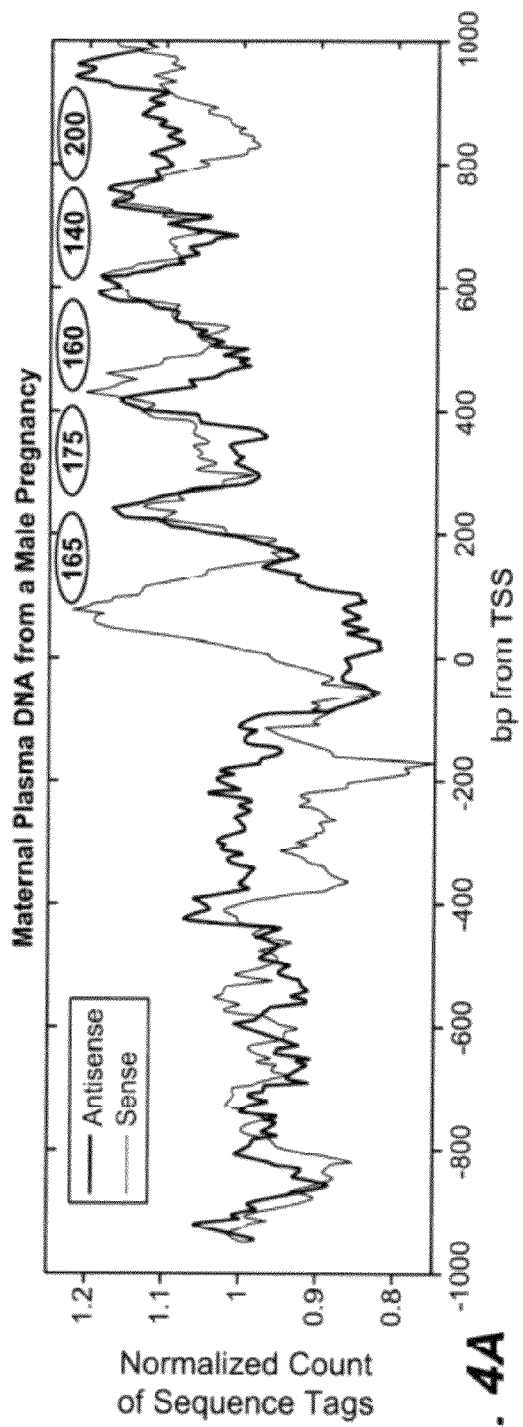
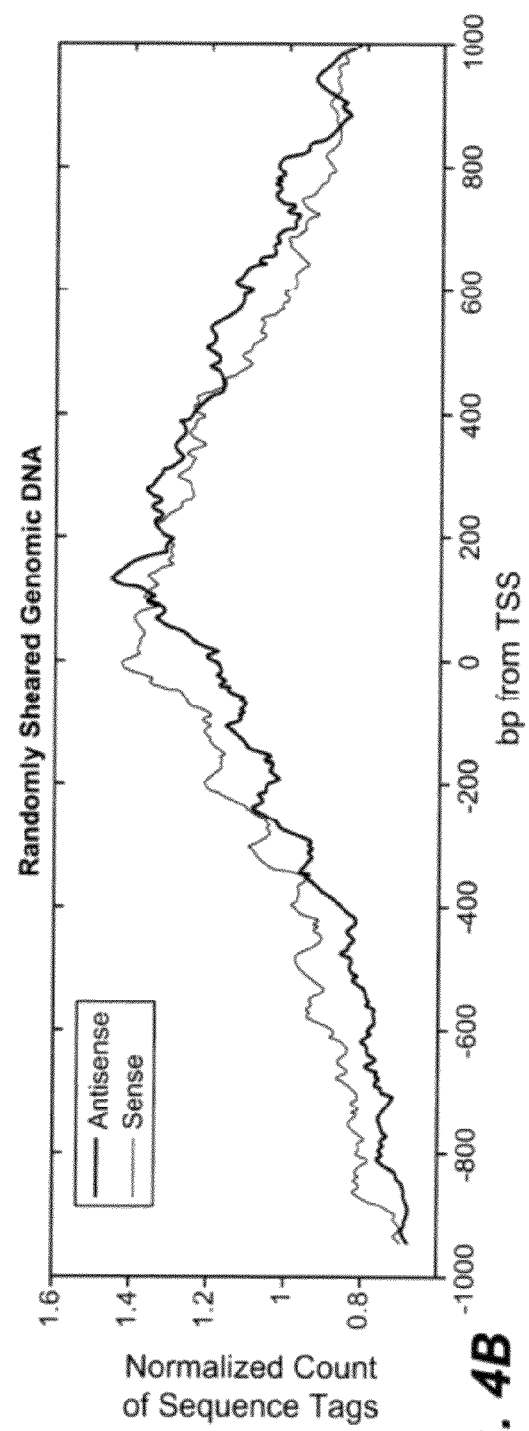
FIG. 4A
FIG. 4B

NONINVASIVE DIAGNOSIS OF FETAL ANEUPLOIDY BY SEQUENCING

CROSS-REFERENCE TO RELATED APPLICATIONS

This application claims priority from U.S. Provisional Patent Application No. 61/098,758, filed on Sep. 20, 2008, and U.S. Utility patent application Ser. No. 12/696,509, which is a divisional of U.S. application Ser. No. 12/560,708, filed Sep. 16, 2009, was filed Jan. 29, 2010, and is now U.S. Pat. No. 8,195,415, both of which are hereby incorporated by reference in their entirety.

STATEMENT OF GOVERNMENTAL SUPPORT

This invention was made with Government support under contract DP1 OD000251 awarded by the National Institutes of Health. The Government has certain rights in this invention.

REFERENCE TO SEQUENCE LISTING, COMPUTER PROGRAM, OR COMPACT DISK

Applicants submit herewith a sequence listing in an ASCII text file (3815_63_5_seq_list.txt), as provided in EFS Legal Framework Notice 20 May 2010, part I-I-1. The file was created Apr. 19, 2012 and contains 2,695 bytes. Applicants incorporate the contents of the sequence listing by reference in its entirety.

BACKGROUND OF THE INVENTION

1. Field of the Invention

The present invention relates to the field of molecular diagnostics, and more particularly to the field of prenatal genetic diagnosis.

2. Related Art

Presented below is background information on certain aspects of the present invention as they may relate to technical features referred to in the detailed description, but not necessarily described in detail. That is, certain components of the present invention may be described in greater detail in the materials discussed below. The discussion below should not be construed as an admission as to the relevance of the information to the claimed invention or the prior art effect of the material described.

Fetal aneuploidy and other chromosomal aberrations affect 9 out of 1000 live births (1). The gold standard for diagnosing chromosomal abnormalities is karyotyping of fetal cells obtained via invasive procedures such as chorionic villus sampling and amniocentesis. These procedures impose small but potentially significant risks to both the fetus and the mother (2). Non-invasive screening of fetal aneuploidy using maternal serum markers and ultrasound are available but have limited reliability (3-5). There is therefore a desire to develop non-invasive genetic tests for fetal chromosomal abnormalities.

Since the discovery of intact fetal cells in maternal blood, there has been intense interest in trying to use them as a diagnostic window into fetal genetics (6-9). While this has not yet moved into practical application (10), the later discovery that significant amounts of cell-free fetal nucleic acids also exist in maternal circulation has led to the development of new non-invasive prenatal genetic tests for a variety of traits (11, 12). However, measuring aneuploidy remains challenging due to the high background of maternal DNA; fetal DNA often constitutes <10% of total DNA in maternal cell-free plasma (13).

Recently developed methods for aneuploidy rely on detection focus on allelic variation between the mother and the fetus. Lo et al. demonstrated that allelic ratios of placental specific mRNA in maternal plasma could be used to detect trisomy 21 in certain populations (14).

Similarly, they also showed the use of allelic ratios of imprinted genes in maternal plasma DNA to diagnose trisomy 18 (15). Dhallan et al. used fetal specific alleles in maternal plasma DNA to detect trisomy 21 (16). However, these methods are limited to specific populations because they depend on the presence of genetic polymorphisms at specific loci. We and others argued that it should be possible in principle to use digital PCR to create a universal, polymorphism independent test for fetal aneuploidy using maternal plasma DNA (17-19).

An alternative method to achieve digital quantification of DNA is direct shotgun sequencing followed by mapping to the chromosome of origin and enumeration of fragments per chromosome. Recent advances in DNA sequencing technology allow massively parallel sequencing (20), producing tens of millions of short sequence tags in a single run and enabling a deeper sampling than can be achieved by digital PCR. As is known in the art, the term "sequence tag" refers to a relatively short (e.g., 15-100) nucleic acid sequence that can be used to identify a certain larger sequence, e.g., be mapped to a chromosome or genomic region or gene. These can be ESTs or expressed sequence tags obtained from mRNA.

Specific Patents and Publications

*Science* 309:1476 (2 Sep. 2005) News Focus "An Earlier Look at Baby's Genes" describes attempts to develop tests for Down Syndrome using maternal blood. Early attempts to detect Down Syndrome using fetal cells from maternal blood were called "just modestly encouraging." The report also describes work by Dennis Lo to detect the Rh gene in a fetus where it is absent in the mother. Other mutations passed on from the father have reportedly been detected as well, such as cystic fibrosis, beta-thalassemia, a type of dwarfism and Huntington's disease. However, these results have not always been reproducible.

Venter et al., "The sequence of the human genome," *Science*, 2001 Feb. 16; 291(5507):1304-51 discloses the sequence of the human genome, which information is publicly available from NCBI. Another reference genomic sequence is a current NCBI build as obtained from the UCSC genome gateway.

Wheeler et al., "The complete genome of an individual by massively parallel DNA sequencing," *Nature*, 2008 Apr. 17; 452(7189):872-6 discloses the DNA sequence of a diploid genome of a single individual, James D. Watson, sequenced to 7.4-fold redundancy in two months using massively parallel sequencing in picoliter-size reaction vessels. Comparison of the sequence to the reference genome led to the identification of 3.3 million single nucleotide polymorphisms, of which 10,654 cause amino-acid substitution within the coding sequence.

Quake et al., US 2007/0202525 entitled "Non-invasive fetal genetic screening by digital analysis," published Aug. 30, 2007, discloses a process in which maternal blood containing fetal DNA is diluted to a nominal value of approximately 0.5 genome equivalent of DNA per reaction sample.

Chiu et al., "Noninvasive prenatal diagnosis of fetal chromosomal aneuploidy by massively parallel genomic DNA sequencing of DNA in maternal plasma," *Proc. Natl. Acad. Sci.* 105(51):20458-20463 (Dec. 23, 2008) discloses a method for determining fetal aneuploidy using massively parallel sequencing. Disease status determination (aneuploidy) was made by calculating a "z score." Z scores were compared with reference values, from a population restricted to euploid male fetuses. The authors noted in passing that G/C content affected the coefficient of variation.

Lo et al., "Diagnosing Fetal Chromosomal Aneuploidy Using Massively Parallel Genomic Sequencing," US 2009/0029377, published Jan. 29, 2009, discloses a method in which respective amounts of a clinically-relevant chromosome and of background chromosomes are determined from results of massively parallel sequencing. It was found that the percentage representation of sequences mapped to chromosome 21 is higher in a pregnant woman carrying a trisomy 21 fetus when compared with a pregnant woman carrying a normal fetus. For the four pregnant women each carrying a euploid fetus, a mean of 1.345% of their plasma DNA sequences were aligned to chromosome 21.

Lo et al., Determining a Nucleic Acid Sequence Imbalance," US 2009/0087847 published Apr. 2, 2009, discloses a method for determining whether a nucleic acid sequence imbalance exists, such as an aneuploidy, the method comprising deriving a first cutoff value from an average concentration of a reference nucleic acid sequence in each of a plurality of reactions, wherein the reference nucleic acid sequence is either the clinically relevant nucleic acid sequence or the background nucleic acid sequence; comparing the parameter to the first cutoff value; and based on the comparison, determining a classification of whether a nucleic acid sequence imbalance exists.

BRIEF SUMMARY OF THE INVENTION

The following brief summary is not intended to include all features and aspects of the present invention, nor does it imply that the invention must include all features and aspects discussed in this summary.

The present invention comprises a method for analyzing a maternal sample, e.g., from peripheral blood. It is not invasive into the fetal space, as is amniocentesis or chorionic villi sampling. In the preferred method, fetal DNA which is present in the maternal plasma is used. The fetal DNA is in one aspect of the invention enriched due to the bias in the method towards shorter DNA fragments, which tend to be fetal DNA. The method is independent of any sequence difference between the maternal and fetal genome. The DNA obtained, preferably from a peripheral blood draw, is a mixture of fetal and maternal DNA. The DNA obtained is at least partially sequenced, in a method which gives a large number of short reads. These short reads act as sequence tags, in that a significant fraction of the reads are sufficiently unique to be mapped to specific chromosomes or chromosomal locations known to exist in the human genome. They are mapped exactly, or may be mapped with one mismatch, as in the examples below. By counting the number of sequence tags mapped to each chromosome (1-22, X and Y), the over- or under-representation of any chromosome or chromosome portion in the mixed DNA contributed by an aneuploid fetus can be detected. This method does not require the sequence differentiation of fetal versus maternal DNA, because the summed contribution of both maternal and fetal sequences in a particular chromosome or chromosome portion will be different as between an intact, diploid chromosome and an aberrant chromosome, i.e., with an extra copy, missing portion or the like. In other words, the method does not rely on a priori sequence information that would distinguish fetal DNA from maternal DNA. The abnormal distribution of a fetal chromosome or portion of a chromosome (i.e., a gross deletion or insertion) may be determined in the present method by enumeration of sequence tags as mapped to different chromosomes. The median count of autosomal values (i.e., number of sequence tags per autosome) is used as a normalization constant to account for differences in total number of sequence tags is used for comparison between samples and between chromosomes The term "chromosome portion" is used herein to denote either an entire chromosome or a significant fragment of a chromosome. For example, moderate Down syndrome has been associated with partial trisomy 21q22.2→qter. By analyzing sequence tag density in predefined subsections of chromosomes (e.g., 10 to 100 kb windows), a normalization constant can be calculated, and chromosomal subsections quantified (e.g., 21q22.2). With large enough sequence tag counts, the present method can be applied to arbitrarily small fractions of fetal DNA. It has been demonstrated to be accurate down to 6% fetal DNA concentration. Exemplified below is the successful use of shotgun sequencing and mapping of DNA to detect fetal trisomy 21 (Down syndrome), trisomy 18 (Edward syndrome), and trisomy 13 (Patau syndrome), carried out non-invasively using cell-free fetal DNA in maternal plasma. This forms the basis of a universal, polymorphism-independent non-invasive diagnostic test for fetal aneuploidy. The sequence data also allowed us to characterize plasma DNA in unprecedented detail, suggesting that it is enriched for nucleosome bound fragments. The method may also be employed so that the sequence data obtained may be further analyzed to obtain information regarding polymorphisms and mutations.

Thus, the present invention comprises, in certain aspects, a method of testing for an abnormal distribution of a specified chromosome portion in a mixed sample of normally and abnormally distributed chromosome portions obtained from a single subject, such as a mixture of fetal and maternal DNA in a maternal plasma sample. One carries out sequence determinations on the DNA fragments in the sample, obtaining sequences from multiple chromosome portions of the mixed sample to obtain a number of sequence tags of sufficient length of determined sequence to be assigned to a chromosome location within a genome and of sufficient number to reflect abnormal distribution. Using a reference sequence, one assigns the sequence tags to their corresponding chromosomes including at least the specified chromosome by comparing the sequence to reference genomic sequence. Often there will be on the order of millions of short sequence tags that are assigned to certain chromosomes, and, importantly, certain positions along the chromosomes. One then may determine a first number of sequence tags mapped to at least one normally distributed chromosome portion and a second number of sequence tags mapped to the specified chromosome portion, both chromosomes being in one mixed sample. The present method also involves correcting for nonuniform distribution sequence tags to different chromosomal portions. This is explained in detail below, where a number of windows of defined length are created along a chromosome, the windows being on the order of kilobases in length, whereby a number of sequence tags will fall into many of the windows and the windows covering each entire chromosome in question, with exceptions for non-informative regions, e.g., centromere regions and repetitive regions. Various average numbers, i.e., median values, are calculated for different windows and compared. By counting sequence tags within a series of predefined windows of equal lengths along different chromosomes, more robust and statistically significant results may be obtained. The present method also involves calculating a differential between the first number and the second number which is determinative of whether or not the abnormal distribution exists.

In certain aspects, the present invention may comprise a computer programmed to analyze sequence data obtained from a mixture of maternal and fetal chromosomal DNA. Each autosome (chr. 1-22) is computationally segmented into contiguous, non-overlapping windows. (A sliding window could also be used). Each window is of sufficient length to contain a significant number of reads (sequence tags, having about 20-100 bp of sequence) and not still have a number of windows per chromosome. Typically, a window will be between 10 kb and 100 kb, more typically between 40 and 60 kb. There would, then, for example, accordingly be approximately between 3,000 and 100,000 windows per chromosome. Windows may vary widely in the number of sequence tags that they contain, based on location (e.g., near a centromere or repeating region) or G/C content, as explained below. The median (i.e., middle value in the set) count per window for each chromosome is selected; then the median of the autosomal values is used to account for differences in total number of sequence tags obtained for different chromosomes and distinguish interchromosomal variation from sequencing bias from aneuploidy. This mapping method may also be applied to discern partial deletions or insertions in a chromosome. The present method also provides a method for correcting for bias resulting from G/C content. For example, some the Solexa sequencing method was found to produce more sequence tags from fragments with increased G/C content. By assigning a weight to each sequence tag based on the G/C content of a window in which the read falls. The window for GC calculation is preferably smaller than the window for sequence tag density calculation.

BRIEF DESCRIPTION OF THE DRAWINGS

FIG. 1 is a scatter plot graph showing sequence tag densities from eighteen samples, having five different genotypes, as indicated in the figure legend. Fetal aneuploidy is detectable by the over-representation of the affected chromosome in maternal blood. FIG. 1B represents an enlargement of the chromosome 21 data.

FIG. 2 suggests that the present method may be employed at a very early stage of pregnancy. The data were obtained from the 10-week stage and later because that is the earliest stage at which chorionic villi sampling is done. (Amniocentesis is done later). From the level of the confidence interval, one would expect to obtain meaningful data as early as 4 weeks gestational age, or possibly earlier.

FIG. 4 is a pair of line graphs showing distribution of sequence tags around transcription start sites (TSS) of ReSeq genes on all autosomes and chromosome X from plasma DNA sample of a normal male pregnancy (top, FIG. 4A) and randomly sheared genomic DNA control (bottom, FIG. 4B). The number of tags within each 5 bp window was counted within ±1000 bp region around each TSS, taking into account the strand each sequence tag mapped to. The counts from all transcription start sites for each 5 bp window were summed and normalized to the median count among the 400 windows. A moving average was used to smooth the data. A peak in the sense strand represents the beginning of a nucleosome, while a peak in the anti-sense strand represents the end of a nucleosome. In the plasma DNA sample shown here, five well-positioned nucleosomes are observed downstream of transcription start sites and are represented as grey ovals. The number below within each oval represents the distance in base pairs between adjacent peaks in the sense and anti-sense strands, corresponding to the size of the inferred nucleosome. No obvious pattern is observed for the genomic DNA control.

That is, in the left panels (A and C), one plots the distribution of reads per chromosome coordinate, i.e., chromosomal position in terms of number of reads within each 50 kb non-overlapping sliding window. Then, one determines the distribution of the number of sequence tags for each 50 kb window, and obtains a median number of sequence tags per chromosome for all autosomes and chromosome X (Examples of chr 1 [top] and chr 22 [bottom] are illustrated here). These results are referred to as M. The median of the 22 values of M (from all autosomes, chromosomes 1 through 22) is used as the normalization constant N. The normalized sequence tag density of each chromosome is M/N (e.g., chr 1: M1/N; chr 22: M22/N). Such normalization is necessary to compare different patient samples since the total number of sequence tags (thus, the sequence tag density) for each patient sample is different (the total number of sequence tags fluctuates between ~8 to ~12 million). The analysis thus flows from frequency of reads per coordinate (A and C) to # reads per window (B and D) to a combination of all chromosomes.

Figure 10:
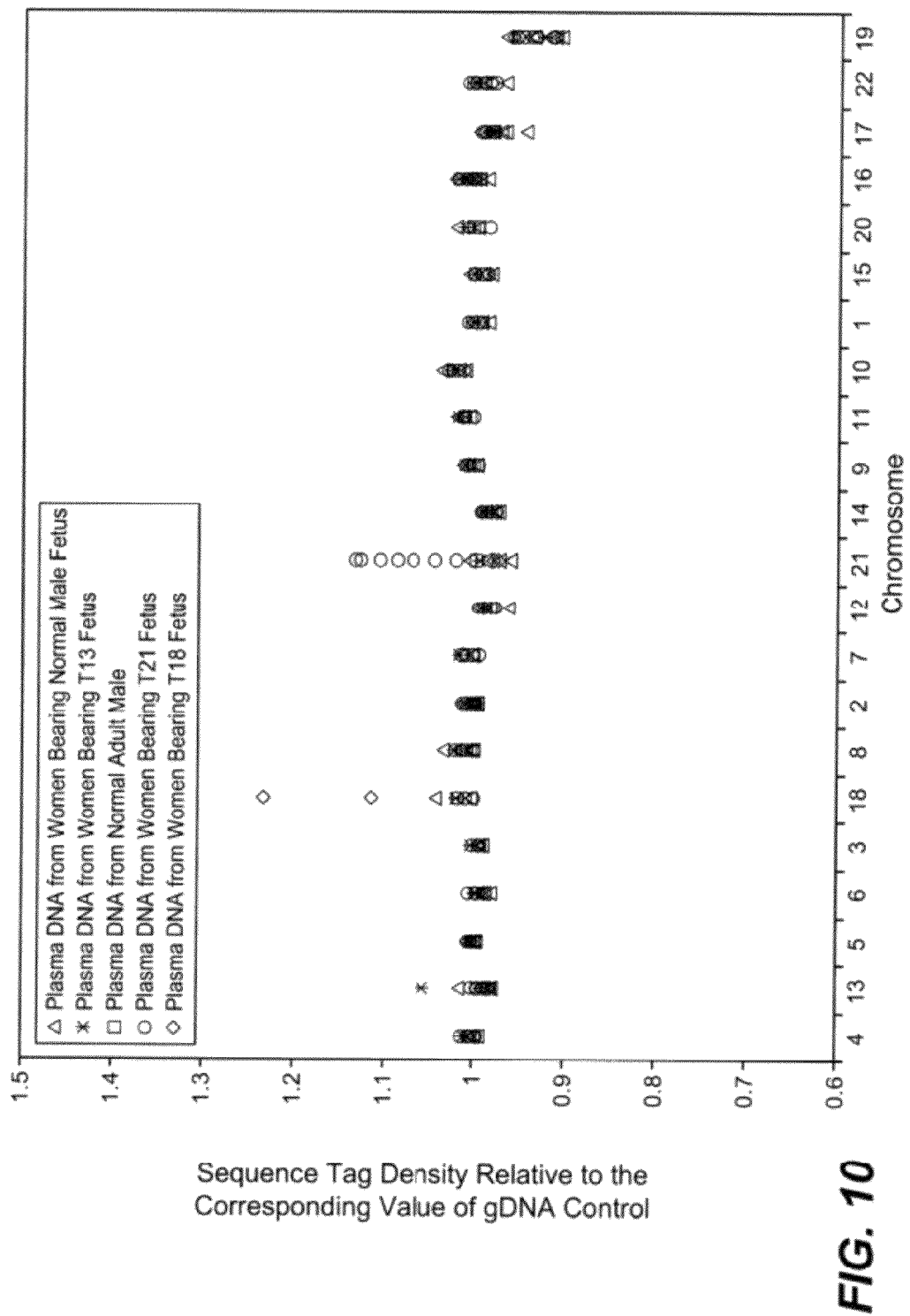

FIG. 10 is a scatter plot graph showing data from different samples, as in FIG. 1, except that bias for G/C sampling has been eliminated.

Figure 11:
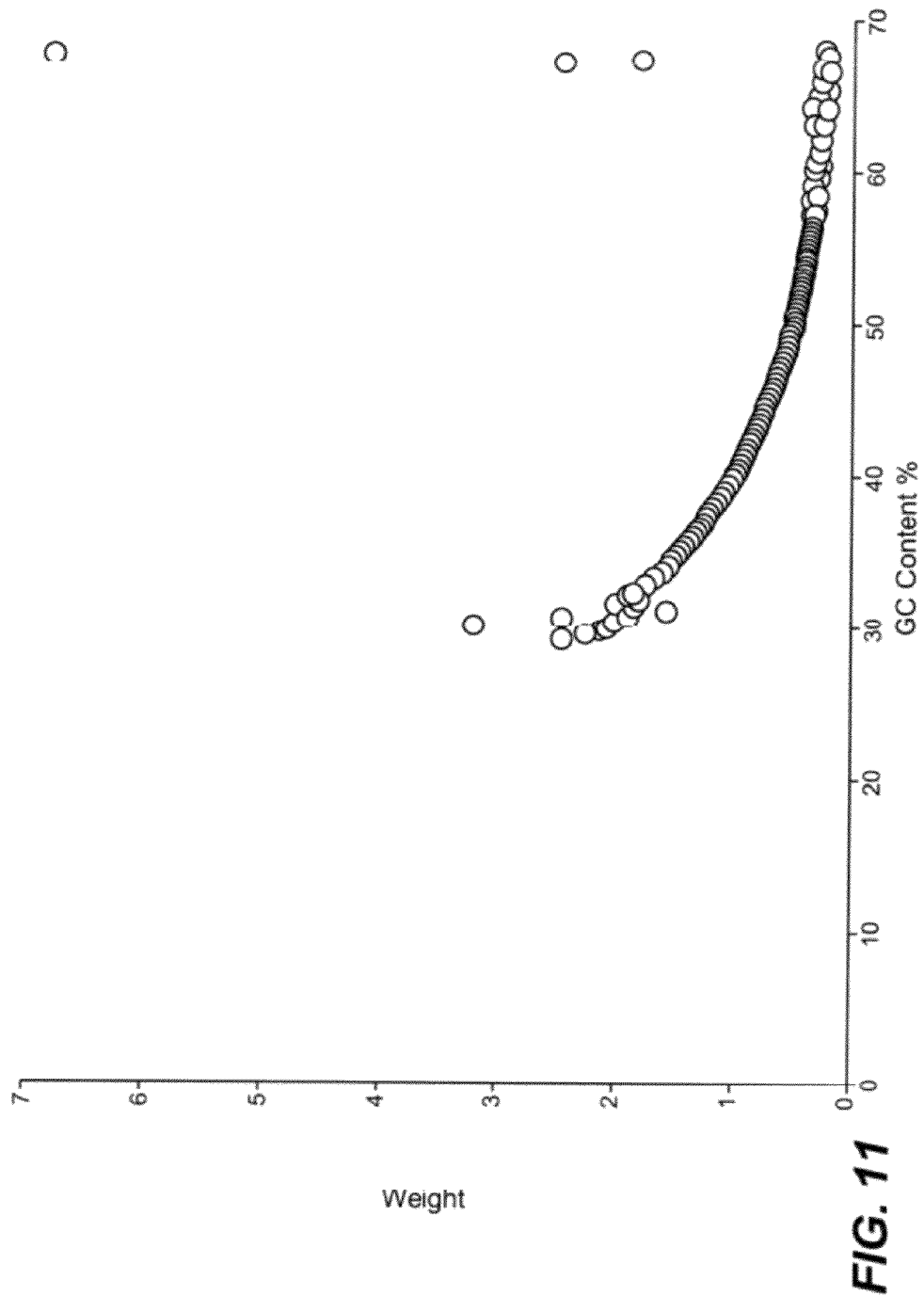

FIG. 11 is a scatter plot graph showing the weight given to different sequence samples according to percentage of G/C content, with lower weight given to samples with a higher G/C content. G/C content ranges from about 30% to about 70%; weight can range over a factor of about 3.

Figure 12:
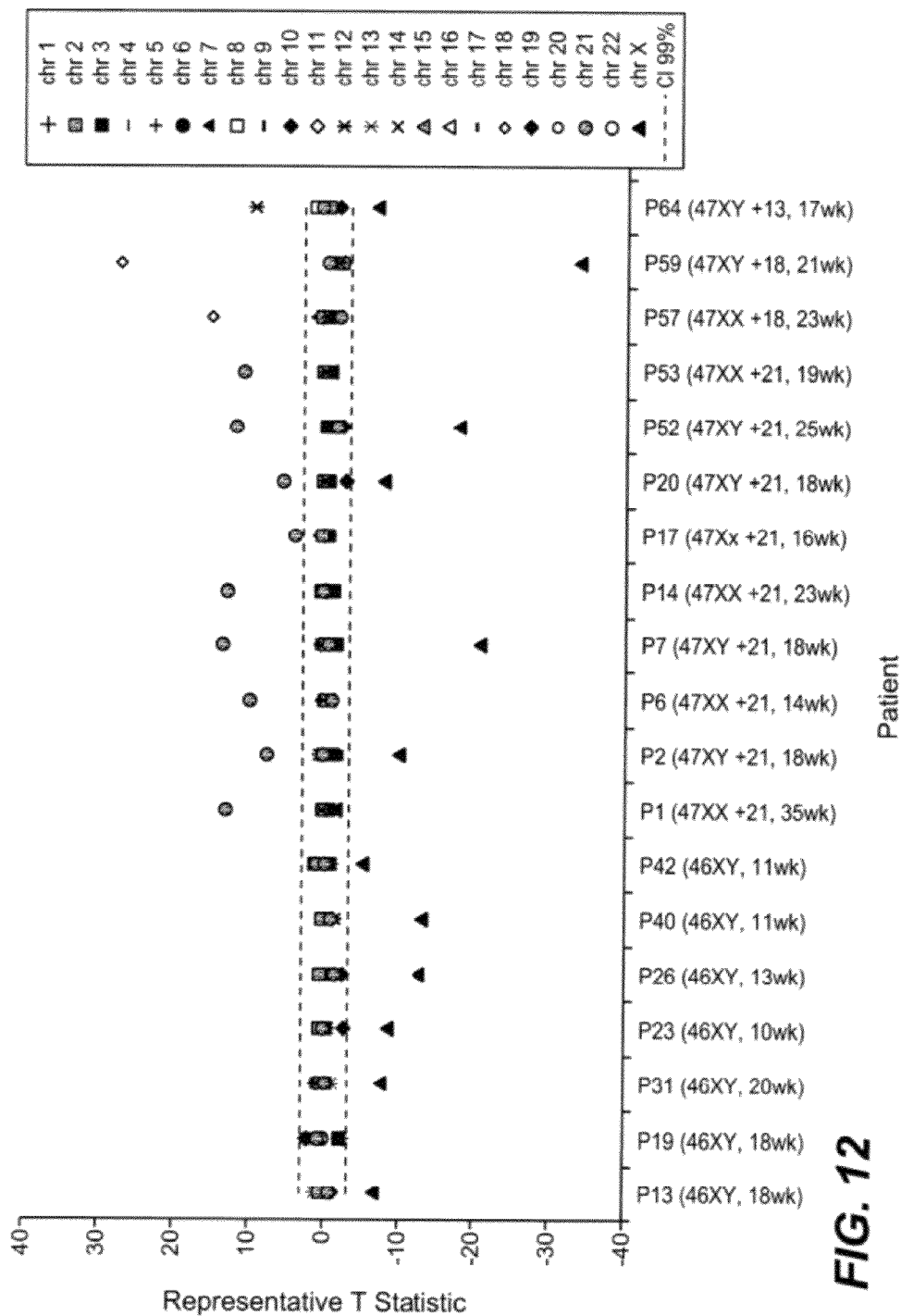

FIG. 12 is a scatter plot graph which illustrates results of selected patients as indicated on the x axis, and, for each patient, a distribution of chromosome representation on the Y axis, as deviating from a representative t statistic, indicated as zero.

Figure 13:
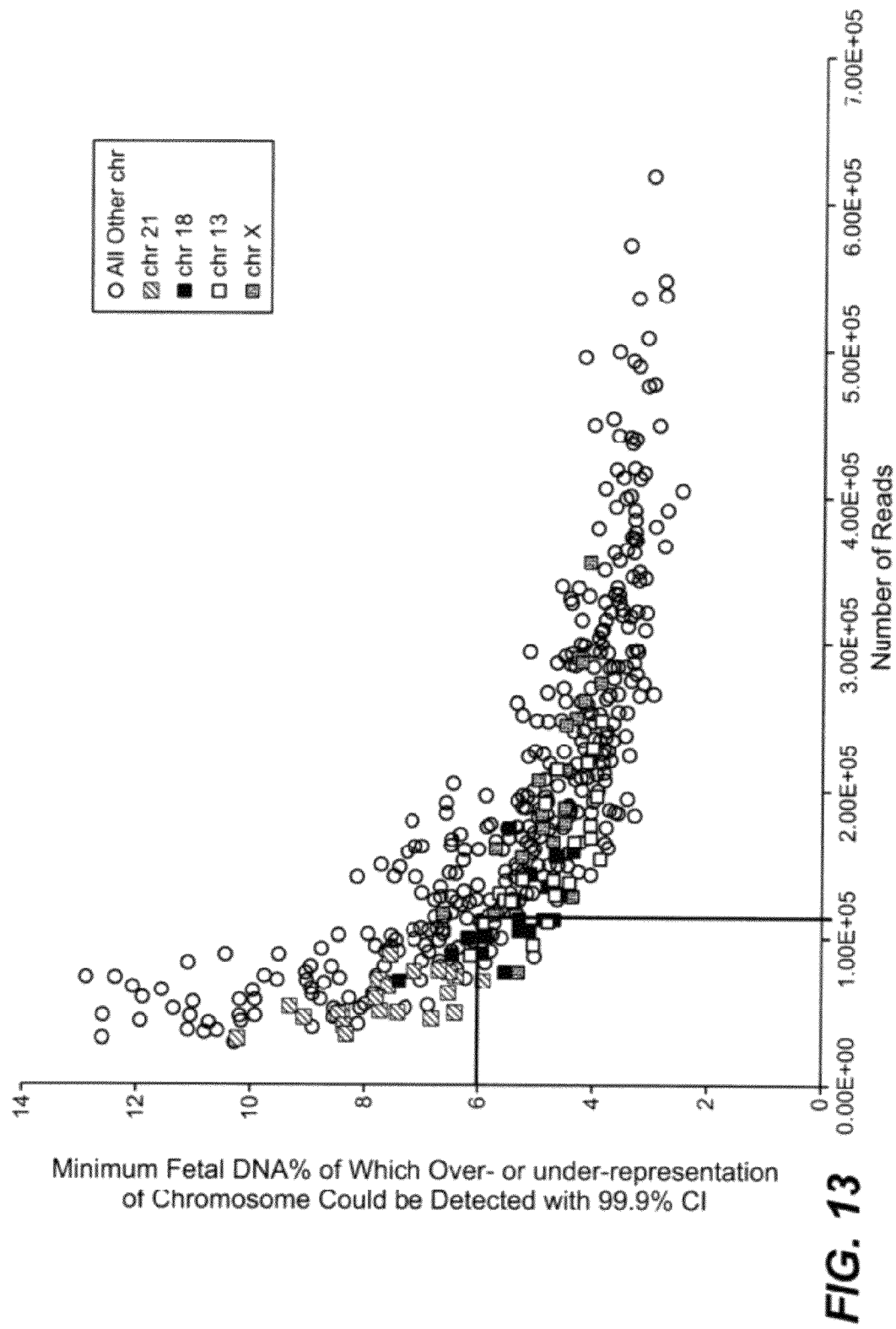

FIG. 13 is a scatter plot graph showing the minimum fetal DNA percentage of which over- or under-representation of a chromosome could be detected with a 99.9% confidence level for chromosomes 21, 18, 13 and Chr. X, and a value for all other chromosomes.

Figure 14:
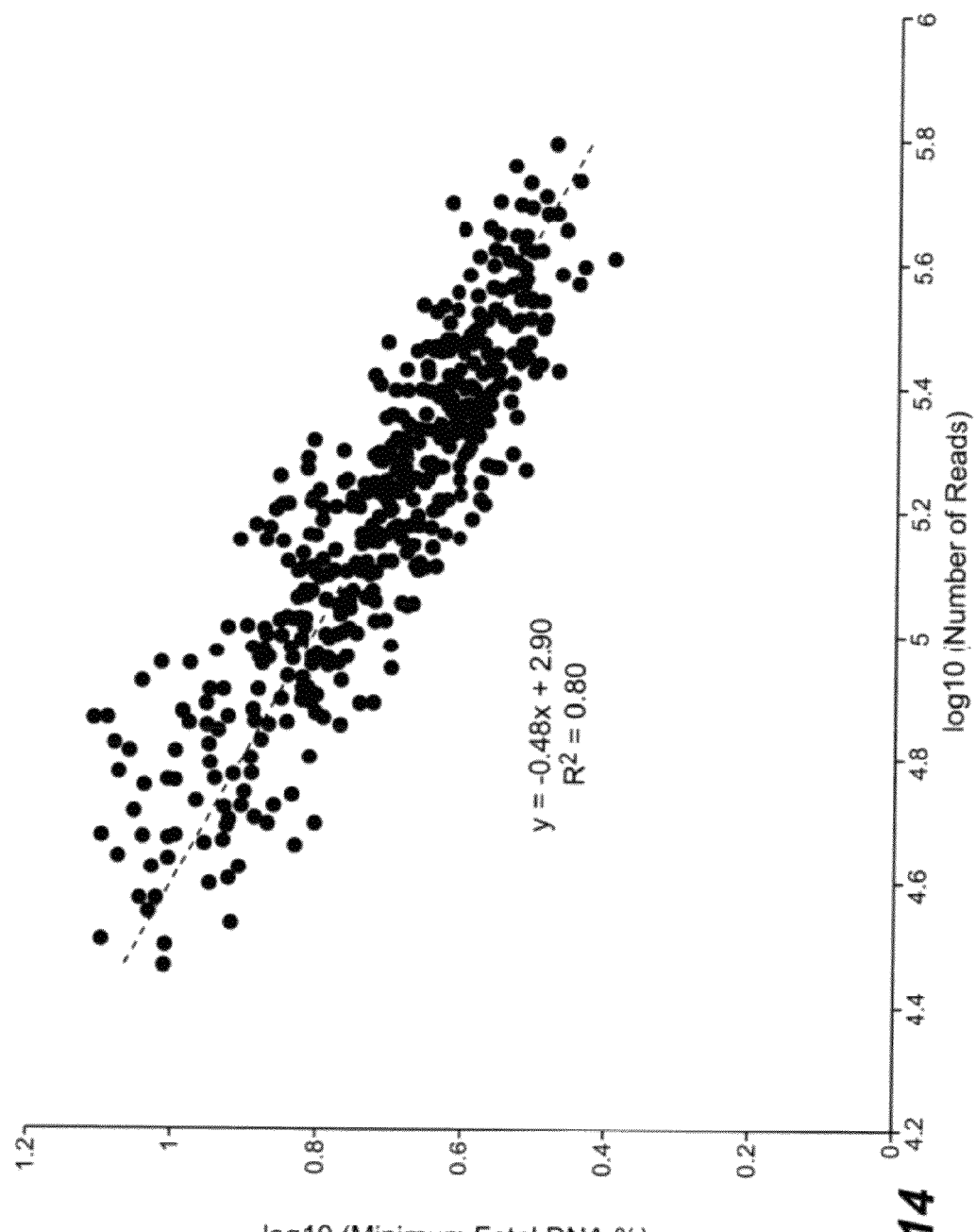

FIG. 14 is a scatter plot graph showing a linear relationship between log 10 of minimum fetal DNA percentage that is needed versus log 10 of the number of reads required.

DETAILED DESCRIPTION OF THE PREFERRED EMBODIMENT

Overview

Definitions

Unless defined otherwise, all technical and scientific terms used herein have the same meaning as commonly understood by those of ordinary skill in the art to which this invention belongs. Although any methods and materials similar or equivalent to those described herein can be used in the practice or testing of the present invention, the preferred methods and materials are described. Generally, nomenclatures utilized in connection with, and techniques of, cell and molecular biology and chemistry are those well known and commonly used in the art. Certain experimental techniques, not specifically defined, are generally performed according to conventional methods well known in the art and as described in various general and more specific references that are cited and discussed throughout the present specification. For purposes of the clarity, following terms are defined below.

"Sequence tag density" means the normalized value of sequence tags for a defined window of a sequence on a chromosome (in a preferred embodiment the window is about 50 kb), where the sequence tag density is used for comparing different samples and for subsequent analysis. A "sequence tag" is a DNA sequence of sufficient length that it may be assigned specifically to one of chromosomes 1-22, X or Y. It does not necessarily need to be, but may be non-repetitive within a single chromosome. A certain, small degree of mismatch (0-1) may be allowed to account for minor polymorphisms that may exist between the reference genome and the individual genomes (maternal and fetal) being mapped. The value of the sequence tag density is normalized within a sample. This can be done by counting the number of tags falling within each window on a chromosome; obtaining a median value of the total sequence tag count for each chromosome; obtaining a median value of all of the autosomal values; and using this value as a normalization constant to account for the differences in total number of sequence tags obtained for different samples. A sequence tag density as calculated in this way would ideally be about 1 for a disomic chromosome. As further described below, sequence tag densities can vary according to sequencing artifacts, most notably G/C bias; this is corrected as described. This method does not require the use of an external standard, but, rather, provides an internal reference, derived from al of the sequence tags (genomic sequences), which may be, for example, a single chromosome or a calculated value from all autosomes.

"T21" means trisomy 21.

"T18" means trisomy 18.

"T13" means trisomy 13.

"Aneuploidy" is used in a general sense to mean the presence or absence of an entire chromosome, as well as the presence of partial chromosomal duplications or deletions or kilobase or greater size, as opposed to genetic mutations or polymorphisms where sequence differences exist.

"Massively parallel sequencing" means techniques for sequencing millions of fragments of nucleic acids, e.g., using attachment of randomly fragmented genomic DNA to a planar, optically transparent surface and solid phase amplification to create a high density sequencing flow cell with millions of clusters, each containing ~1,000 copies of template per sq. cm. These templates are sequenced using four-color DNA sequencing-by-synthesis technology. See, products offered by Illumina, Inc., San Diego, Calif. In the present work, sequences were obtained, as described below, with an Illumina/Solexa 1G Genome Analyzer. The Solexa/Illumina method referred to below relies on the attachment of randomly fragmented genomic DNA to a planar, optically transparent surface. In the present case, the plasma DNA does not need to be sheared. Attached DNA fragments are extended and bridge amplified to create an ultra-high density sequencing flow cell with $\geqq 50$ million clusters, each containing ~1,000 copies of the same template. These templates are sequenced using a robust four-color DNA sequencing-by-synthesis technology that employs reversible terminators with removable fluorescent dyes. This novel approach ensures high accuracy and true base-by-base sequencing, eliminating sequence-context specific errors and enabling sequencing through homopolymers and repetitive sequences.

High-sensitivity fluorescence detection is achieved using laser excitation and total internal reflection optics. Short sequence reads are aligned against a reference genome and genetic differences are called using specially developed data analysis pipeline software.

Copies of the protocol for whole genome sequencing using Solexa technology may be found at BioTechniques® Protocol Guide 2007 Published December 2006: p 29, www(dot)biotechniques.com/default.asp?page=protocol&subsection=article_display&id=112378. Solexa's oligonucleotide adapters are ligated onto the fragments, yielding a fully-representative genomic library of DNA templates without cloning. Single molecule clonal amplification involves six steps: Template hybridization, template amplification, linearization, blocking 3' ends, denaturation and primer hybridization. Solexa's Sequencing-by-Synthesis utilizes four proprietary nucleotides possessing reversible fluorophore and termination properties. Each sequencing cycle occurs in the presence of all four nucleotides.

The presently used sequencing is preferably carried out without a preamplification or cloning step, but may be combined with amplification-based methods in a microfluidic chip having reaction chambers for both PCR and microscopic template-based sequencing. Only about 30 bp of random sequence information are needed to identify a sequence as belonging to a specific human chromosome. Longer sequences can uniquely identify more particular targets. In the present case, a large number of 25 bp reads were obtained, and due to the large number of reads obtained, the 50% specificity enabled sufficient sequence tag representation.

Further description of a massively parallel sequencing method, which employed the below referenced 454 method is found in Rogers and Ventner, "Genomics: Massively parallel sequencing," Nature, 437, 326-327 (15 Sep. 2005). As described there, Rothberg and colleagues (Margulies, M. et al. Nature 437, 376-380 (2005)), have developed a highly parallel system capable of sequencing 25 million bases in a four-hour period—about 100 times faster than the current state-of-the-art Sanger sequencing and capillary-based electrophoresis platform. The method could potentially allow one individual to prepare and sequence an entire genome in a few days. The complexity of the system lies primarily in the sample preparation and in the microfabricated, massively parallel platform, which contains 1.6 million picoliter-sized reactors in a 6.4-cm$^2$ slide. Sample preparation starts with fragmentation of the genomic DNA, followed by the attachment of adaptor sequences to the ends of the DNA pieces. The adaptors allow the DNA fragments to bind to tiny beads (around 28μ in diameter). This is done under conditions that allow only one piece of DNA to bind to each bead. The beads are encased in droplets of oil that contain all of the reactants needed to amplify the DNA using a standard tool called the polymerase chain reaction. The oil droplets form part of an emulsion so that each bead is kept apart from its neighbor, ensuring the amplification is uncontaminated. Each bead ends up with roughly 10 million copies of its initial DNA fragment. To perform the sequencing reaction, the DNA-template-carrying beads are loaded into the picoliter reactor wells—each well having space for just one bead. The technique uses a sequencing-by-synthesis method developed by Uhlen and colleagues, in which DNA complementary to each template strand is synthesized. The nucleotide bases used for sequencing release a chemical group as the base forms a bond with the growing DNA chain, and this group drives a light-emitting reaction in the presence of specific enzymes and luciferin. Sequential washes of each of the four possible nucleotides are run over the plate, and a detector senses which of the wells emit light with each wash to determine the sequence of the growing strand. This method has been adopted commercially by 454 Life Sciences.

Further examples of massively parallel sequencing are given in US 20070224613 by Strathmann, published Sep. 27, 2007, entitled "Massively Multiplexed Sequencing." Also, for a further description of massively parallel sequencing, see US 2003/0022207 to Balasubramanian, et al., published Jan. 30, 2003, entitled "Arrayed polynucleotides and their use in genome analysis."

General Description of Method and Materials

Overview

Non-invasive prenatal diagnosis of aneuploidy has been a challenging problem because fetal DNA constitutes a small percentage of total DNA in maternal blood (13) and intact fetal cells are even rarer (6, 7, 9, 31, 32). We showed in this study the successful development of a truly universal, polymorphism-independent non-invasive test for fetal aneuploidy. By directly sequencing maternal plasma DNA, we could detect fetal trisomy 21 as early as 14th week of gestation. Using cell-free DNA instead of intact cells allows one to avoid complexities associated with microchimerism and foreign cells that might have colonized the mother; these cells occur at such low numbers that their contribution to the cell-free DNA is negligible (33, 34). Furthermore, there is evidence that cell-free fetal DNA clears from the blood to undetectable levels within a few hours of delivery and therefore is not carried forward from one pregnancy to the next (35-37).

Rare forms of aneuploidy caused by unbalanced translocations and partial duplication of a chromosome are in principle detectable by the approach of shotgun sequencing, since the density of sequence tags in the triplicated region of the chromosome would be higher than the rest of the chromosome. Detecting incomplete aneuploidy caused by mosaicism is also possible in principle but may be more challenging, since it depends not only on the concentration of fetal DNA in maternal plasma but also the degree of fetal mosaicism. Further studies are required to determine the effectiveness of shotgun sequencing in detecting these rare forms of aneuploidy.

The present method is applicable to large chromosomal deletions, such as 5p-Syndrome (five p minus), also known as Cat Cry Syndrome or Cri du Chat Syndrome. 5p-Syndrome is characterized at birth by a high-pitched cry, low birth weight, poor muscle tone, microcephaly, and potential medical complications. Similarly amenable disorders addressed by the present methods are p-, monosomy 9P, otherwise known as Alfi's Syndrome or 9P-, 22q11.2 deletion syndrome, Emanuel Syndrome, also known in the medical literature as the Supernumerary Der(22) Syndrome, trisomy 22, Unbalanced 11/22 Translocation or partial trisomy 11/22, Microdeletion and Microduplication at 16p11.2, which is associated with autism, and other deletions or imbalances, including those that are presently unknown.

An advantage of using direct sequencing to measure aneuploidy non-invasively is that it is able to make full use of the sample, while PCR based methods analyze only a few targeted sequences. In this study, we obtained on average 5 million reads per sample in a single run, of which ~66,000 mapped to chromosome 21. Since those 5 million reads represent only a portion of one human genome, in principle less than one genomic equivalent of DNA is sufficient for the detection of aneuploidy using direct sequencing. In practice, a larger amount of DNA was used since there is sample loss during sequencing library preparation, but it may be possible to further reduce the amount of blood required for analysis.

Mapping shotgun sequence information (i.e., sequence information from a fragment whose physical genomic position is unknown) can be done in a number of ways, which involve alignment of the obtained sequence with a matching sequence in a reference genome. See, Li et al., "Mapping short DNA sequencing reads and calling variants using mapping quality score," *Genome Res.*, 2008 Aug. 19. [Epub ahead of print].

We observed that certain chromosomes have large variations in the counts of sequenced fragments (from sample to sample, and that this depends strongly on the G/C content (FIG. 1A) It is unclear at this point whether this stems from PCR artifacts during sequencing library preparation or cluster generation, the sequencing process itself, or whether it is a true biological effect relating to chromatin structure. We strongly suspect that it is an artifact since we also observe G/C bias on genomic DNA control, and such bias on the Solexa sequencing platform has recently been reported (38, 39). It has a practical consequence since the sensitivity to aneuploidy detection will vary from chromosome to chromosome; fortunately the most common human aneuploidies (such as 13, 18, and 21) have low variation and therefore high detection sensitivity. Both this problem and the sample volume limitations may possibly be resolved by the use of single molecule sequencing technologies, which do not require the use of PCR for library preparation (40).

Plasma DNA samples used in this study were obtained about 15 to 30 minutes after amniocentesis or chorionic villus sampling. Since these invasive procedures disrupt the interface between the placenta and maternal circulation, there have been discussions whether the amount of fetal DNA in maternal blood might increase following invasive procedures. Neither of the studies to date have observed a significant effect (41, 42).

Our results support this conclusion, since using the digital PCR assay we estimated that fetal DNA constituted less than or equal to 10% of total cell-free DNA in the majority of our maternal plasma samples. This is within the range of previously reported values in maternal plasma samples obtained prior to invasive procedures (13). It would be valuable to have a direct measurement addressing this point in a future study.

Figure 7:
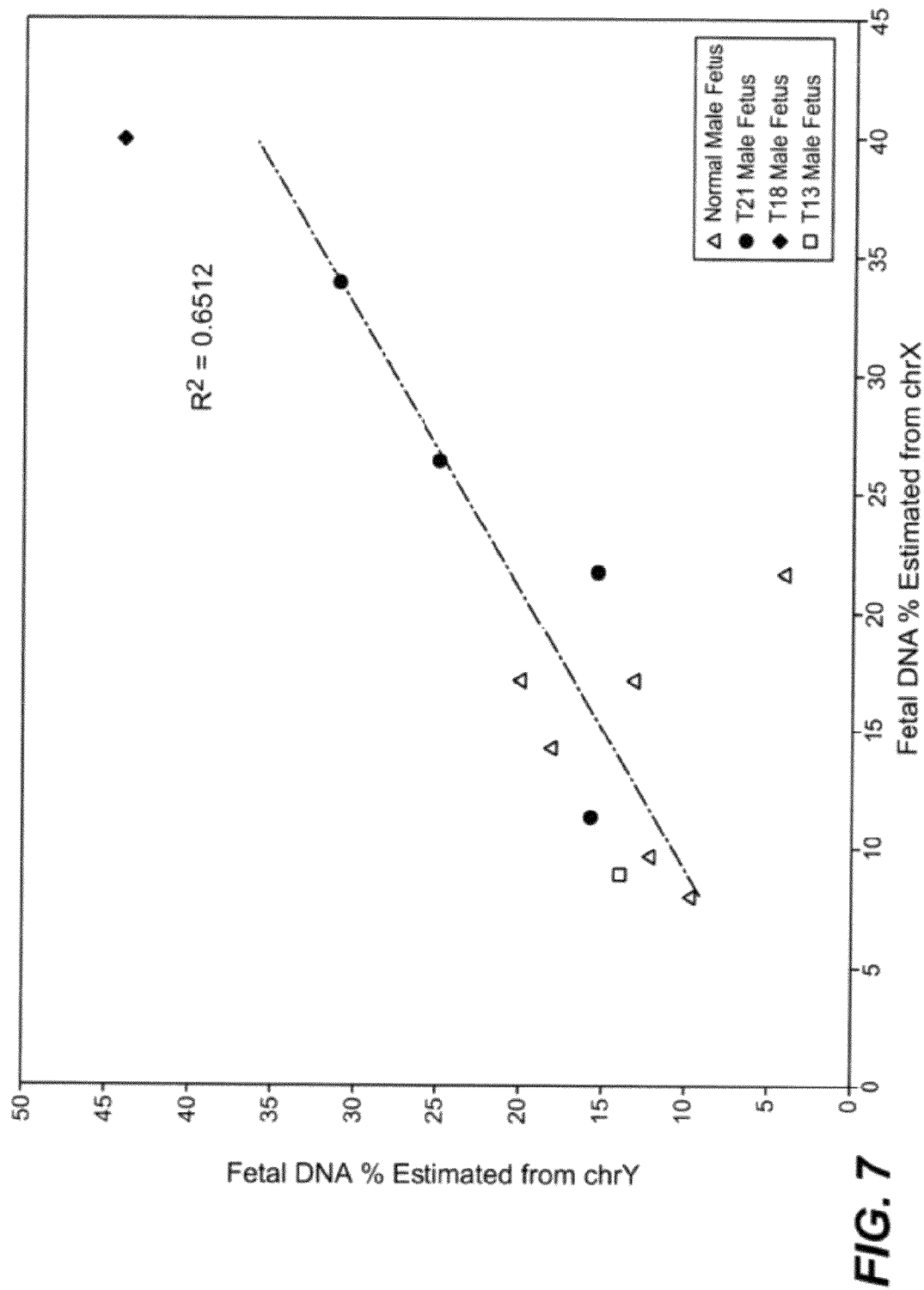
FIG. 7 is a scatter plot graph showing a comparison of the estimation of fetal DNA fraction for cell-free DNA samples from 12 male pregnancies using sequencing data from chromosomes X and Y. The dashed line represents a simple linear regression line, with a slope of 0.85. The R2 value represents the square of the correlation coefficient. There is a statistically significant correlation between fetal DNA fraction estimated from chromosomes X and Y (p=0.0015).

The average fetal DNA fraction estimated from sequencing data is higher than the values estimated from digital PCR data by an average factor of two ($p<0.005$, paired t-test on all male pregnancies that have complete set of data). One possible explanation for this is that the PCR step during Solexa library preparation preferentially amplifies shorter fragments, which others have found to be enriched for fetal DNA (22, 23). Our own measurements of length distribution on one sample do not support this explanation, but nor can we reject it at this point. It should also be pointed out that using the sequence tags we find some variation of fetal fraction even in the same sample depending on which chromosome we use to make the calculation (FIG. 7, Table 1). This is most likely due to artifacts and errors in the sequencing and mapping processes, which are substantial—recall that only half of the sequence tags map to the human genome with one error or less. Finally, it is also possible that the PCR measurements are biased since they are only sampling a tiny fraction of the fetal genome.

Our sequencing data suggest that the majority of cell-free plasma DNA is of apoptotic origin and shares features of nucleosomal DNA. Since nucleosome occupancy throughout the eukaryotic genome is not necessarily uniform and depends on factors such as function, expression, or sequence of the region (30, 43), the representation of sequences from different loci in cell-free maternal plasma may not be equal, as one usually expects in genomic DNA extracted from intact cells. Thus, the quantity of a particular locus may not be representative of the quantity of the entire chromosome and care must be taken when one designs assays for measuring gene dosage in cell-free maternal plasma DNA that target only a few loci.

Historically, due to risks associated with chorionic villus sampling and amniocentesis, invasive diagnosis of fetal aneuploidy was primarily offered to women who were considered at risk of carrying an aneuploid fetus based on evaluation of risk factors such as maternal age, levels of serum markers, and ultrasonographic findings. Recently, an American College of Obstetricians and Gynecologists (ACOG) Practice Bulletin recommended that "invasive diagnostic testing for aneuploidy should be available to all women, regardless of maternal age" and that "pretest counseling should include a discussion of the risks and benefits of invasive testing compared with screening tests" (2).

A noninvasive genetic test based on the results described here and in future large-scale studies would presumably carry the best of both worlds: minimal risk to the fetus while providing true genetic information. The costs of the assay are already fairly low; the sequencing cost per sample as of this writing is about $700 and the cost of sequencing is expected to continue to drop dramatically in the near future.

Shotgun sequencing can potentially reveal many more previously unknown features of cell-free nucleic acids such as plasma mRNA distributions, as well as epigenetic features of plasma DNA such as DNA methylation and histone modification, in fields including perinatology, oncology and transplantation, thereby improving our understanding of the basic biology of pregnancy, early human development and disease.

Sequencing Methods

Commercially available sequencing equipment was used in the present illustrative examples, namely the Solexa/Illumina sequencing platform and the 454/Roche platform. It will be apparent to those skilled in the art that a number of different sequencing methods and variations can be used. One sequencing method that can be used to advantage in the present methods involves paired end sequencing. Fluorescently labeled sequencing primers could be used to simultaneously sequence both strands of a dsDNA template, as described e.g., in Wiemann et al. (*Anal. Biochem.* 224: 117 [1995]; *Anal. Biochem.* 234: 166 [1996]. Recent examples of this technique have demonstrated multiplex co-sequencing using the four-color dye terminator reaction chemistry pioneered by Prober et al. (*Science* 238: 336 [1987]). Solexa/Illumina offers a "Paired End Module" to its Genome Analyzer. Using this module, after the Genome Analyzer has completed the first sequencing read, the Paired-End Module directs the resynthesis of the original templates and the second round of cluster generation. The Paired-End Module is connected to the Genome Analyzer through a single fluidic connection. In addition, 454 has developed a protocol to generate a library of Paired End reads. These Paired End reads are approximately 84-nucleotide DNA fragments that have a 44-mer adaptor sequence in the middle flanked by a 20-mer sequence on each side. The two flanking 20-mers are segments of DNA that were originally located approximately 2.5 kb apart in the genome of interest.

By using paired end reads in the present method, one may obtain more sequence information from a given plasma DNA fragment, and, significantly, one may also obtain sequence information from both ends of the fragment. The fragment is mapped to the human genome as explained here elsewhere. After mapping both ends, one may deduce the length of the starting fragment. Since fetal DNA is known to be shorter than maternal DNA fragments circulating in plasma, one may use this information about the length of the DNA fragment to effectively increase the weight given to sequences obtained from shorter (e.g., about 300 bp or less) DNA fragments. Methods for weighting are given below.

Another method for increasing sensitivity to fetal DNA is to focus on certain regions within the human genome. One may use sequencing methods which select a priori sequences which map to the chromosomes of interest (as described here elsewhere, such as 18, 21, 13, X and Y). One may also choose to focus, using this method, on partial chromosomal deletions, such as 22q11 deletion syndrome. Other microdeletions and microduplications are set forth in Table 1 of US 2005/0181410, published Aug. 18, 2005 under the title "Methods and apparatuses for achieving precision genetic diagnosis."

In sequencing selected subsequences, one may employ sequence-based methodologies such as sequencing by array, or capture beads with specific genomic sequences used as capture probes. The use of a sequencing array can be implemented as described in Chetverin et al., "Oligonucleotide arrays: new concepts and possibilities," *Biotechnology* (NY). 1994 November; 12(11):1093-9, as well as Rothberg, US 2002/0012930 A1 entitled "Method of Sequencing a Nucleic Acid," and Reeve et al., "Sequencing by Hybridization," U.S. Pat. No. 6,399,364. In these methods, the target nucleic acid to be sequenced may be genomic DNA, cDNA or RNA. The sample is rendered single stranded and captured under hybridizing conditions with a number of single stranded probes which are catalogued by bar coding or by physical separation in an array. Emulsion PCR, as used in the 454 system, the SOLiD system, and Polonator (Dover Systems) and others may also be used, where capture is directed to specific target sequences, e.g., genome sequences mapping uniquely to chromosome 21 or other chromosome of interest, or to a chromosome region such as 15q11 (Prader-Willi syndrome), or excessive CGG repeats in the FMR1 gene (fragile X syndrome).

The subsequencing method is in one aspect contrary to conventional massively parallel sequencing methodologies, which seek to obtain all of the sequence information in a sample. This alternative method selectively ignores certain sequence information by using a sequencing method which selectively captures sample molecules containing certain predefined sequences. One may also use the sequencing steps exactly as exemplified, but in mapping the sequence fragments obtained, give greater weight to sequences which map to areas known to be more reliable in their coverage, such as exons. Otherwise, the method proceeds as described below, where one obtains a large number of sequence reads from one or more reference chromosomes, which are compared to a large number of reads obtained from a chromosome of interest, after accounting for variations arising from chromosomal length, G/C content, repeat sequences and the like.

One may also focus on certain regions within the human genome according to the present methods in order to identify partial monosomies and partial trisomies. As described below, the present methods involve analyzing sequence data in a defined chromosomal sliding "window," such as contiguous, nonoverlapping 50 Kb regions spread across a chromosome. Partial trisomies of 13q, 8p (8p23.1), 7q, distal 6p, 5p, 1q (3q25.1), 2q, 1q (1q42.1 and 1q21-qter), partial Xp and monosomy 4q35.1 have been reported, among others. For example, partial duplications of the long arm of chromosome 18 can result in Edwards syndrome in the case of a duplication of 18q21.1-qter (See, Mewar et al., "Clinical and molecular evaluation of four patients with partial duplications of the long arm of chromosome 18," *Am J Hum Genet.* 1993 December; 53(6):1269-78).

Shotgun Sequencing of Cell-Free Plasma DNA

Cell-free plasma DNA from 18 pregnant women and a male donor, as well as whole blood genomic DNA from the same male donor, were sequenced on the Solexa/Illumina platform. We obtained on average ~10 million 25 bp sequence tags per sample. About 50% (i.e., ~5 million) of the reads mapped uniquely to the human genome with at most 1 mismatch against the human genome, covering ~4% of the entire genome. An average of ~154,000, ~135,000, ~66,000 sequence tags mapped to chromosomes 13, 18, and 21, respectively. The number of sequence tags for each sample is detailed in the following Table 1 and Table 2.

TABLE 1

| Sample | Fetal Karyotype | Gestational Age (weeks) | Volume of Plasma | Amount of DNA | Approximate Amount of Input DNA * | Total Number of Sequence Tags |
|---|---|---|---|---|---|---|
| P1 Plasma DNA[§] | 47XX + 21 | 35 | 1.6 | 761 | 8.0 | 8206694 |
| P2 Plasma DNA[§] | 47XY + 21 | 18 | 1.4 | 585 | 5.2 | 7751384 |
| P6 Plasma DNA[§] | 47XY + 21 | 14 | 1.6 | 410 | 4.3 | 6699183 |
| P7 Plasma DNA[§] | 47XY + 21 | 18 | 2.2 | 266 | 3.8 | 8324473 |
| P14 Plasma DNA[§] | 47XX + 21 | 23 | 3.2 | 57 | 1.2 | 8924944 |
| P17 Plasma DNA[§] | 47XX + 21 | 16 | 2.3 | 210 | 3.2 | 11599833 |
| P19 Plasma DNA[§] | 46XY | 18 | 3.2 | 333 | 7.0 | 7305417 |
| P20 Plasma DNA[§] | 47XY + 21 | 18 | 1.3 | 408 | 3.6 | 11454876 |
| P23 Plasma DNA[§] | 46XY | 10 | 1.6 | 258 | 2.7 | 11851612 |
| P26 Plasma DNA[§] | 46XY | 13 | 3.0 | 340 | 6.7 | 11471297 |
| P31 Plasma DNA[§] | 46XY | 20 | 2.2 | 278 | 4.0 | 8967562 |
| P40 Plasma DNA[§] | 46XY | 11 | 2.6 | 217 | 3.7 | 9205197 |
| P42 Plasma DNA[§] | 46XY | 11 | 3.0 | 276 | 5.5 | 8364774 |
| P52 Plasma DNA[§] | 47XY + 21 | 25 | 1.6 | 645 | 6.8 | 9192596 |
| P53 Plasma DNA[§] | 47XX + 21 | 19 | 1.6 | 539 | 5.7 | 9771887 |
| P57 Plasma DNA[§] | 47XX + 18 | 23 | 2.0 | 199 | 2.6 | 15041417 |
| P59 Plasma DNA[§] | 47XY + 18 | 21 | 2.0 | 426 | 5.6 | 11910483 |
| P64 Plasma DNA[§] | 47XY + 13 | 17 | 1.8 | 204 | 2.4 | 12097478 |
| Male Donor Plasma DNA[§] | — | — | 1.8 | 485 | 5.8 | 6669125 |
| Male Donor Whole Blood Genomic DNA[§] | — | — | — | — | 2.1 | 8519495 |
| P25 Plasma DNA[¶] | 46XY | 11 | 5.6 | 132 | 4.9 | 242599 |
| P13 Plasma DNA[§] | 46XY | 18 | 5.6 | 77 | 2.9 | 4168455 |

TABLE 2

| Sample | Number of Sequence Tags Mapped Uniquely to the Human Genome (hg18) with At Most 1 Mismatch | % Fetal DNA Estimated By Digital PCR with SRY Assay (male fetuses) | % Fetal DNA Estimated by ChrY Sequence Tags (male fetuses) | % Fetal DNA Estimated by Depletion of ChrX Sequence Tags (male fetuses) | % Fetal DNA Estimated by Addition of Trisomic Chromosome Sequence Tags (aneuploid fetuses) | Overall G/C content Of Sequence Tags (%) |
|---|---|---|---|---|---|---|
| P1 Plasma DNA[§] | 4632637 | — | — | — | 35.0 | 43.65 |
| P2 Plasma DNA[§] | 4313884 | 6.4 | 15.4 | 21.6 | 15.5 | 48.72 |
| P6 Plasma DNA[§] | 3878383 | — | — | — | 22.9 | 44.78 |
| P7 Plasma DNA[§] | 4294865 | 9.1 | 31.0 | 33.8 | 28.6 | 48.07 |
| P14 Plasma DNA[§] | 3603767 | — | — | — | 30.5 | 46.38 |
| P17 Plasma DNA[§] | 5968932 | — | — | — | 7.8 | 44.29 |
| P19 Plasma DNA[§] | 3280521 | <5.9[‡] | 4.14 | 21.5 | — | 50.09 |
| P20 Plasma DNA[§] | 6032684 | 10.0 | 15.7 | 11.3 | 11.5 | 44.02 |
| P23 Plasma DNA[§] | 6642795 | 5.3 | 12.2 | 9.6 | — | 43.80 |
| P26 Plasma DNA[§] | 3851477 | 10.3 | 18.2 | 14.2 | — | 42.51 |
| P31 Plasma DNA[§] | 4683777 | Missing data[‡] | 13.2 | 17.0 | — | 48.27 |
| P40 Plasma DNA[§] | 4187561 | 8.6 | 20.0 | 17.1 | — | 42.65 |
| P42 Plasma DNA[§] | 4315527 | <4.4[‡] | 9.7 | 7.9 | — | 44.14 |
| P52 Plasma DNA[§] | 5126837 | 6.3 | 25.0 | 26.3 | 26.4 | 44.34 |
| P53 Plasma DNA[§] | 5434222 | — | — | — | 25.8 | 44.18 |
| P57 Plasma DNA[§] | 7470487 | — | — | — | 23.0 | 42.89 |
| P59 Plasma DNA[§] | 6684871 | 26.4 | 44.0 | 39.8 | 45.1 | 43.64 |
| P64 Plasma DNA[§] | 6701148 | <4.4[‡] | 14.0 | 8.9 | 16.7 | 44.21 |
| Male Donor Plasma DNA[§] | 3692931 | — | — | — | — | 48.30 |
| Male Donor Whole Blood Genomic DNA[§] | 5085412 | — | — | — | — | 46.53 |
| P25 Plasma DNA[¶] | 144992[†] | — | — | — | — | 41.38 |
| P13 Plasma DNA[§] | 2835333 | 9.8 | 5.7 | n/a[‖] | — | 39.60 |

The volume of plasma is the volume used for Sequencing Library Creation (ml). The amount of DNA is in Plasma (cell equivalent/ml plasma)*. The approximate amount of input DNA is that use for Sequencing Library Construction (ng).
*As quantified by digital PCR with EIF2C1 Taqman Assay, converting from copies to ng assuming 6.6 pg/cell equivalent.
[†]For 454 sequencing, this number represents the number of reads with at least 90% accuracy and 90% coverage when mapped to hg18.
[‡]Insufficient materials were available for quantifying fetal DNA % with digital PCR for these samples (either no samples remained for analysis or there was insufficient sampling).
[§]Sequenced on Solexa/Illumina platform;
[¶]Sequenced on 454/Roche platform
[‖]Sample P13 was the first to be analyzed by shotgun sequencing. It was a normal fetus and the chromosome value was clearly disomic. However, there were some irregularities with this sample and it was not included in further analysis. This sample was sequenced on a different Solexa instrument than the rest of the samples of this study, and it was sequenced in the presence of a number of samples of unknown origin. The G/C content of this sample was lower than the G/C bias of the human genome, while the rest of the samples are above. It had the lowest number of reads, and also the smallest number of reads mapped successfully to the human genome. This sample appeared to be outlier in sequence tag density for most chromosomes and the fetal DNA fraction calculated from chromosomes X was not well defined. For these reasons we suspect that the irregularities are due to technical problems with the sequencing process.

In Table 1 and Table 2, each sample represents a different patient, e.g., P1 in the first row. The total number of sequence tags varied but was frequently was in the 10 million range, using the Solexa technology. The 454 technology used for P25 and P13 gave a lower number of reads.

Figure 5A:
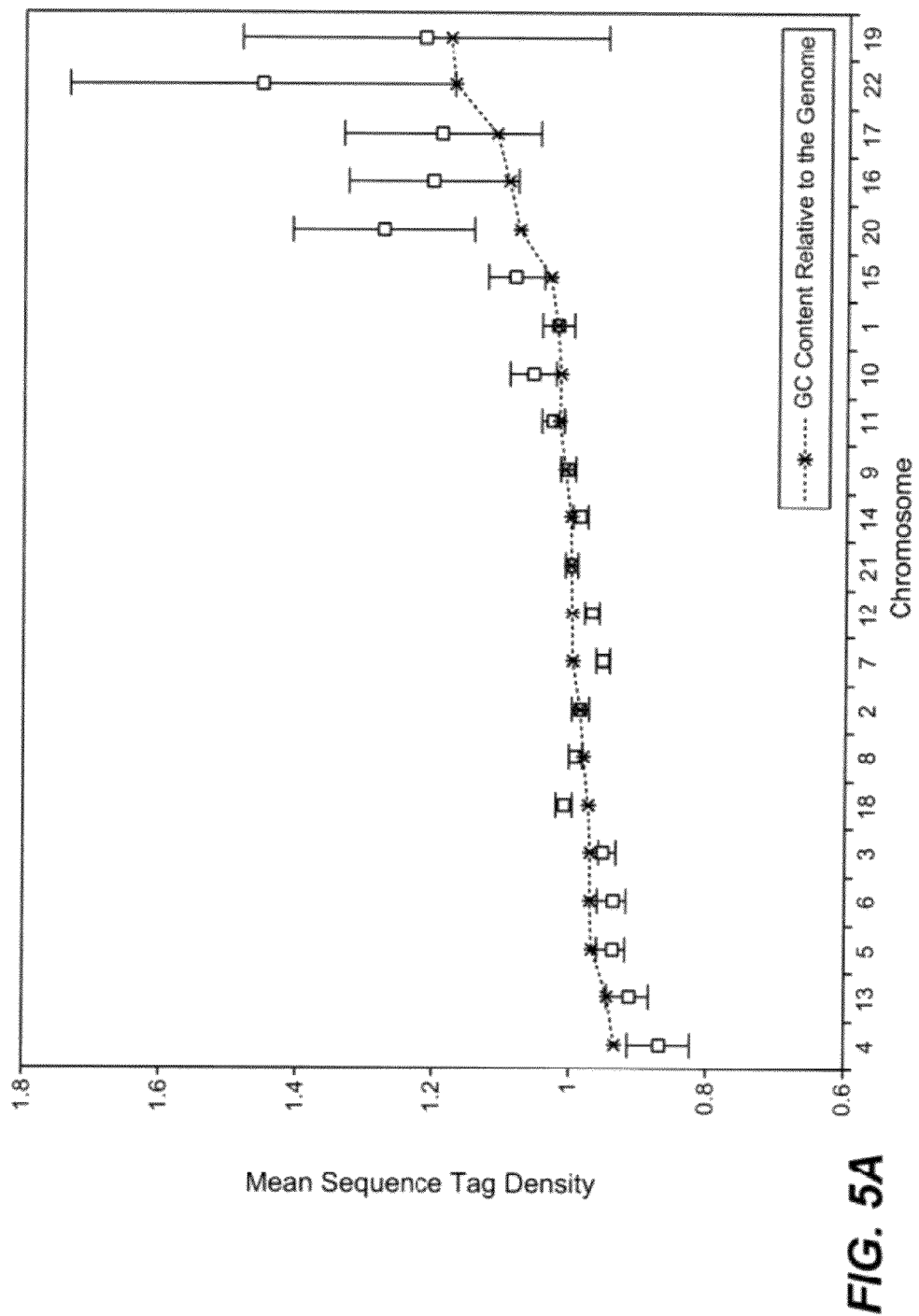
FIG. 5A is a scatter plot graph showing the mean sequence tag density for each chromosome of all samples, including cell-free plasma DNA from pregnant women and male donor, as well as genomic DNA control from male donor, is plotted above. Exceptions are chromosomes 13, 18 and 21, where cell-free DNA samples from women carrying aneuploid fetuses are excluded. The error bars represent standard deviation. The chromosomes are ordered by their G/C content. G/C content of each chromosome relative to the genome-wide value (41%) is also plotted.
Figure 5B:
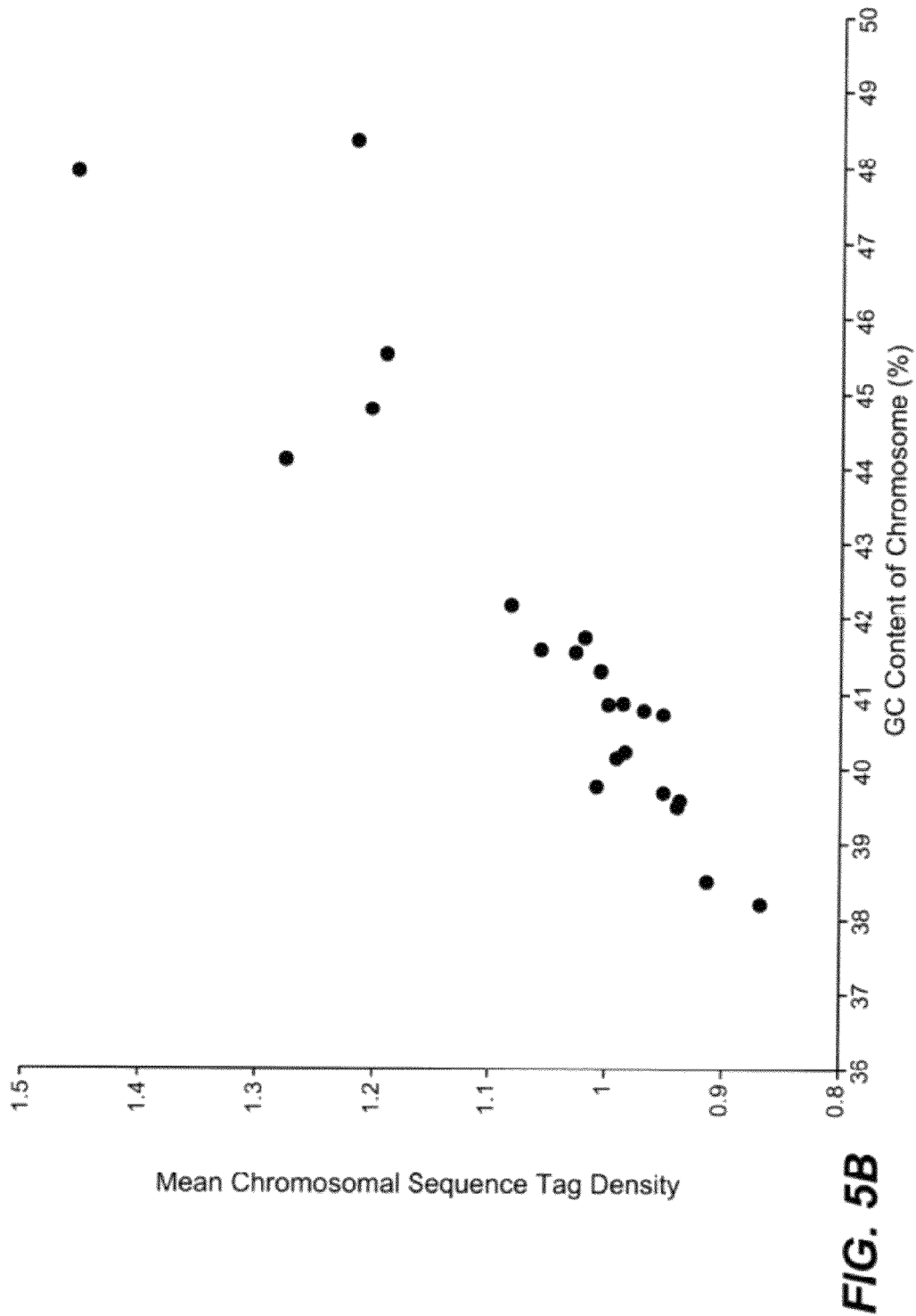
FIG. 5B is a scatter plot of mean sequence tag density for each chromosome versus G/C content of the chromosome. The correlation coefficient is 0.927, and the correlation is statistically significant ($p<10^{-9}$).
Figure 5C:
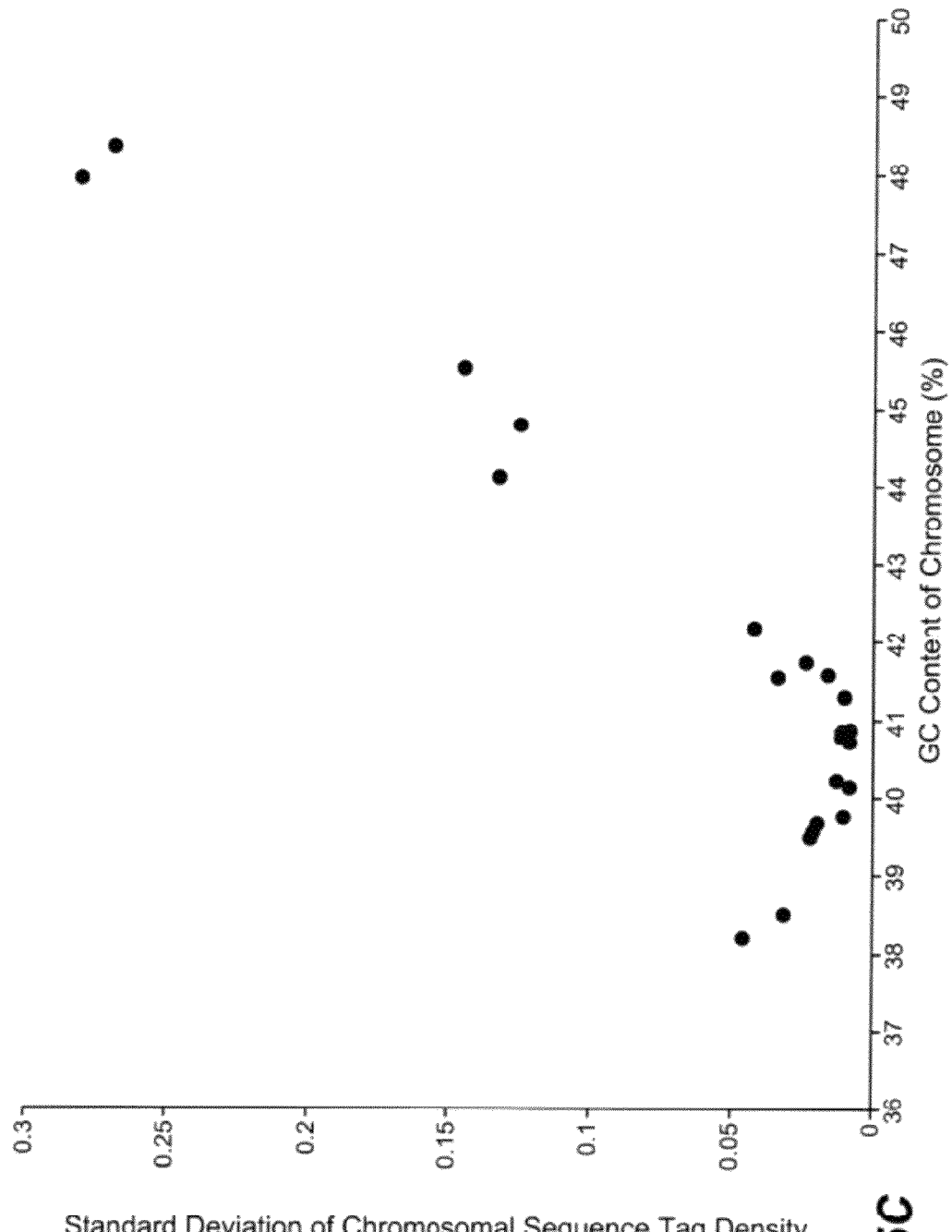
FIG. 5C is a scatter plot of the standard deviation of sequence tag density of each chromosome versus G/C content of the chromosome. The correlation coefficient between standard deviation of sequence tag density and the absolute deviation of chromosomal G/C content from the genome-wide G/C content is 0.963, and the correlation is statistically significant (p<10-12).
Figure 6:
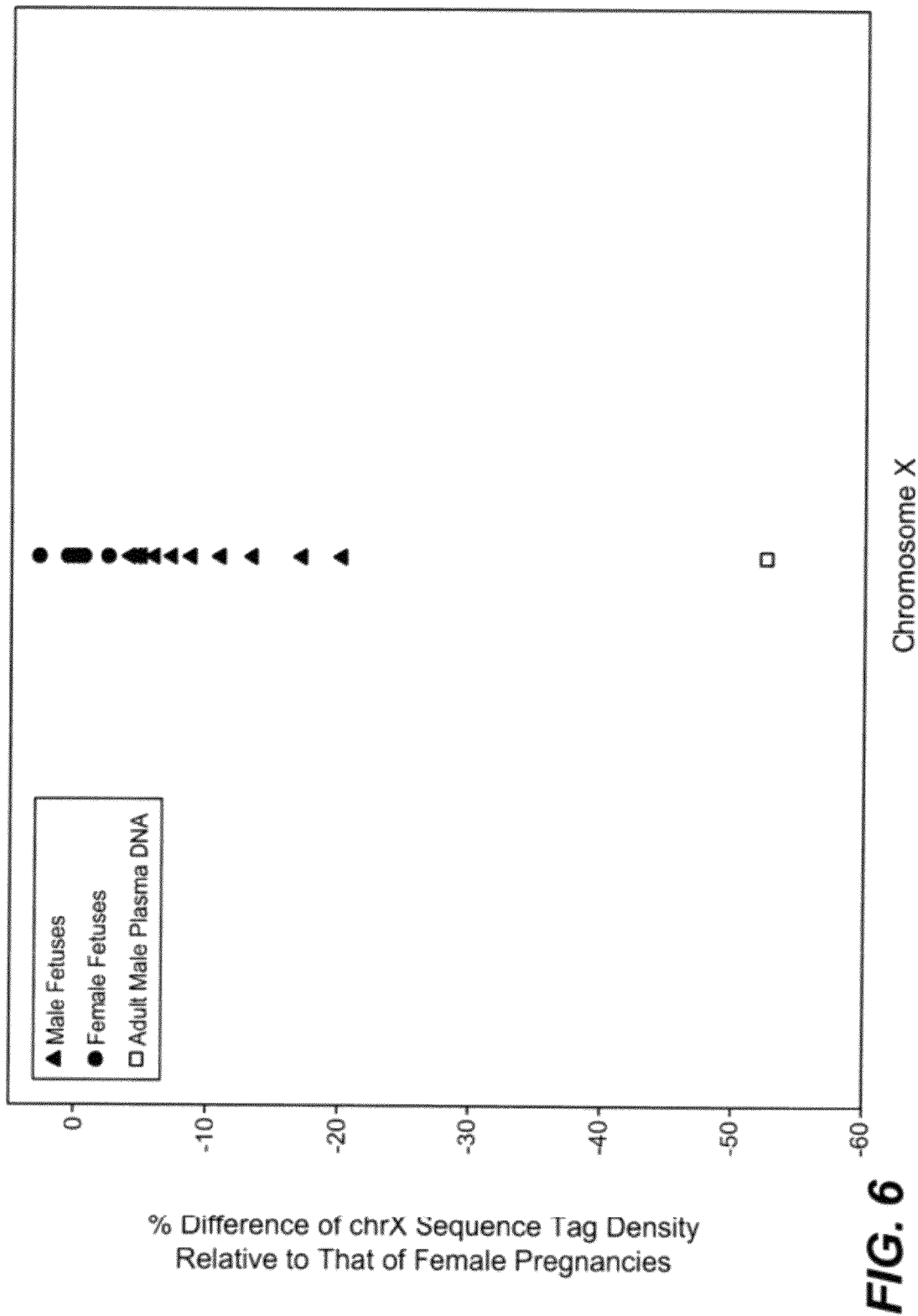
FIG. 6 is a scatter plot graph showing percent difference of chromosome X sequence tag density of all samples as compared to the median chromosome X sequence tag density of all female pregnancies. All male pregnancies show under-representation of chromosome X.

We observed a non-uniform distribution of sequence tags across each chromosome. This pattern of intra-chromosomal variation was common among all samples, including randomly sheared genomic DNA, indicating the observed variation was most probably due to sequencing artifacts. We applied an arbitrary sliding window of 50 kb across each chromosome and counted the number of tags falling within each window. The window can be varied in size to account for larger numbers of reads (in which cases a smaller window, e.g., 10 kb, gives a more detailed picture of a chromosome) or a smaller number of reads, in which case a larger window (e.g., 100 kb) may still be used and will detect gross chromosome deletions, omissions or duplications. The median count per 50 kb window for each chromosome was selected. The median of the autosomal values (i.e., 22 chromosomes) was used as a normalization constant to account for the differences in total number of sequence tags obtained for different samples. The inter-chromosomal variation within each sample was also consistent among all samples (including genomic DNA control). The mean sequence tag density of each chromosome correlates with the G/C content of the chromosome ($p<10^{-9}$) (FIG. 5A, 5B). The standard deviation of sequence tag density for each chromosome also correlates with the absolute degree of deviation in chromosomal G/C content from the genome-wide G/C content ($p<10^{-12}$) (FIG. 5A, 5C). The G/C content of sequenced tags of all samples (including the genomic DNA control) was on average 10% higher than the value of the sequenced human genome (41%) (21) (Table 2), suggesting that there is a strong G/C bias stemming from the sequencing process. We plotted in FIG. 1A the sequence tag density for each chromosome (ordered by increasing G/C content) relative to the corresponding value of the genomic DNA control to remove such bias.

Detection of Fetal Aneuploidy

Figure 1A:
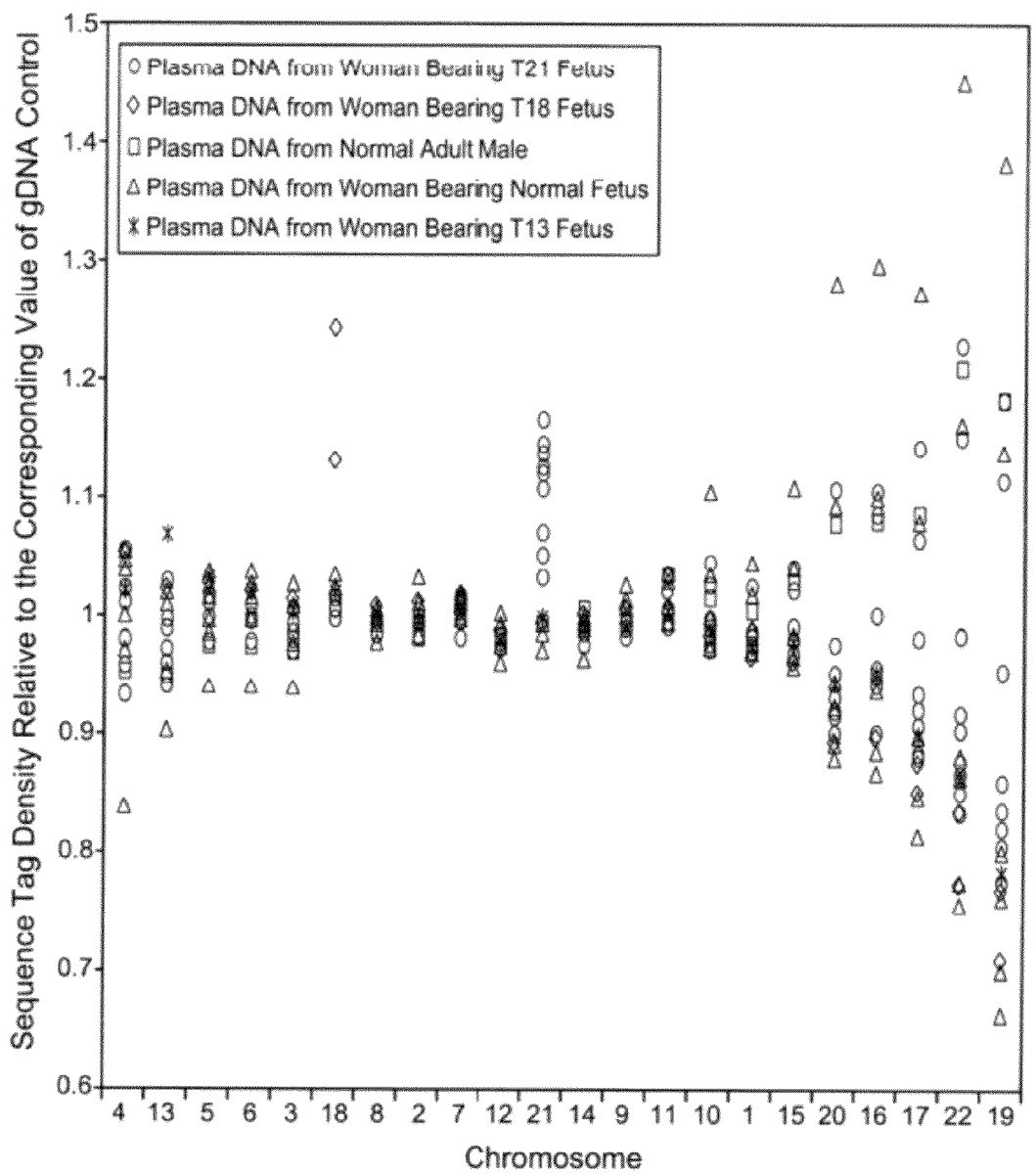
FIG. 1A shows sequence tag density relative to the corresponding value of genomic DNA control; chromosomes are ordered by increasing G/C content. The samples shown as indicated, are plasma from a woman bearing a T21 fetus; plasma from a woman bearing a T18 fetus; plasma from a normal adult male; plasma from a woman bearing a normal fetus; plasma from a woman bearing a T13 fetus. Sequence tag densities vary more with increasing chromosomal G/C content.
Figure 1B:
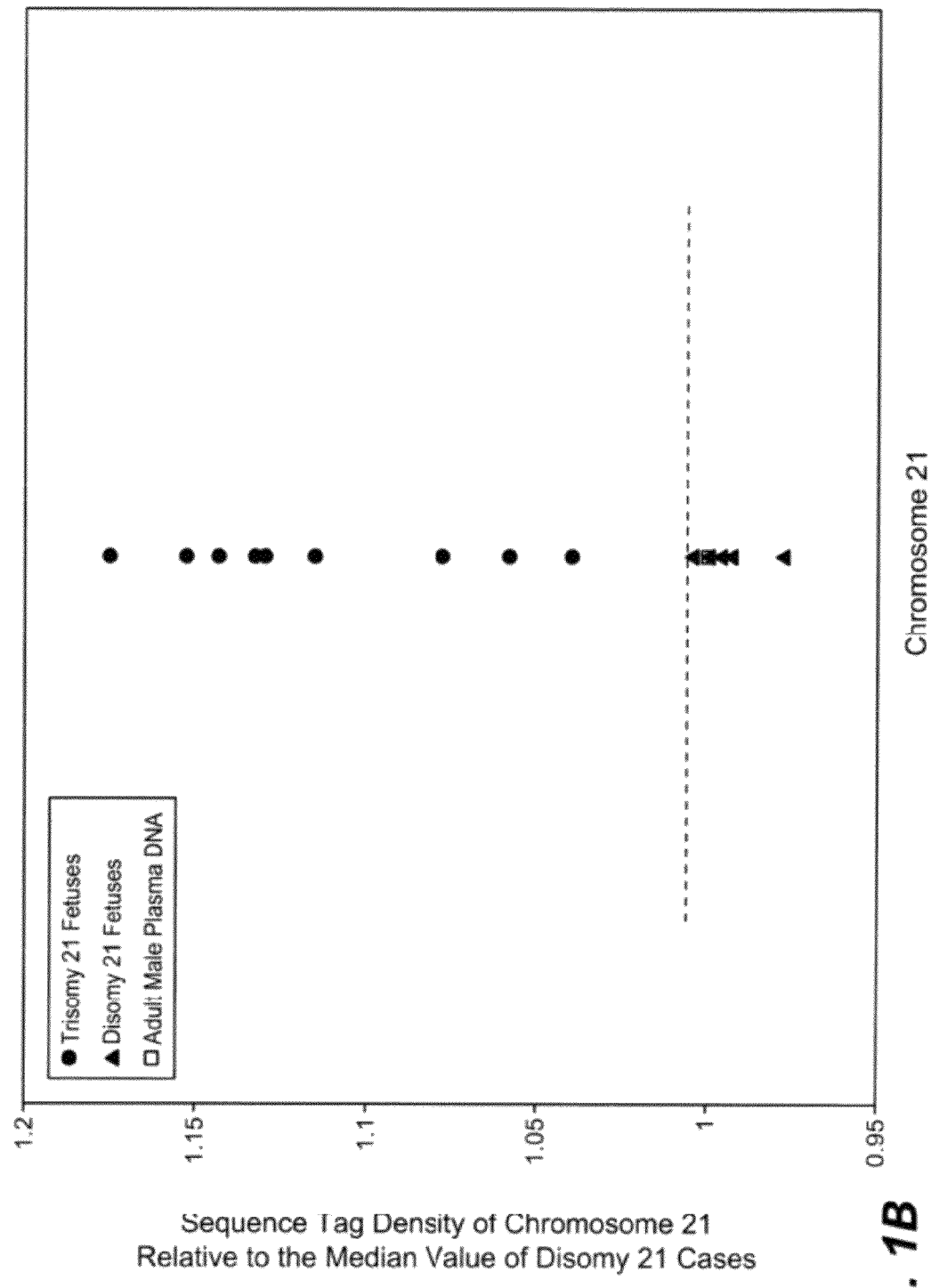
FIG. 1B is a detail from FIG. 1A, showing chromosome 21 sequence tag density relative to the median chromosome 21 sequence tag density of the normal cases. Note that the values of 3 disomy 21 cases overlap at 1.0. The dashed line represents the upper boundary of the 99% confidence interval constructed from all disomy 21 samples. The chromosomes are listed in FIG. 1A in order of G/C content, from low to high. This figure suggests that one would prefer to use as a reference chromosome in the mixed sample with a mid level of G/C content, as it can be seen that the data there are more tightly grouped. That is, chromosomes 18, 8, 2, 7, 12, 21 (except in suspected Down syndrome), 14, 9, and 11 may be used as the nominal diploid chromosome if looking for a trisomy.

The distribution of chromosome 21 sequence tag density for all 9 T21 pregnancies is clearly separated from that of pregnancies bearing disomy 21 fetuses ($p<10^{-5}$), Student's t-test) (FIGS. 1A and 1B). The coverage of chromosome 21 for T21 cases is about ~4-18% higher (average ~11%) than that of the disomy 21 cases. Because the sequence tag density of chromosome 21 for T21 cases should be $(1+\epsilon/2)$ of that of disomy 21 pregnancies, where $\epsilon$ is the fraction of total plasma DNA originating from the fetus, such increase in chromosome 21 coverage in T21 cases corresponds to a fetal DNA fraction of ~8%-35% (average ~23%) (Table 1, FIG. 2). We constructed a 99% confidence interval of the distribution of chromosome 21 sequence tag density of disomy 21 pregnancies. The values for all 9 T21 cases lie outside the upper boundary of the confidence interval and those for all 9 disomy 21 cases lie below the boundary (FIG. 1B). If we used the upper bound of the confidence interval as a threshold value for detecting T21, the minimum fraction of fetal DNA that would be detected is ~2%.

Plasma DNA of pregnant women carrying T18 fetuses (2 cases) and a T13 fetus (1 case) were also directly sequenced. Over-representation was observed for chromosome 18 and chromosome 13 in T18 and T13 cases respectively (FIG. 1A). While there were not enough positive samples to measure a representative distribution, it is encouraging that all of these three positives are outliers from the distribution of disomy values. The T18 are large outliers and are clearly statistically significant ($p<10^{-7}$), while the statistical significance of the single T13 case is marginal ($p<0.05$). Fetal DNA fraction was also calculated from the over-represented chromosome as described above (FIG. 2, Table 1).

Fetal DNA Fraction in Maternal Plasma

Using digital Taqman PCR for a single locus on chromosome 1, we estimated the average cell-free DNA concentration in the sequenced maternal plasma samples to be ~360 cell equivalent/ml of plasma (range: 57 to 761 cell equivalent/ml plasma) (Table 1), in rough accordance to previously reported values (13). The cohort included 12 male pregnancies (6 normal cases, 4 T21 cases, 1 T18 case and 1 T13 case) and 6 female pregnancies (5 T21 cases and 1 T18 case). DYS14, a multi-copy locus on chromosome Y, was detectable in maternal plasma by real-time PCR in all these pregnancies but not in any of the female pregnancies (data not shown). The fraction of fetal DNA in maternal cell-free plasma DNA is usually determined by comparing the amount of fetal specific locus (such as the SRY locus on chromosome Y in male pregnancies) to that of a locus on any autosome that is common to both the mother and the fetus using quantitative real-time PCR (13, 22, 23). We applied a similar duplex assay on a digital PCR platform (see Methods) to compare the counts of the SRY locus and a locus on chromosome 1 in male pregnancies. SRY locus was not detectable in any plasma DNA samples from female pregnancies. We found with digital PCR that for the majority samples, fetal DNA constituted §10% of total DNA in maternal plasma (Table 2), agreeing with previously reported values (13).

The percentage of fetal DNA among total cell-free DNA in maternal plasma can also be calculated from the density of sequence tags of the sex chromosomes for male pregnancies. By comparing the sequence tag density of chromosome Y of plasma DNA from male pregnancies to that of adult male plasma DNA, we estimated fetal DNA percentage to be on average ~19% (range: 4-44%) for all male pregnancies (Table 2, above, FIG. 2). Because human males have 1 fewer chromosome X than human females, the sequence tag density of chromosome X in male pregnancies should be $(1-e/2)$ of that of female pregnancies, where e is fetal DNA fraction. We indeed observed under-representation of chromosome X in male pregnancies as compared to that of female pregnancies (FIG. 5). Based on the data from chromosome X, we estimated fetal DNA percentage to be on average ~19% (range: 8-40%) for all male pregnancies (Table 2, above, FIG. 2). The fetal DNA percentage estimated from chromosomes X and Y for each male pregnancy sample correlated with each other ($p=0.0015$) (FIG. 7).

Figure 2:
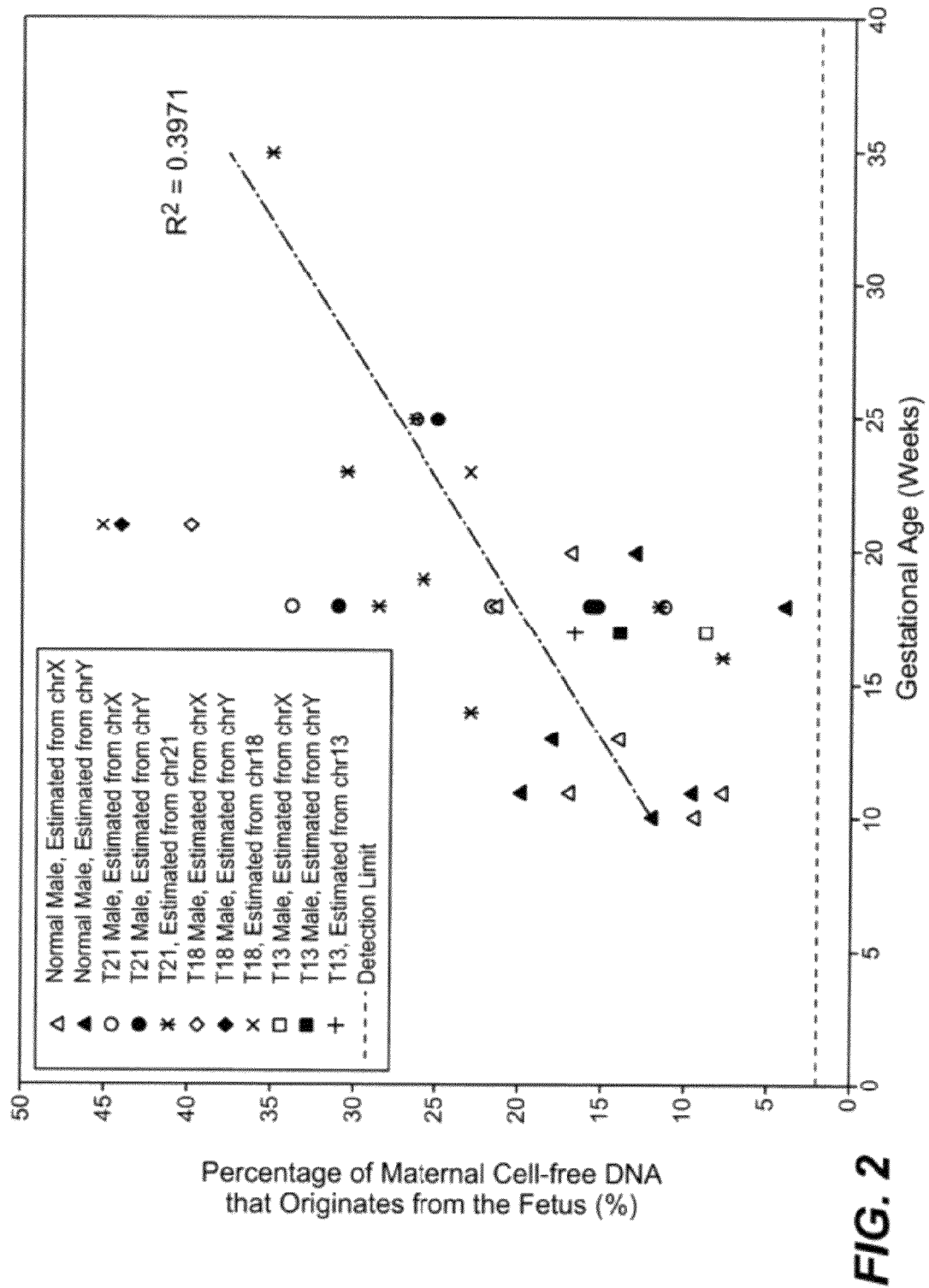
FIG. 2 is a scatter plot graph showing fetal DNA fraction and gestational age. The fraction of fetal DNA in maternal plasma correlates with gestational age. Fetal DNA fraction was estimated by three different ways: 1. From the additional amount of chromosomes 13, 18, and 21 sequences for T13, T18, and T21 cases respectively. 2. From the depletion in amount of chromosome X sequences for male cases. 3. From the amount of chromosome Y sequences present for male cases. The horizontal dashed line represents the estimated minimum fetal DNA fraction required for the detection of aneuploidy. For each sample, the values of fetal DNA fraction calculated from the data of different chromosomes were averaged. There is a statistically significant correlation between the average fetal DNA fraction and gestational age (p=0.0051). The dashed line represents the simple linear regression line between the average fetal DNA fraction and gestational age. The R2 value represents the square of the correlation coefficient.

We plotted in FIG. 2 the fetal DNA fraction calculated from the over-representation of trisomic chromosome in aneuploid pregnancies, and the under-representation of chromosome X and the presence of chromosome Y for male pregnancies against gestational age. The average fetal DNA fraction for each sample correlates with gestational age ($p=0.0051$), a trend that is also previously reported (13).

Size Distribution of Cell-Free Plasma DNA

We analyzed the sequencing libraries with a commercial lab-on-a-chip capillary electrophoresis system. There is a striking consistency in the peak fragment size, as well as the distribution around the peak, for all plasma DNA samples, including those from pregnant women and male donor. The peak fragment size was on average 261 bp (range: 256-264 bp). Subtracting the total length of the Solexa adaptors (92 bp) from 260 bp gives 169 bp as the actual peak fragment size. This size corresponds to the length of DNA wrapped in a chromatosome, which is a nucleosome bound to a H1 histone (24). Because the library preparation includes an 18-cycle PCR, there are concerns that the distribution might be biased.

Figure 3:
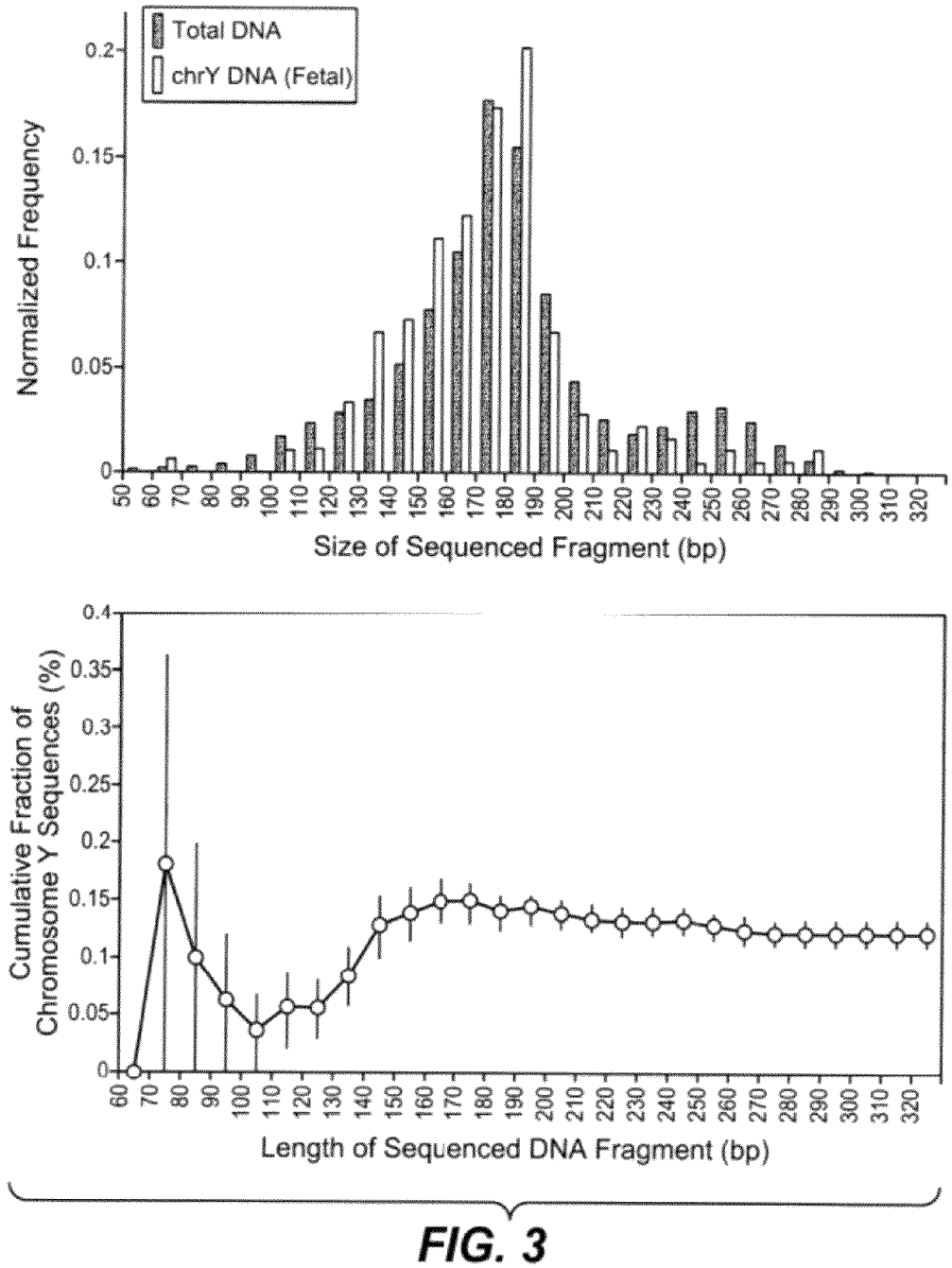
FIG. 3 is a histogram showing size distribution of maternal and fetal DNA in maternal plasma. It shows the size distribution of total and chromosome Y specific fragments obtained from 454 sequencing of maternal plasma DNA from a normal male pregnancy. The distribution is normalized to sum to 1. The numbers of total reads and reads mapped to the Y-chromosome are 144992 and 178 respectively. Inset: Cumulative fetal DNA fraction as a function of sequenced fragment size. The error bars correspond to the standard error of the fraction estimated assuming the error of the counts of sequenced fragments follow Poisson statistics.
Figure 8:
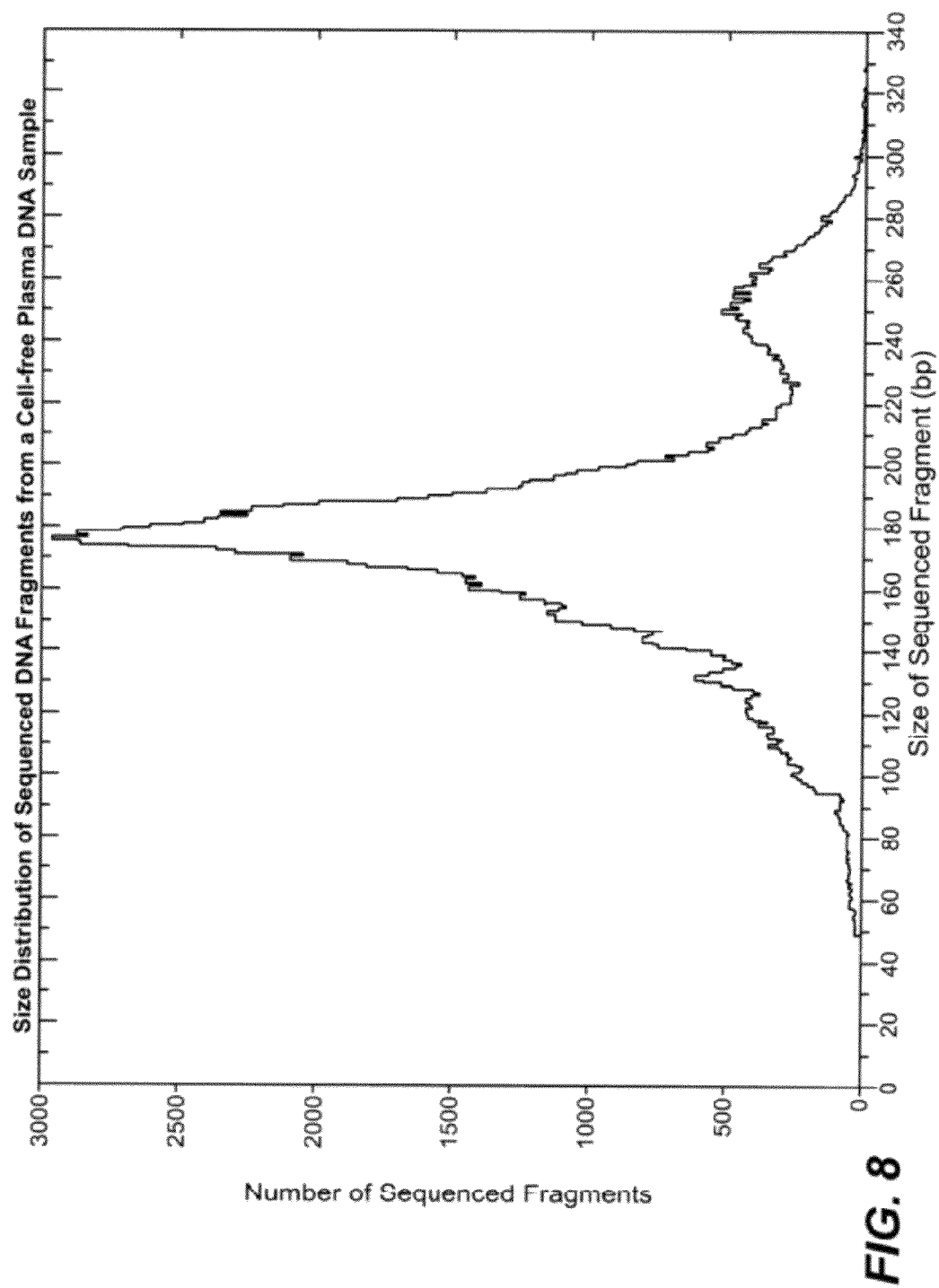
FIG. 8 is a line graph showing length distribution of sequenced fragments from maternal cell-free plasma DNA sample of a normal male pregnancy at 1bp resolution. Sequencing was done on the 454/Roche platform. Reads that have at least 90% mapping to the human genome with greater than or equal to 90% accuracy are retained, totaling 144992 reads. Y-axis represents the number of reads obtained. The median length is 177 bp while the mean length is 180 bp.
Figure 9A:
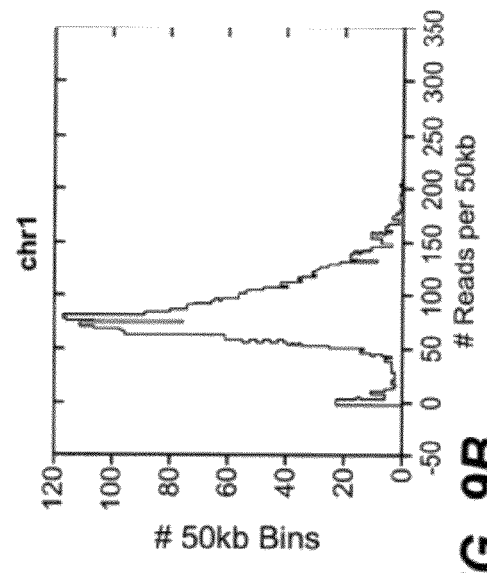
FIG. 9 is a schematic illustrating how sequence tag distribution is used to detect the over and under-representation of any chromosome, i.e., a trisomy (over representation) or a missing chromosome (typically an X or Y chromosome, since missing autosomes are generally lethal). As shown in left panels A and C, one first plots the number of reads obtained versus a window that is mapped to a chromosome coordinate that represents the position of the read along the chromosome. That is, chromosome 1 (panel A) can be seen to have about $2.8 \times 10^8$ bp. It would have this number divided by 50 kb windows. These values are replotted (panels B and D) to show the distribution of the number of sequence tags/50 kb window. The term "bin" is equivalent to a window. From this analysis, one can determine a median number of reads M for each chromosome, which, for purposes of illustration, may be observed along the x axis at the approximate center of the distribution and may be said to be higher if there are more sequence tags attributable to that chromosome. For chromosome 1, illustrated in panels A and B, one obtains a median M1. By taking the median M of all 22 autosomes, one obtains a normalization constant N that can be used to correct for differences in sequences obtained in different runs, as can be seen in Table 1. Thus, the normalized sequence tag density for chromosome 1 would be M1/N; for chromosome 22 it would be M22/N. Close examination of panel A, for example would show that towards the zero end of the chromosome, this procedure obtained about 175 reads per 50 kb window. In the middle, near the centromere, there were no reads, because this portion of the chromosome is ill defined in the human genome library.
Figure 9B:
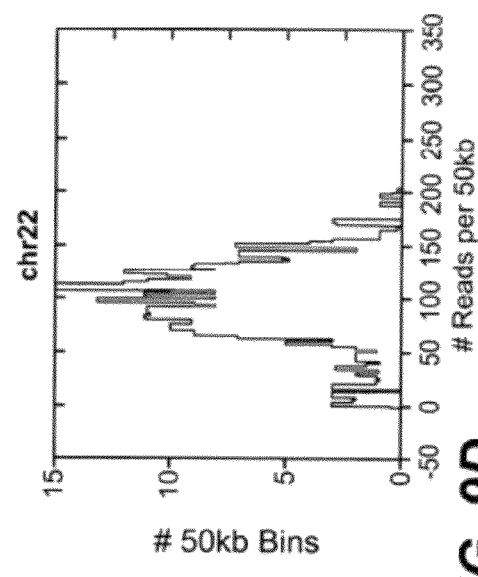
Figure 9C:
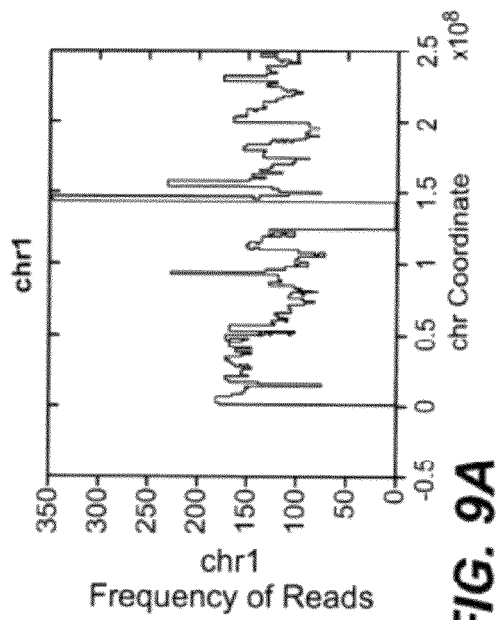
Figure 9D:
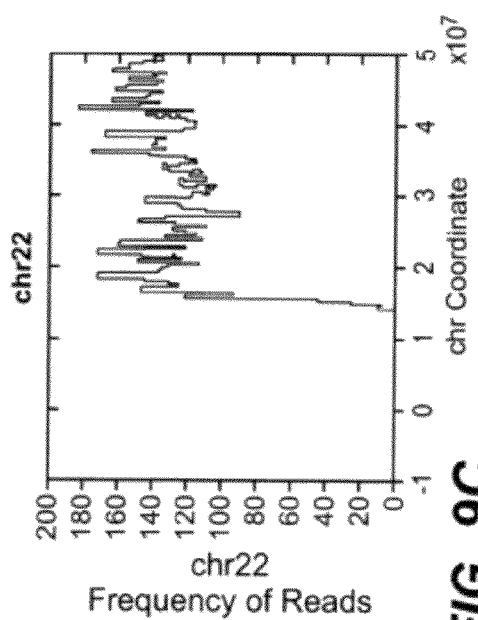

To verify that the size distribution observed in the electropherograms is not an artifact of PCR, we also sequenced cell-free plasma DNA from a pregnant woman carrying a male fetus using the 454 platform. The sample preparation for this system uses emulsion PCR, which does not require competitive amplification of the sequencing libraries and creates product that is largely independent of the amplification efficiency. The size distribution of the reads mapped to unique locations of the human genome resembled those of the Solexa sequencing libraries, with a predominant peak at 176 bp, after subtracting the length of 454 universal adaptors (FIG. 3 and FIG. 8). These findings suggest that the majority of cell-free DNA in the plasma is derived from apoptotic cells, in accordance with previous findings (22, 23, 25, 26).

Of particular interest is the size distribution of maternal and fetal DNA in maternal cell-free plasma. Two groups have previously shown that the majority of fetal DNA has size range of that of mono-nucleosome (<200-300 bp), while maternal DNA is longer. Because 454 sequencing has a targeted read-length of 250 bp, we interpreted the small peak at around 250 bp (FIG. 3 and FIG. 8) as the instrumentation limit from sequencing higher molecular weight fragments. We plotted the distribution of all reads and those mapped to Y-chromosome (FIG. 3). We observed a slight depletion of Y-chromosome reads in the higher end of the distribution. Reads <220 bp constitute 94% of Y-chromosome and 87% of the total reads. Our results are not in complete agreement with previous findings in that we do not see as dramatic an enrichment of fetal DNA at short lengths (22, 23). Future studies will be needed to resolve this point and to eliminate any potential residual bias in the 454 sample preparation process, but it is worth noting that the ability to sequence single plasma samples permits one to measure the distribution in length enrichments across many individual patients rather than measuring the average length enrichment of pooled patient samples.

Cell-Free Plasma DNA Shares Features of Nucleosomal DNA

Since our observations of the size distribution of cell-free plasma DNA suggested that plasma DNA is mainly apoptotic of origin, we investigated whether features of nucleosomal DNA and positioning are found in plasma DNA. One such feature is nucleosome positioning around transcription start sites. Experimental data from yeast and human have suggested that nucleosomes are depleted in promoters upstream of transcription start sites and nucleosomes are well-positioned near transcription start sites (27-30). We applied a 5 bp window spanning +/−1000 bp of transcription start sites of all RefSeq genes and counted the number of tags mapping to the sense and antisense strands within each window. A peak in the sense strand represents the beginning of a nucleosome while a peak in the antisense strand represents the end. After smoothing, we saw that for most plasma DNA samples, at least 3 well-positioned nucleosomes downstream of transcription start sites could be detected, and in some cases, up to 5 well-positioned nucleosomes could be detected, in rough accordance to the results of Schones et al. (27) (FIG. 4). We applied the same analysis on sequence tags of randomly sheared genomic DNA and observed no obvious pattern in tag localization, although the density of tags was higher at the transcription start site (FIG. 4).

Correction for Sequencing Bias

Shown in FIGS. 10 and 12 are results which may be obtained when sequence tag numbers are treated statistically based on data from the reference human genome. That is, for example, sequence tags from fragments with higher GC content may be overrepresented, and suggest an aneuploidy where none exists. The sequence tag information itself may not be informative, since only a small portion of the fragment ordinarily will be sequenced, while it is the overall G/C content of the fragment that causes the bias. Thus there is provided a method, described in detail in Examples 8 and 10, for correcting for this bias, and this method may facilitate analysis of samples which otherwise would not produce statistically significant results. This method, for correcting for G/C bias of sequence reads from massively parallel sequencing of a genome, comprises the step of dividing the genome into a number of windows within each chromosome and calculating the G/C content of each window. These windows need not be the same as the windows used for calculating sequence tag density; they may be on the order of 10 kb-30 kb in length, for example. One then calculates the relationship between sequence coverage and G/C content of each window by determining a number of reads per a given window and a G/C content of that window. The G/C content of each window is known from the human genome reference sequence. Certain windows will be ignored, i.e., with no reads or no G/C content. One then assigns a weight to the number of reads per a given window (i.e., the number of sequence tags assigned to that window) based on G/C content, where the weight has a relationship to G/C content such that increasing numbers of reads with increasing G/C content results in decreasing weight per increasing G/C content.

EXAMPLES

The examples below describe the direct sequencing of cell-free DNA from plasma of pregnant women with high throughput shotgun sequencing technology, obtaining on average 5 million sequence tags per patient sample. The sequences obtained were mapped to specific chromosomal locations. This enabled us to measure the over- and under-representation of chromosomes from an aneuploid fetus. The sequencing approach is polymorphism-independent and therefore universally applicable for the non-invasive detection of fetal aneuploidy. Using this method we successfully identified all 9 cases of trisomy 21 (Down syndrome), 2 cases of trisomy 18 and 1 case of trisomy 13 in a cohort of 18 normal and aneuploid pregnancies; trisomy was detected at gestational ages as early as the 14th week. Direct sequencing also allowed us to study the characteristics of cell-free plasma DNA, and we found evidence that this DNA is enriched for sequences from nucleosomes.

Example 1

Subject Enrollment

The study was approved by the Institutional Review Board of Stanford University. Pregnant women at risk for fetal aneuploidy were recruited at the Lucile Packard Children Hospital Perinatal Diagnostic Center of Stanford University during the period of April 2007 to May 2008. Informed consent was obtained from each participant prior to the blood draw. Blood was collected 15 to 30 minutes after amniocentesis or chorionic villus sampling except for 1 sample that was collected during the third trimester. Karyotype analysis was performed via amniocentesis or chorionic villus sampling to confirm fetal karyotype. 9 trisomy 21 (T21), 2 trisomy 18 (T18), 1 trisomy 13 (T13) and 6 normal singleton pregnancies were included in this study. The gestational age of the subjects at the time of blood draw ranged from 10 to 35 weeks (Table 1). Blood sample from a male donor was obtained from the Stanford Blood Center.

Example 2

Sample Processing and DNA Quantification 7 to 15 ml of peripheral blood drawn from each subject and donor was collected in EDTA tubes. Blood was centrifuged at 1600 g for 10 minutes. Plasma was transferred to microcentrifuge tubes and centrifuged at 16000 g for 10 minutes to remove residual cells. The two centrifugation steps were performed within 24 hours after blood collection. Cell-free plasma was stored at −80 C until further processing and was frozen and thawed only once before DNA extraction. DNA was extracted from cell-free plasma using QIAamp DNA Micro Kit (Qiagen) or NucleoSpin Plasma Kit (Macherey-Nagel) according to manufacturers' instructions. Genomic DNA was extracted from 2000 whole blood of the donors using QIAamp DNA Blood Mini Kit (Qiagen). Microfluidic digital PCR (Fluidigm) was used to quantify the amount of total and fetal DNA using Taqman assays targeting at the EIF2C1 locus on chromosome 1 (Forward: 5' GTTCGGCTTTCACCAGTCT 3' (SEQ ID NO: 1); Reverse: 5' CTCCATAGCTCTCCCCACTC 3' (SEQ ID NO: 2); Probe: 5' HEX-GCCCTGCCATGTGGAAGAT-BHQ1 3' (SEQ ID NO: 3); amplicon size: 81 bp) and the SRY locus on chromosome Y (Forward: 5' CGCTTAACATAGCAGAAGCA 3' (SEQ ID NO: 4); Reverse: 5' AGTTTCGAACTCTGGCACCT 3' (SEQ ID NO: 5); Probe: 5' FAM-TGTCGCACTCTCCTTGTTTTTGACA-BHQ1 3' (SEQ ID NO: 6); amplicon size: 84 bp) respectively. A Taqman assay targeting at DYS14 (Forward: 5' ATCGTCCATTTCCAGAATCA 3' (SEQ ID NO: 7); Reverse: 5' GTTGACAGCCGTGGAATC 3' (SEQ ID NO: 8); Probe: 5' FAM-TGCCACAGACTGAACTGAATGATTTTC-BHQ1 3' (SEQ ID NO: 9); amplicon size: 84 bp), a multi-copy locus on chromosome Y, was used for the initial determination of fetal sex from cell-free plasma DNA with traditional real-time PCR. PCR reactions were performed with 1×iQ Supermix (Bio-Rad), 0.1% Tween-20 (microfluidic digital PCR only), 300 nM primers, and 150 nM probes. The PCR thermal cycling protocol was 95 C for 10 min, followed by 40 cycles of 95 C for 15 s and 60 C for 1 min. Primers and probes were purchased form IDT.

Example 3

Sequencing

A total of 19 cell-free plasma DNA samples, including 18 from pregnant women and 1 from a male blood donor, and genomic DNA sample from whole blood of the same male donor, were sequenced on the Solexa/Illumina platform. ~1 to 8 ng of DNA fragments extracted from 1.3 to 5.6 ml cell-free plasma was used for sequencing library preparation (Table 1). Library preparation was carried out according to manufacturer's protocol with slight modifications. Because cell-free plasma DNA was fragmented in nature, no further fragmentation by nebulization or sonication was done on plasma DNA samples.

Genomic DNA from male donor's whole blood was sonicated (Misonix XL-2020) (24 cycles of 30 s sonication and 90 s pause), yielding fragments with size between 50 and 400 bp, with a peak at 150 bp. ~2 ng of the sonicated genomic DNA was used for library preparation. Briefly, DNA samples were blunt ended and ligated to universal adaptors. The amount of adaptors used for ligation was 500 times less than written on the manufacturer's protocol. 18 cycles of PCR were performed to enrich for fragments with adaptors using primers complementary to the adaptors. The size distributions of the sequencing libraries were analyzed with DNA 1000 Kit on the 2100 Bioanalyzer (Agilent) and quantified with microfluidic digital PCR (Fluidigm). The libraries were then sequenced using the Solexa 1G Genome Analyzer according to manufacturer's instructions.

Cell-free plasma DNA from a pregnant woman carrying a normal male fetus was also sequenced on the 454/Roche platform. Fragments of DNA extracted from 5.6 ml of cell-free plasma (equivalent to ~4.9 ng of DNA) were used for sequencing library preparation. The sequencing library was prepared according to manufacturer's protocol, except that no nebulization was performed on the sample and quantification was done with microfluidic digital PCR instead of capillary electrophoresis. The library was then sequenced on the 454 Genome Sequencer FLX System according to manufacturer's instructions.

Electropherograms of Solexa sequencing libraries were prepared from cell-free plasma DNA obtained from 18 pregnant women and 1 male donor. Solexa library prepared from sonicated whole blood genomic DNA from the male donor was also examined. For libraries prepared from cell-free DNA, all had peaks at average 261 bp (range: 256-264 bp). The actual peak size of DNA fragments in plasma DNA is ~168 bp (after removal of Solexa universal adaptor (92 bp)). This corresponds to the size of a chromatosome.

Example 4

Data Analysis

Shotgun Sequence Analysis

Solexa sequencing produced 36 to 50 bp reads. The first 25 bp of each read was mapped to the human genome build 36 (hg18) using ELAND from the Solexa data analysis pipeline. The reads that were uniquely mapped to the human genome having at most 1 mismatch were retained for analysis. To compare the coverage of the different chromosomes, a sliding window of 50 kb was applied across each chromosome, except in regions of assembly gaps and microsatellites, and the number of sequence tags falling within each window was counted and the median value was chosen to be the representative of the chromosome. Because the total number of sequence tags for each sample was different, for each sample, we normalized the sequence tag density of each chromosome (except chromosome Y) to the median sequence tag density among autosomes. The normalized values were used for comparison among samples in subsequent analysis. We estimated fetal DNA fraction from chromosome 21 for T21 cases, chromosome 18 from T18 cases, chromosome 13 from T13 case, and chromosomes X and Y for male pregnancies. For chromosome 21, 18, and 13, fetal DNA fraction was estimated as $2*(x-1)$, where x was the ratio of the over-represented chromosome sequence tag density of each trisomy case to the median chromosome sequence tag density of the all disomy cases. For chromosome X, fetal DNA was estimated as $2*(1-x)$, where x was the ratio of chromosome X sequence tag density of each male pregnancy to the median chromosome X sequence tag density of all female pregnancies. For chromosome Y, fetal DNA fraction was estimated as the ratio of chromosome Y sequence tag density of each male pregnancy to that of male donor plasma DNA. Because a small number of chromosome Y sequences were detected in female pregnancies, we only considered sequence tags falling within transcribed regions on chromosome Y and subtracted the median number of tags in female pregnancies from all samples; this amounted to a correction of a few percent. The width of 99% confidence intervals was calculated for all disomy 21 pregnancies as t*s/vN, where N is the number of disomy 21 pregnancies, t is the t-statistic corresponding to a=0.005 with degree of freedom equals N−1, and s is the standard deviation. A confidence interval gives an estimated range of values, which is likely to include an unknown population parameter, the estimated range being calculated from a given set of sample data. (Definition taken from Valerie J. Easton and John H. McColl's Statistics Glossary v1.1)

To investigate the distribution of sequence tags around transcription start sites, a sliding window of 5 bp was applied from −1000 bp to +1000 bp of transcription start sites of all RefSeq genes on all chromosomes except chromosome Y. The number of sequence tags mapped to the sense and anti-sense strands within each window was counted. Moving average with a window of 10 data points was used to smooth the data. All analyses were done with Matlab.

We selected the sequence tags that mapped uniquely to the human genome with at most 1 mismatch (on average ~5 million) for analysis. The distribution of reads across each chromosome was examined. Because the distribution of sequence tags across each chromosome was non-uniform (possibly technical artifacts), we divided the length of each chromosome into non-overlapping sliding window with a fixed width (in this particular analysis, a 50 kbp window was used), skipping regions of genome assembly gaps and regions with known microsatellite repeats. The width of the window is should be large enough such that there are a sufficient number of sequence tags in each window, and should be small enough such that there are sufficient number of windows to form a distribution. With increasing sequencing depth (i.e., increasing total number of sequence tags), the window width can be reduced. The number of sequence tags in each window was counted. The distribution of the number of sequence tags per 50 kb for each chromosome was examined. The median value of the number of sequence tags per 50 kb (or 'sequence tag density') for each chromosome was chosen in order to suppress the effects of any under- or over-represented regions within the chromosome. Because the total number of sequence tags obtained for each sample was different, in order to compare among samples, we normalized each chromosomal sequence tag density value (except chromosome Y) by the median sequence tag density among all autosomes (non-sex chromosomes).

For the 454/Roche data, reads were aligned to the human genome build 36 (hg18, see hyper text transfer protocol (http) genome.ucsc.edu/cgi-bin/hgGateway) using the 454 Reference Mapper. Reads having accuracy of greater than or equal to 90% and coverage (i.e., fraction of read mapped) greater than or equal to 90% were retained for analysis. To study the size distribution of total and fetal DNA, the number of retained reads falling within each 10 bp window between 50 bp to 330 bp was counted. The number of reads falling within different size ranges may be studied, i.e., reads of between 50-60 bp, 60-70 bp, 70-80 bp, etc., up to about 320-330 bp, which is around the maximum read length obtained.

Example 5

Genome Data Retrieval

Information regarding G/C content, location of transcription start sites of RefSeq genes, location of assembly gaps and microsatellites were obtained from the UCSC Genome Browser.

Example 6

Nucleosome Enrichment

The distribution of sequence tags around transcription start sites (TSS) of RefSeq genes were analyzed (data not shown). The plots were similar to FIG. 4. Each plot represented the distribution for each plasma DNA or gDNA sample. Data are obtained from three different sequencing runs (P1, P6, P52, P53, P26, P40, P42 were sequenced together; male genomic DNA, male plasma DNA, P2, P7, P14, P19, P31 were sequenced together; P17, P20, P23, P57, P59, P64 were sequenced together). The second batch of samples suffers greater G/C bias as observed from inter- and intra-chromosomal variation. Their distributions around TSS have similar trends with more tags at the TSS. Such trend is not as prominent as in the distributions of samples sequenced in other runs. Nonetheless, at least 3 well-positioned nucleosomes were detectable downstream of transcription start sites for most plasma DNA samples, suggesting that cell-free plasma DNA shares features of nucleosomal DNA, a piece of evidence that this DNA is of apoptotic origin.

Example 7

Calculating Fetal DNA Fraction in Maternal Plasma of Male Pregnancies i. With Digital PCR Taqman Assays Digital PCR is the amplification of single DNA molecule. DNA sample is diluted and distributed across multiple compartments such that on average there is less than 1 copy of DNA per compartment. A compartment displaying fluorescence at the end of a PCR represents the presence of at least one DNA molecule.

Assay for Total DNA: EIF2C1 (Chromosome 1)

Assay for Fetal DNA: SRY (Chromosome Y)

The count of positive compartments from the microfluidic digital PCR chip of each assay is converted to the most probable count according to the method described in the supporting information of the following reference: Warren L, Bryder D, Weissman I L, Quake S R (2006) Transcription factor profiling in individual hematopoietic progenitors by digital RT-PCR. Proc Nat Acad Sci, 103: 17807-12.

Fetal DNA Fraction $\epsilon$=(SRY count)/(EIF2C1 count/2)

ii. With Sequence Tags

From ChrX:

Let fetal DNA fraction be $\epsilon$

| | Maternal Contribution | Male Fetus Contribution | Female Fetus Contribution |
|---|---|---|---|
| ChrX | $2(1-\epsilon)$ | $\epsilon$ | $2\epsilon$ |

Male pregnancies ChrX sequence tag density (fetal and maternal)=$2(1-\epsilon)+\epsilon=2-\epsilon$ Female pregnancies ChrX sequence tag density (fetal and maternal)=$2(1-\epsilon)+2\epsilon=2$ Let x be the ratio of ChrX sequence tag density of male to female pregnancies. In this study, the denominator of this ratio is taken to be the median sequence tag density of all female pregnancies.

Thus, fetal DNA fraction $\epsilon=2(1-x)$
From ChrY:

Fetal DNA fraction $\epsilon$=(sequence tag density of ChrY in maternal plasma/sequence tag density of ChrY in male plasma)

Note that in these derivations, we assume that the total number of sequence tags obtained is the same for all samples. In reality, the total number of sequence tags obtained for different sample is different, and we have taken into account such differences in our estimation of fetal DNA fraction by normalizing the sequence tag density of each chromosome to the median of the autosomal sequence tag densities for each sample.

Calculating Fetal DNA Fraction in Maternal Plasma of Aneuploid (Trisomy) Pregnancies:

Let fetal DNA fraction be $\epsilon$

|  | Maternal Contribution | Trisomic Fetus Contribution | Disomic Fetus Contribution |
|---|---|---|---|
| Trisomic Chromosome | $2(1-\epsilon)$ | $3\epsilon$ | $2\epsilon$ |

$$\frac{\text{Trisomic pregnancies trisomic chromosome}}{\text{sequence counts(fetal and maternal)}} = 2(1-\varepsilon) + 3\varepsilon = 2 + \varepsilon$$

$$\frac{\text{Disomic pregnancies trisomic chromosome}}{\text{sequence counts(fetal and maternal)}} = 2(1-\varepsilon) + 2\varepsilon = 2$$

Let x be the ratio of trisomic chromosome sequence counts (or sequence tag density) of trisomic to disomic pregnancies. In this study, the denominator of this ratio is taken to be the median sequence tag density of all disomic pregnancies.

Thus, fetal DNA fraction $\epsilon=2(x-1)$.

Example 8

Correction of Sequence Tag Density Bias Resulting from G/C or A/T Content Among Different Chromosomes in a Sample This example shows a refinement of results indicating sequences mapping to different chromosomes and permitting the determination of the count of different chromosomes or regions thereof. That is, the results as shown in FIG. 1A may be corrected to eliminate the variations in sequence tag density shown for chromosomes higher in G/C content, shown towards the right of the Figure. This spread of values results from sequencing bias in the method used, where a greater number of reads tend to be obtained depending on G/C content. The results of the method of this example are shown in FIG. 10. FIG. 10 is an overlay which shows the results from a number of different samples, as indicated in the legend. The sequence tag density values in FIGS. 1 and 10 were normalized to those of a male genomic DNA control, since the density values are not always 1 for all the chromosomes (even after GC correction) but are consistent among a sample. For example, after GC correction, values from all samples for chr19 cluster around 0.8 (not shown). Adjusting the data to a nominal value of 1 can be done by plotting the value relative to the male gDNA control. This makes the values for all chromosomes cluster around 1

Outlying chromosome sequence tag densities can be seen as significantly above a median sequence tag density; disomic chromosomes are clustered about a line running along a density value of about 1. As can be seen there, the results from chromosome 19 (far right, highest in G/C content), for example, show a similar value when disomic as other disomic chromosomes. The variations between chromosomes with low and high G/C content are eliminated from the data to be examined. Samples (such as P13 in the present study) which could not have been unambiguously interpreted now may be. Since G/C content is the opposite of A/T content, the present method will correct for both. Either G/C bias or A/T bias can result from different sequencing methods. For example, it has been reported by others that the Solexa method results in a higher number of reads from sequences where the G/C content is high. See, Dohm et al., "Substantial biases in ultra-short read data sets from high-throughput DNA sequencing," Nuc. Acids Res. 36(16), e105; doi:10.1093/nar/gkn425. The procedure of the present example follows the following steps:

a. Calculate G/C content of the human genome. Calculate the G/C content of every 20 kb non-overlapping window of each chromosome of the human genome (HG18) using the hgG/CPercent script of the UCSC Genome Browser's "kent source tree," which contains different utility programs, available to the public under license. The output file contains the coordinate of each 20 kb bin and the corresponding G/C content. It was found that a large number of reads were obtained higher G/C ranges (about 55-70%) and very few reads were obtained at lower G/C content percentages, with essentially none below about 30% G/C (data not shown). Because the actual length of a sequenced DNA fragment is not known (we only sequenced the first 25 bp of one end of a piece of DNA on the flow cell), and it's the G/C content of the entire piece of DNA that contributed to sequencing bias, an arbitrary window of known human genomic DNA sequence is chosen for determining G/C content of different reads. We chose a 20 kb window to look at the relationship between number of reads and GC content. The window can be much smaller e.g., 10 kb or 5 kb, but a size of 20 kb makes computation easier.

b. Calculate the relationship between sequence coverage and G/C content. Assign weight to each read according to G/C content. For each sample, the number of read per 20 kb bin is counted. The number of read is plotted against G/C content. The average number of read is calculated for every 0.1% G/C content, ignoring bins with no reads, bins with zero G/C percent, and bins with over-abundant reads. The reciprocal of the average number of reads for a particular G/C percent relative to the global median number of read is calculated as the weight. Each read is then assigned a weight depending on the G/C percent of the 20 kb window it falls into.

c. Investigate the distribution of reads across each autosome and chromosome X. In this step, the number of reads, both unweighted and weighted, in each non-overlapping 50 kb window is recorded. For counting, we chose a 50 kb window in order to obtain a reasonable number of reads per window and reasonable number of windows per chromosome to look at the distributions. Window size may be selected based on the number of reads obtained in a given experiment, and may vary over a wide range. For example, 30K-100K may be used. Known microsatellite regions are ignored. A graph showing the results of chr1 of P7 is shown in FIG. 11, which illustrates the weight distribution of this step (c) from sample P7, where the weight assigned to different G/C contents is shown; Reads with higher G/C content are overly represented than average and thus are given less weight.

d. Investigate the distribution of reads across chrY. Calculate the number of chrY reads in transcribed regions after applying weight to reads on chrY. Chromosome Y is treated individually because it is short and has many repeats. Even female genome sequence data will map in some part to chromosome Y, due to sequencing and alignment errors. The number of chrY reads in transcribed regions after applying weight to reads on chrY is used to calculate percentage of fetal DNA in the sample.

Example 9

Comparing Different Patient Samples Using Statistical Analyses (t Statistic)

This example shows another refinement of results as obtained using the previous examples. In this case, multiple patient samples are analyzed in a single process. FIG. 12 illustrates the results of an analysis of patients P13, P19, P31, P23, P26, P40, P42, P1, P2, P6, P7, P14, P17, P20, P52, P53, P57, P59 and P64, with their respective karyotypes indicated, as in Table 1, above. The dotted line shows the 99% confidence interval, and outliers may be quickly identified. It may be seen by looking below the line that male fetuses have less chromosome X (solid triangles). An exception is P19, where it is believed that there were not enough total reads for this analysis. It may be seen by looking above the line that trisomy 21 patients (solid circles) are P1, 2, 6, 7, 14, 17, 20, 52 and 53. P57 and 59 have trisomy 18 (open diamonds) and P64 has trisomy 13 (star). This method may be presented by the following three step process:

Step 1: Calculate at statistic for each chromosome relative to all other chromosome in a sample. Each t statistic tells the value of each chromosome median relative to other chromosomes, taking into account the number of reads mapped to each chromosome (since the variation of the median scales with the number of reads). As described above, the present analyses yielded about 5 million reads per sample. Although one may obtain 3-10 million reads per sample, these are short reads, typically only about 20-100 bp, so one has actually only sequenced, for example about 300 million of the 3 billion by in the human genome. Thus, statistical methods are used where one has a small sample and the standard deviation of the population (3 billion, or 47 million for chromosome 21) is unknown and it is desired to estimate it from the sample number of reads in order to determine the significance of a numerical variation. One way to do this is by calculating Student's t-distribution, which may be used in place of a normal distribution expected from a larger sample. The t-statistic is the value obtained when the t-distribution is calculated. The formula used for this calculation is given below. Using the methods presented here, other t-tests can be used.

Step 2: Calculate the average t statistic matrix by averaging the values from all samples with disomic chromosomes. Each patient sample data is placed in at matrix, where the row is chr1 to chr22, and the column is also chr1 to chr22. Each cell represents the t value when comparing the chromosomes in the corresponding row and column (i.e., position (2,1) in the matrix is the t-value of when testing chr2 and chr1) the diagonal of the matrix is 0 and the matrix is symmetric. The number of reads mapping to a chromosome is compared individually to each of chr1-22.

Step 3: Subtract the average t statistic matrix from the t statistic matrix of each patient sample. For each chromosome, the median of the difference in t statistic is selected as the representative value.

The t statistic for 99% confidence for large number of samples is 3.09. Any chromosome with a representative t statistic outside −3.09 to 3.09 is determined as non-disomic.

Example 10

Calculation of Required Number of Sequence Reads after G/C Bias Correction

In this example, a method is presented that was used to calculate the minimum concentration of fetal DNA in a sample that would be needed to detect an aneuploidy, based on a certain number of reads obtained for that chromosome (except chromosome Y). FIG. 13 and FIG. 14 show results obtained from 19 patient plasma DNA samples, 1 donor plasma DNA sample, and duplicate runs of a donor gDNA sample. It is estimated in FIG. 13 that the minimum fetal DNA % of which over-representation of chr21 can be detected at the best sampling rate (~70 k reads mapped to chr21) is ~6%. (indicated by solid lines in FIG. 13). The lines are drawn between about $0.7 \times 10^5$ reads and 6% fetal DNA concentration. It can be expected that higher numbers of reads (not exemplified here) the needed fetal DNA percentage will drop, probably to about 4%.

In FIG. 14, the data from FIG. 13 are presented in a logarithmic scale. This shows that the minimum required fetal DNA concentration scales linearly with the number of reads in a square root relationship (slope of −0.5). These calculations were carried out as follows:

For large n (n>30), t statistic $$t = \frac{\overline{y_2} - \overline{y_1}}{\sqrt{\frac{s_2^2}{n_2} + \frac{s_1^2}{n_1}}},$$

where $\overline{y_2} - \overline{y_1}$ is the difference in means (or amount of over- or under-representation of a particular chromosome) to be measured; s is the standard deviation of the number of reads per 50 kb in a particular chromosome; n is the number of samples (i.e., the number of 50 kb windows per chromosome). Since the number of 50 kb windows per chromosome is fixed, $n_1 = n_2$. If we assume that $$s_1 \approx s_2,$$

$$\overline{y_2} - \overline{y_1} \approx t\sqrt{\frac{2s_1^2}{n_1}}$$

$$= sqrt(2) * \text{half width of the confidence interval}$$

at confidence level governed by the value of $t$.

Thus, $$\frac{\overline{y_2}}{\overline{y_1}} - 1 \approx \frac{t\sqrt{\frac{2s_1^2}{n_1}}}{\overline{y_1}}.$$

For every chromosome in every sample, we can calculate the value $$\frac{t\sqrt{\frac{2s_1^2}{n_1}}}{\overline{y_1}},$$

which corresponds to the minimum over- or under-representation $$\left(\frac{\overline{y_2}}{\overline{y_1}} - 1\right)$$

that can be resolved with confidence level governed by the value of t. Note that $$2*\left(\frac{\overline{y_2}}{\overline{y_1}} - 1\right)*100\%$$

corresponds to the minimum fetal DNA % of which any over- or under-representation of chromosomes can be detected. We expect the number of reads mapped to each chromosome to play a role in determining standard deviation $s_1$, since according to Poisson distribution, the standard deviation equals to the square root of the mean. By plotting $$2*\left(\frac{\overline{y_2}}{\overline{y_1}} - 1\right)*100\% \text{ vs.}$$

number of reads mapped to each chromosome in all the samples, we can evaluate the minimum fetal DNA % of which any over- or under-representation of chromosomes can be detected given the current sampling rate.

After correction of G/C bias, the number of reads per 50 kb window for all chromosomes (except chromosome Y) is normally distributed. However, we observed outliers in some chromosomes (e.g., a sub-region in chromosome 9 has near zero representation; a sub-region in chromosome 20 near the centromere has unusually high representation) that affect the calculation of standard deviation and the mean. We therefore chose to calculate confidence interval of the median instead of the mean to avoid the effect of outliers in the calculation of confidence interval. We do not expect the confidence interval of the median and the mean to be very different if the small number of outliers has been removed. The 99.9% confidence interval of the median for each chromosome is estimated from bootstrapping 5000 samples from the 50 kb read distribution data using the percentile method. The half width of the confidence interval is estimated as 0.5*confidence interval. We plot 2*(half width of confidence interval of median)/median*100% vs. number of reads mapped to each chromosome for all samples.

Bootstrap resampling and other computer-implemented calculations described here were carried out in MATLAB®, available from The Mathworks, Natick, Mass.

CONCLUSION

The above specific description is meant to exemplify and illustrate the invention and should not be seen as limiting the scope of the invention, which is defined by the literal and equivalent scope of the appended claims. Any patents or publications mentioned in this specification are intended to convey details of methods and materials useful in carrying out certain aspects of the invention which may not be explicitly set out but which would be understood by workers in the field. Such patents or publications are hereby incorporated by reference to the same extent as if each was specifically and individually incorporated by reference, as needed for the purpose of describing and enabling the method or material referred to.

REFERENCES

1. Cunningham F, et al. (2002) in Williams Obstetrics (McGraw-Hill Professional, New York), p. 942.
2. (2007) ACOG Practice Bulletin No. 88, December 2007. Invasive prenatal testing for aneuploidy. *Obstet Gynecol*, 110: 1459-1467.
3. Wapner R, et al. (2003) First-trimester screening for trisomies 21 and 18. *N Engl J Med*, 349: 1405-1413.
4. Alfirevic Z, Neilson J P (2004) Antenatal screening for Down's syndrome. *Bmj* 329: 811-812.
5. Malone F D, et al. (2005) First-trimester or second-trimester screening, or both, for Down's syndrome. *N Engl J Med*, 353: 2001-2011.
6. Herzenberg L A, et al. (1979) Fetal cells in the blood of pregnant women: detection and enrichment by fluorescence-activated cell sorting. *Proc Natl Acad Sci USA*, 76: 1453-1455.
7. Bianchi D W, et al. (1990) Isolation of fetal DNA from nucleated erythrocytes in maternal blood. *Proc Natl Acad Sci USA*, 87: 3279-3283.
8. Cheung M C, Goldberg J D, Kan Y W (1996) Prenatal diagnosis of sickle cell anaemia and thalassaemia by analysis of fetal cells in maternal blood. *Nat Genet*, 14: 264-268.
9. Bianchi D W, et al. (1997) PCR quantitation of fetal cells in maternal blood in normal and aneuploid pregnancies. *Am J Hum Genet*, 61: 822-829.
10. Bianchi D W, et al. (2002) Fetal gender and aneuploidy detection using fetal cells in maternal blood: analysis of NIFTY I data. National Institute of Child Health and Development Fetal Cell Isolation Study. *Prenat Diagn*, 22: 609-615.
11. Lo Y M, et al. (1997) Presence of fetal DNA in maternal plasma and serum. *Lancet*, 350: 485-487.
12. Dennis Lo Y M, Chiu R W (2007) Prenatal diagnosis: progress through plasma nucleic acids. *Nat Rev Genet*, 8: 71-77.
13. Lo Y M, et al. (1998) Quantitative analysis of fetal DNA in maternal plasma and serum: implications for noninvasive prenatal diagnosis. *Am J Hum Genet*, 62: 768-775.
14. Lo Y M, et al. (2007) Plasma placental RNA allelic ratio permits noninvasive prenatal chromosomal aneuploidy detection. *Nat Med*, 13: 218-223.
15. Tong Y K, et al. (2006) Noninvasive prenatal detection of fetal trisomy 18 by epigenetic allelic ratio analysis in maternal plasma: Theoretical and empirical considerations. *Clin Chem*, 52: 2194-2202.
16. Dhallan R, et al. (2007) A non-invasive test for prenatal diagnosis based on fetal DNA present in maternal blood: a preliminary study. *Lancet*, 369: 474-481.
17. Fan H C, Quake S R (2007) Detection of aneuploidy with digital polymerase chain reaction. *Anal Chem*, 79: 7576-7579.
18. Lo Y M, et al. (2007) Digital PCR for the molecular detection of fetal chromosomal aneuploidy. *Proc Natl Acad Sci USA*, 104: 13116-13121.
19. Quake S R, Fan H C. (2006). Non-invasive fetal genetic screening by digital analysis. USA Provisional Patent Application No. 60/764,420. 20. Mardis E R (2008) Next-Generation DNA Sequencing Methods. *Annu Rev Genomics Hum Genet*, 9: 387-402.
20. Lander E S, et al. (2001) Initial sequencing and analysis of the human genome. *Nature*, 409: 860-921.
21. Chan K C, et al. (2004) Size distributions of maternal and fetal DNA in maternal plasma. *Clin Chem*, 50: 88-92.
22. Li Y, et al. (2004) Size separation of circulatory DNA in maternal plasma permits ready detection of fetal DNA polymorphisms. *Clin Chem*, 50: 1002-1011.
23. Cooper G, Hausman R (2007) in The cell: a molecular approach (Sinauer Associates, Inc, Sunderland), p. 168.
24. Jahr S, et al. (2001) DNA fragments in the blood plasma of cancer patients: quantitations and evidence for their origin from apoptotic and necrotic cells. *Cancer Res*, 61: 1659-1665.
25. Giacona M B, et al. (1998) Cell-free DNA in human blood plasma: length measurements in patients with pancreatic cancer and healthy controls. *Pancreas*, 17: 89-97.
26. Schones D E, et al. (2008) Dynamic regulation of nucleosome positioning in the human genome. *Cell*, 132: 887-898.
27. Ozsolak F, Song J S, Liu X S, Fisher D E (2007) High-throughput mapping of the chromatin structure of human promoters. *Nat Biotechnol*, 25: 244-248.
28. Yuan G C, et al. (2005) Genome-scale identification of nucleosome positions in S. cerevisiae. *Science*, 309: 626-630.
29. Lee W, et al. (2007) A high-resolution atlas of nucleosome occupancy in yeast. *Nat Genet*, 39: 1235-1244.
30. Sohda S, et al. (1997) The proportion of fetal nucleated red blood cells in maternal blood: estimation by FACS analysis. *Prenat Diagn*, 17: 743-752.
31. Hamada H, et al. (1993) Fetal nucleated cells in maternal peripheral blood: frequency and relationship to gestational age. *Hum Genet*, 91: 427-432.
32. Nelson J L (2008) Your cells are my cells. *Sci Am*, 298: 64-71.
33. Khosrotehrani K, Bianchi D W (2003) Fetal cell microchimerism: helpful or harmful to the parous woman? *Curr Opin Obstet Gynecol*, 15: 195-199.
34. Lo Y M, et al. (1999) Rapid clearance of fetal DNA from maternal plasma. *Am J Hum Genet*, 64: 218-224.
35. Smid M, et al. (2003) No evidence of fetal DNA persistence in maternal plasma after pregnancy. *Hum Genet*, 112: 617-618.
36. Rijnders R J, Christiaens G C, Soussan A A, van der Schoot C E (2004) Cell-free fetal DNA is not present in plasma of nonpregnant mothers. *Clin Chem*, 50: 679-681; author reply 681.
37. Hillier L W, et al. (2008) Whole-genome sequencing and variant discovery in C. elegans. *Nat Methods*, 5: 183-188.
38. Dohm J C, Lottaz C, Borodina T, Himmelbauer H (2008) Substantial biases in ultra-short read data sets from high-throughput DNA sequencing. *Nucleic Acids Res*.
39. Harris T D, et al. (2008) Single-molecule DNA sequencing of a viral genome. *Science*, 320: 106-109.
40. Samura O, et al. (2003) Cell-free fetal DNA in maternal circulation after amniocentesis. *Clin Chem*, 49: 1193-1195.
41. Lo Y M, et al. (1999) Increased fetal DNA concentrations in the plasma of pregnant women carrying fetuses with trisomy 21. *Clin Chem*, 45: 1747-1751.
42. Segal E, et al. (2006) A genomic code for nucleosome positioning. *Nature*, 442: 772-778.

What is claimed is:

1. A method of testing for an abnormal distribution of a chromosome in a sample comprising a mixture of maternal and fetal DNA, comprising the steps of:
   (a) obtaining maternal and fetal DNA from said sample;
   (b) sequencing predefined subsequences of the maternal and fetal DNA to obtain a plurality of sequence tags aligning to the predefined subsequences, wherein said sequence tags are of sufficient length to be assigned to a specific predefined subsequence, wherein the predefined subsequences are from a plurality of different chromosomes, and wherein said plurality of different chromosomes comprise at least one first chromosome suspected of having an abnormal distribution in said sample and at least one second chromosome presumed to be normally distributed in said sample;
   (c) assigning the plurality of sequence tags to their corresponding predetermined subsequences;
   (d) determining a number of sequence tags aligning to the predetermined subsequences of said first chromosome and a number of sequence tags to the predetermined subsequences of the second chromosome; and
   (e) comparing the numbers from step (d) to determine the presence or absence of an abnormal distribution of said first chromosome.

2. The method of claim 1 wherein the sample is a maternal serum or plasma sample, wherein the abnormal distribution of said first chromosome is a fetal aneuploidy, and wherein said second chromosome is a euploid chromosome.

3. The method of claim 2 wherein the sequencing comprises massively parallel sequencing of the predefined subsequences.

4. The method of claim 3 wherein said massively parallel sequencing comprises attaching DNA fragments to an optically transparent surface, conducing solid phase amplification of the attached DNA fragments to create a high density sequencing flow cell with millions of DNA clusters, and sequencing the DNA clusters by a four-color DNA sequencing-by-synthesis method employing reversible terminators with removable fluorescent dyes.

5. The method of claim 2 wherein the fetal aneuploidy is an aneuploidy of a chromosome selected from the group consisting of chromosome 13, chromosome 18 and chromosome 21.

6. The method of claim 2 wherein the step of assigning sequence tags to corresponding chromosome portions allows one mismatch.

7. The method of claim 2 wherein the length of the sequence tags is from about 25 bp to about 100 bp in length.

8. The method of claim 2 wherein the DNA is genomic DNA.

9. The method of claim 2 wherein said sequencing comprises selectively sequencing nucleic acid molecules comprising the predefined sequences.

10. The method of claim 9 wherein said sequencing comprises the use of a sequencing array.

11. The method of claim 10 wherein said selected defined subsequences of the genomic DNA are rendered single-stranded and captured under hybridizing conditions by single-stranded probes physically separated on an array.

12. The method of claim 2 further comprising determination of fetal DNA fraction of the DNA obtained from the maternal serum or plasma sample.

13. The method of claim 12 wherein the fetal DNA fraction is determined by digital PCR.

14. A method of testing for an abnormal distribution of a chromosome in a sample comprising a mixture of maternal and fetal DNA, comprising the steps of:
   (a) obtaining maternal and fetal DNA from said sample;
   (b) sequencing predefined subsequences of the maternal and fetal DNA to obtain a plurality of sequence tags aligning to the predefined subsequences, wherein said sequence tags are of sufficient length to be assigned to a specific predefined subsequence, wherein the predefined subsequences are from a plurality of different chromosomes, and wherein said plurality of different chromosomes comprise at least one first chromosome suspected of having an abnormal distribution in said sample and at least one second chromosome presumed to be normally distributed in said sample;
   (c) assigning the plurality of sequence tags to their corresponding predetermined subsequences;
   (d) determining a relative number of sequence tags aligning to the predetermined subsequences of said first chromosome and to the predetermined subsequences of said second chromosome;
   (e) determining a weight for correcting for G/C bias and applying the weight to the numbers of sequence tags determined in step (d) to obtain a corrected number of sequence tags assigned to the predefined subsequences of the first chromosome and a corrected number of sequence tags assigned to the predefined subsequences of the second chromosome; and
   (f) comparing the corrected number of sequence tags aligning to the predetermined subsequences of said first chromosome to the corrected number of sequence tags aligning to the predetermined subsequences of said second chromosome to determine the presence or absence of an abnormal distribution of said first chromosome.

15. The method of claim 14 wherein the sample is a maternal serum or plasma sample, wherein the abnormal distribution of said first chromosome is a fetal aneuploidy, and wherein said second chromosome is a euploid chromosome.

\* \* \* \* \*

UNITED STATES PATENT AND TRADEMARK OFFICE
CERTIFICATE OF CORRECTION

| | | |
|---|---|---|
| PATENT NO. | : 8,296,076 B2 | Page 1 of 1 |
| APPLICATION NO. | : 13/452083 | |
| DATED | : October 23, 2012 | |
| INVENTOR(S) | : Hei-Mun Christina Fan and Stephen R. Quake | |

It is certified that error appears in the above-identified patent and that said Letters Patent is hereby corrected as shown below:

Title Page, Item (54) in the title, line 2, replace "ANEUOPLOIDY" with
--ANEUPLOIDY--.

Signed and Sealed this
Twenty-fifth Day of December, 2012

David J. Kappos
*Director of the United States Patent and Trademark Office*

UNITED STATES PATENT AND TRADEMARK OFFICE
CERTIFICATE OF CORRECTION

PATENT NO. : 8,296,076 B2  
APPLICATION NO. : 13/452083  
DATED : October 23, 2012  
INVENTOR(S) : Hei-Mun Christina Fan and Stephen R. Quake Page 1 of 1

It is certified that error appears in the above-identified patent and that said Letters Patent is hereby corrected as shown below:

Title Page, Item (54), line 2, and at Column 1, line 2, in the title, replace "ANEUOPLOIDY" with --ANEUPLOIDY--.

This certificate supersedes the Certificate of Correction issued December 25, 2012.

Signed and Sealed this  
Nineteenth Day of February, 2013

Teresa Stanek Rea  
*Acting Director of the United States Patent and Trademark Office*

SEQUENCE LISTING

```
<160> NUMBER OF SEQ ID NOS: 9

<210> SEQ ID NO 1
<211> LENGTH: 19
<212> TYPE: DNA
<213> ORGANISM: artificial
<220> FEATURE:
<223> OTHER INFORMATION: synthetic oligonucleotide sequence derived from
      locus EIF2C1 on human chromosome 1

<400> SEQUENCE: 1
gttcggcttt caccagtct                                                       19

<210> SEQ ID NO 2
<211> LENGTH: 20
<212> TYPE: DNA
<213> ORGANISM: artificial
<220> FEATURE:
<223> OTHER INFORMATION: synthetic oligonucleotide sequence derived from
      locus EIF2C1 on human chromosome 1

<400> SEQUENCE: 2
ctccatagct ctccccactc                                                      20

<210> SEQ ID NO 3
<211> LENGTH: 19
<212> TYPE: DNA
<213> ORGANISM: artificial
<220> FEATURE:
<223> OTHER INFORMATION: synthetic oligonucleotide sequence derived from
      locus EIF2C1 on human chromosome 1
```

<400> SEQUENCE: 3
gccctgccat gtggaagat                                                19

<210> SEQ ID NO 4
<211> LENGTH: 20
<212> TYPE: DNA
<213> ORGANISM: artificial
<220> FEATURE:
<223> OTHER INFORMATION: synthetic oligonucleotide sequence derived from
      locus SRY on the human Y chromosome

<400> SEQUENCE: 4
cgcttaacat agcagaagca                                               20

<210> SEQ ID NO 5
<211> LENGTH: 20
<212> TYPE: DNA
<213> ORGANISM: artificial
<220> FEATURE:
<223> OTHER INFORMATION: synthetic oligonucleotide sequence derived from
      locus SRY on the human Y chromosome

<400> SEQUENCE: 5
agtttcgaac tctggcacct                                               20

<210> SEQ ID NO 6
<211> LENGTH: 25
<212> TYPE: DNA
<213> ORGANISM: artificial
<220> FEATURE:
<223> OTHER INFORMATION: synthetic oligonucleotide sequence derived from
      locus SRY on the human Y chromosome

<400> SEQUENCE: 6
tgtcgcactc tccttgtttt tgaca                                         25

<210> SEQ ID NO 7
<211> LENGTH: 20
<212> TYPE: DNA
<213> ORGANISM: artificial
<220> FEATURE:
<223> OTHER INFORMATION: synthetic oligonucleotide sequence derived from
      locus DYS14 on the human Y chromosome

<400> SEQUENCE: 7
atcgtccatt tccagaatca                                               20

<210> SEQ ID NO 8
<211> LENGTH: 18
<212> TYPE: DNA
<213> ORGANISM: artificial
<220> FEATURE:
<223> OTHER INFORMATION: synthetic oligonucleotide sequence derived from
      locus DYS14 on the human Y chromosome

<400> SEQUENCE: 8
gttgacagcc gtggaatc                                                 18

<210> SEQ ID NO 9
<211> LENGTH: 27
<212> TYPE: DNA
<213> ORGANISM: artificial
<220> FEATURE:
<223> OTHER INFORMATION: synthetic oligonucleotide sequence derived from
      locus DYS14 on the human Y chromosome -continued

```
<400> SEQUENCE: 9
tgccacagac tgaactgaat gattttc                                          27
```